US 10,800,790 B2
Oct. 13, 2020

(12) United States Patent
Chang et al.

(54) SESQUITERPENOID STAT3 INHIBITORS

(71) Applicant: University of Hawaii, Honolulu, HI (US)

(72) Inventors: Leng Chee Chang, Hilo, HI (US); James Turkson, Honolulu, HI (US); Supakit Wongwiwatthananukit, Hilo, HI (US); Ui Joung Youn, Hilo, HI (US); Dianqing Sun, Hilo, HI (US)

(73) Assignee: UNIVERSITY OF HAWAII, Honolulu, HI (US)

( * ) Notice: Subject to any disclaimer, the term of this patent is extended or adjusted under 35 U.S.C. 154(b) by 0 days.

(21) Appl. No.: 14/896,846

(22) PCT Filed: Jun. 20, 2014

(86) PCT No.: PCT/US2014/043523
§ 371 (c)(1),
(2) Date: Dec. 8, 2015

(87) PCT Pub. No.: WO2014/205416
PCT Pub. Date: Dec. 24, 2014

(65) Prior Publication Data
US 2016/0137663 A1    May 19, 2016

Related U.S. Application Data

(60) Provisional application No. 61/837,613, filed on Jun. 20, 2013.

(51) Int. Cl.
*C07D 493/18* (2006.01)
*C07D 493/08* (2006.01)

(52) U.S. Cl.
CPC ......... *C07D 493/18* (2013.01); *C07D 493/08* (2013.01)

(58) Field of Classification Search
None
See application file for complete search history.

(56) References Cited

PUBLICATIONS

Kuo et al. (Chem Pharm Bull, 2003, 51, 425-426).*
Chea et al. (Chem. Pharm. Bull. 54, 1437-1439, 2006).*
Hout et al. (Journal of Ethnopharmacology, 107, 12-18, 2006).*
Chen et al. (Natural Product Research, 2006, 20, 125-129).*
Ito et al. (Cancer Science, 2003, 94, 3-8).*
STN registry database compound 1394209-92-7 (entered STN Sep. 14, 2012) (Year: 2012).*
Youn et al. (Bioorganic & Medicinal Chemistry Letters, 22, 5559-5562; published online Jul. 15, 2012 (Year: 2012).*
STN registry database compound 1394156-45-6 (entered STN Sep. 13, 2012) (Year: 2012).*
Borkosky et al. (Phytochemistry, 44, 465-470, 1997) (Year: 1997).*
Youn et al. (Fitoterapia, 93, 194-200, published online Dec. 24, 2013; NPL document 44 of IDS dated May 4, 2016) (Year: 2013).*
Shaner et al. in Pesticide Biotransformation in Plants and Microorganisms (Hall, J. et al.); ACS Symposium Series, American Chemical Society: Washington, DC, 2000 (p. 356 2nd paragraph) (Year: 2000).*
Ayala, I., et al., An efficient protocol for the complete incorporation of methyl-protonated alanine in perdeuterated protein, Journal of biomolecular NMR, 2009, 43: p. 111-9.
Ball, M. et al., Total synthesis of thapsigargin, a potent SERCA pump inhibitor. Org Lett 2007, 9: p. 663-666.
Borkosky, S, et al., Glaucolides, hirsutinolides and other sesquiterpene lactones from *Vernonanthura pinguis*. Phytochemistry 1997, 44:465-70.
Butturini, E., et al., Two naturally occurring terpenes, dehydrocostuslactone and costunolide, decrease intracellular GSH content and inhibit STAT3 activation, PLoS One 2011;6:e20174.
Chea, A et al., Antimalarial Activity of Sesquiterpene Lactones from *Veronia cinerea*, Chem. Pharm. Bull 2006, 54, 1437-1439.
"Dictionnaire des plantes utiliesees au Cambodge," Olympic, Phnom Penh, 2000, p. 915.
Garcia, R., et al., Constitutive activation of STAT3 by the Src and JAK tyrosine kinases participates in growth regulation of human breast carcinoma cells,Oncogene, 2001, 20: p. 2499-2513.
Garcia-Pineres, A.J. et al., Cysteine 38 in p65/NF-κB plays a crucial role in DNA binding inhibition by sesquiterpene lactones, J Biol Chem 2001;276:39713-20.
Garcia-Pineres A.J. et al., Role of cysteine residues of p65/NF-κB on the inhibition by the sesquiterpene lactone parthenolide and N-ethyl maleimide, and on its transactivating potential, Life Sci 2004;75:841-56.
Gardner, H.W. et al., Biotransformation of linoleic acid by *Clavibacter* sp. ALA2: heterocyclic and heterobicyclic fatty acids, Lipids 2000;35:1055-60.
Gelis, I., et al., Structural basis for signal-sequence recognition by the translocase motor SecA as determined by NMR, Cell, 2007, 131: p. 756-69.
Goto, N.K., et al., A robust and cost-effective method for the production of Val, Leu, Ile (delta 1) methyl-protonated 15N-, 13C-, 2H-labeled proteins, Journal of biomolecular NMR, 1999, 13: p. 369-74.
Granger, C. R., Medicinal plants of Seychelles, J. Roy. Soc. Health, 1996, 116, 107-109.
Gunasingh, C. et al., Flavonoids of the Flowers of *Veronia cinerea*, Indian J. Pharm. Sci. 1981. 43, 114.
Hooker, J.D., The flora of British India, III, London: L. Reeve and Co. Ltd., 1882, p. 233.
Hu, W., et al., Selective editing of Val and Leu methyl groups in high molecular weight protein NMR, Journal of biomolecular NMR, 2012, 53: p. 113-24.
Nanaga, J., et al., A rapid esterification by means of mixed anhydride and its application to large-ring lactonization. Bull Chem Soc Jpn 1979, 52: p. 1989-1993.
International Search Report in International Patent Application No. PCT/US2014/043523, dated Nov. 3, 2014, in 4 pages.
Jain, S. P. et al., Ethnopharmacol. 1984, 12, 213-222.

(Continued)

*Primary Examiner* — Jared Barsky
(74) *Attorney, Agent, or Firm* — Duane Morris LLP

(57) ABSTRACT

The present disclosure provides a method of purifying pharmaceutical compositions consisting essentially of STAT3 inhibitors from a mixture of compounds, pharmaceutical compositions comprising STAT3 inhibitors used to inhibit STAT3 in tumor cells, and certain pharmaceutically acceptable salts thereof, and methods of use.

5 Claims, 44 Drawing Sheets
(27 of 44 Drawing Sheet(s) Filed in Color)

(56) References Cited

PUBLICATIONS

Jakupovic, J. et al., Poskeanolide, a seco-germacranolide and other sesquiterpene lactones from *Vernonia* species, Phytochemistry 1986;25:1359-64.

Johnson, P.J., et al., Overexpressed pp60c-src can induce focus formation without complete transformation of NIH 3T3 cells, Mol. Cell. Biol., 1985. 5: p. 1073-1083.

Kirtikar, K.R. et al., "Indian Medicinal Plants, II," India: New Connaught Place, Dehradun, 1975, p. 1322.

Kuo YH, et al. Two novel sesquiterpene lactones, cytotoxic vernolide-A and -B, from Vernonia cinerea, Chem Pharm Bull 2003, 51:425-6.

Miklossy, G., T.S. Hilliard, and J. Turkson, Therapeutic modulators of STAT signaling for human diseases, Nat Rev Drug Discov, 2013, 12: p. 611-629.

Misra, T. N. et al. Phytochemistry 1984, 23, 415-417.

Park, K.E., et al., Three norisoprenoids from the brown alga *Sargassum thunbergii*, J Korean Chem Soc 2004;48:394-8.

Perez, C., et al., Absolute structures of two new C13-norisoprenoids from *Apollonias barbujana*, J Nat Prod 1996;59:69-72.

Pratheeshkumar, P. et al., Effect of vernolide-A, a sesquiterpene lactone rom *Vernonia Cinerea* L., on cell-mediated immune response in B16F-10 metastatic melanoma-bearing mice, Immunopharmacol. Immunotoxicol. 2011, 33, 533-538.

Pratheeshkumar et al. Modulation of cytotoxic T lymphocyte, natural killer cell, antibody-dependent cellular cytotoxicity, and antibody-dependent complement-mediated cytotoxicity by Veronica cinerea L. and vernolide-A in BALB/c mice via enhanced production of cytokines IL-2 and IFN-γ. Immunopharmacology and Immunotoxicology 34(1):46-55, 2012. [retrieved on Oct. 2, 2014]. Retrieved from the Internet: <URL: http://www.researchgate.net/publication/51886325_Modulation_of_cytotoxic_T_lymphocyte_natural_killer_cell_antibody-dependent_cellular_cytotoxicity_and_antibody-dependent_complement-mediated_cytotoxicity_by_Veronica_cinerea_L._and_vemolide-A_in_BALBc_mice_via_enhanced_production_of_cytokines_IL-2_and_IFN->.

Romanezi Da Silveira et al. Effect of crude extract of Veronica polyanthes Less. on blood pressure and renal sodium excretion in unanesthetized rats. Phytomedicine 10(2-3): 127-131, 2003. [retrieved on Oct. 2, 2014]. Retrieved from the Internet: <URL: http://www.researchgate.net/publication/10778245_Effect_of the_crude_extract_of_Veronica_polyanthes_Less._on_blood_pressure_and_renal_sodium_excretion_in_unanesthetized_rats>.

Ross, P.L., et al., Multiplexed protein quantitation in *Saccharomyces cerevisiae* using amine-reactive isobaric tagging reagents, Mol Cell Proteomics., 2004. 3: p. 1154-1169.

Schmidt, T.J. et al., Toxic activities of sesquiterpene lactones: Structural and biochemical aspects, Curr Org Chem 1999;3:577-608.

Tandon, M. et al., Insect Antifeedant Principles from *Vernonia cinerea*, Phytother. Res. 1998, 12, 195-199.

Tang, W.H., et al., Nonlinear fitting method for determining local false discovery rates from decoy database searches. J Proteome Res, 2008, 7: p. 3661-7.

Turkson, J. et al. (2004) Inhibition of constitutive signal transducer and activator of transcription 3 activation by novel platinum complexes with potent anti-tumor activity, Mol. Cancer Ther. 3:1533-1542.

Turkson, J. et al. (2004) Novel peptidomimetic inhibitors of signal transducer and activator of transcription 3 dimerization and biological activity, Mol Cancer Ther. 3:261-269.

Turkson, J., et al., Phosphotyrosyl peptides block STAT3-mediated DNA-binding activity, gene regulation and cell transformation, J. Biol. Chem., (2001), 276: p. 45443-45455.

Turkson, J. et al. (1998) STAT3 activation by Src induces specific gene regulation and is required for cell transformation. *Mol. Cell. Biol.* 18:2545-2552.

Wada, H. et al., Chemical and chemotaxonomic study of pteridophytes, Studies of the chemical constituents of *Alsophila spinulosa* Tryon, Chem Pharm Bull 1985;33:4182-7.

Wen, J., et al., Oxidative stress-mediated apoptosis. The anticancer effect of the sesquiterpene lactone parthenolide, J Biol Chem., 2002, 277: p. 38954-64.

Wisniewski, J.R., et al., Universal sample preparation method for proteome analysis. Nat Methods, 2009, 6: p. 359-62.

Xu, Y., et al., Targeting STAT3 suppresses growth of U251 cell-derived tumours in nude mice, J Clin Neurosci., 2012, 19: p. 443-6.

Yang et al. Cytotoxic Sesquiterpene Lactones from Pseudoelephantopus spicatus. J. Nat. Prod. 70(11):1761-1765, 2007. [retrieved on Oct. 2, 2014]. Retrieved from the Internet: <URL:http://pubs.acs.org/doi/abs/10.1021/np070331q>.

Youn et al., Anti-inflammatory sesquinterpene lactones from the flower Veronica cinerea. Bioorganic and Medicinal Chemistry Letters 22917): 5559-5562, 2012 [retrieved on Oct. 2, 2014]. Retrieved from the internet: <URL:http://www.researchgate.net/publication/230591631_Anti-inflammatory_sesquiterpene_lactones_from_the_flower_of_Veronica_cinerea>.

Youn et al. Bioactive sesquiterpene lactones and other compounds isolated from Veronica cinerea. Fitoterapia (2014) 93: 194-200. [retrieved on Oct. 2, 2014]. Retrieved from the Internet. <URL:http://www.researchgate.net/publication/259473455_Bioactive_sesquiterpene_lactones_and_other_compounds_isolated_from_Veronica_cinerea>.

Zhang, X. et al., A novel small-molecule disrupts Stat3 SH2 domain-hosphotyrosine interactions and Stat3-dependent tumor processes. Biochem Pharmacol. 2010; 79: 1398-1409.

Zhao, W., et al., A cell-permeable STAT3 SH2 domain mimetic inhibits STAT3 activation and induces antitumor cell effects in vitro. *J Biol Chem.* (2010) , 285:35855-35865.

\* cited by examiner

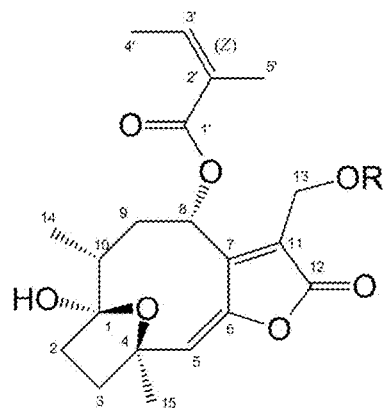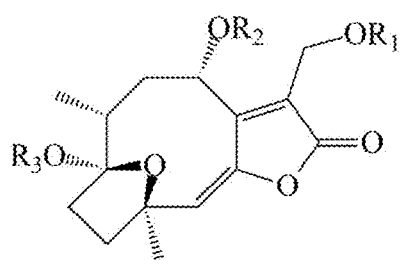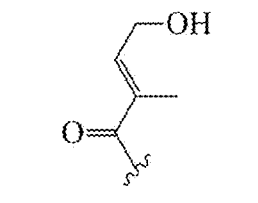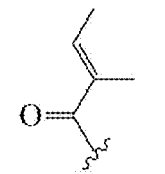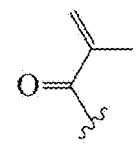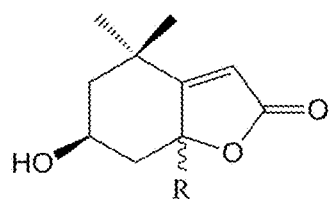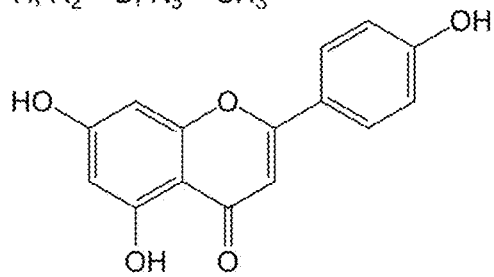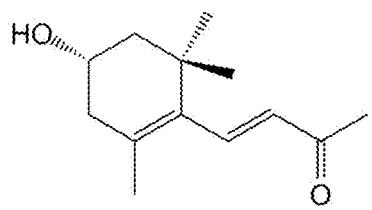
FIG. 2A

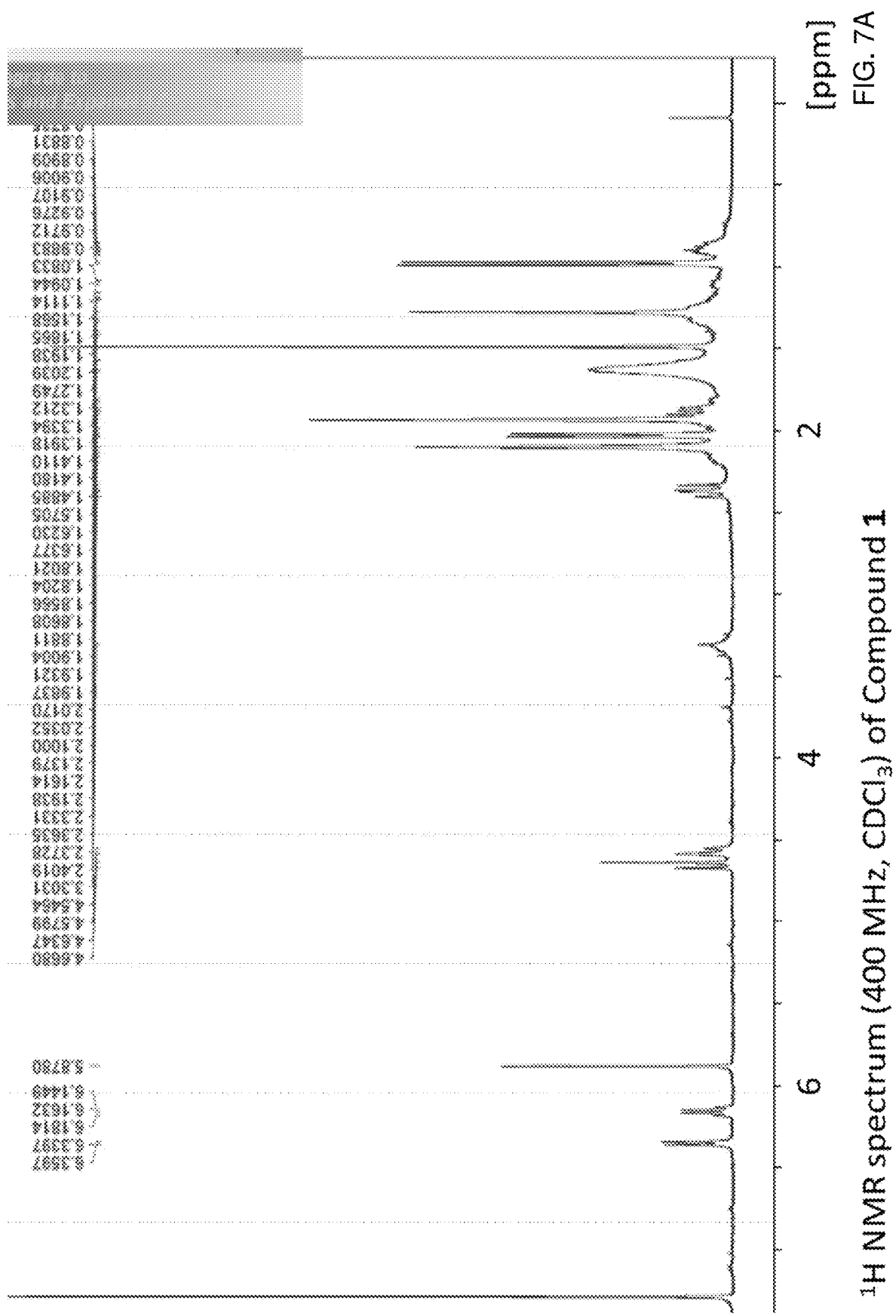
FIG. 7A ¹H NMR spectrum (400 MHz, CDCl₃) of Compound 1

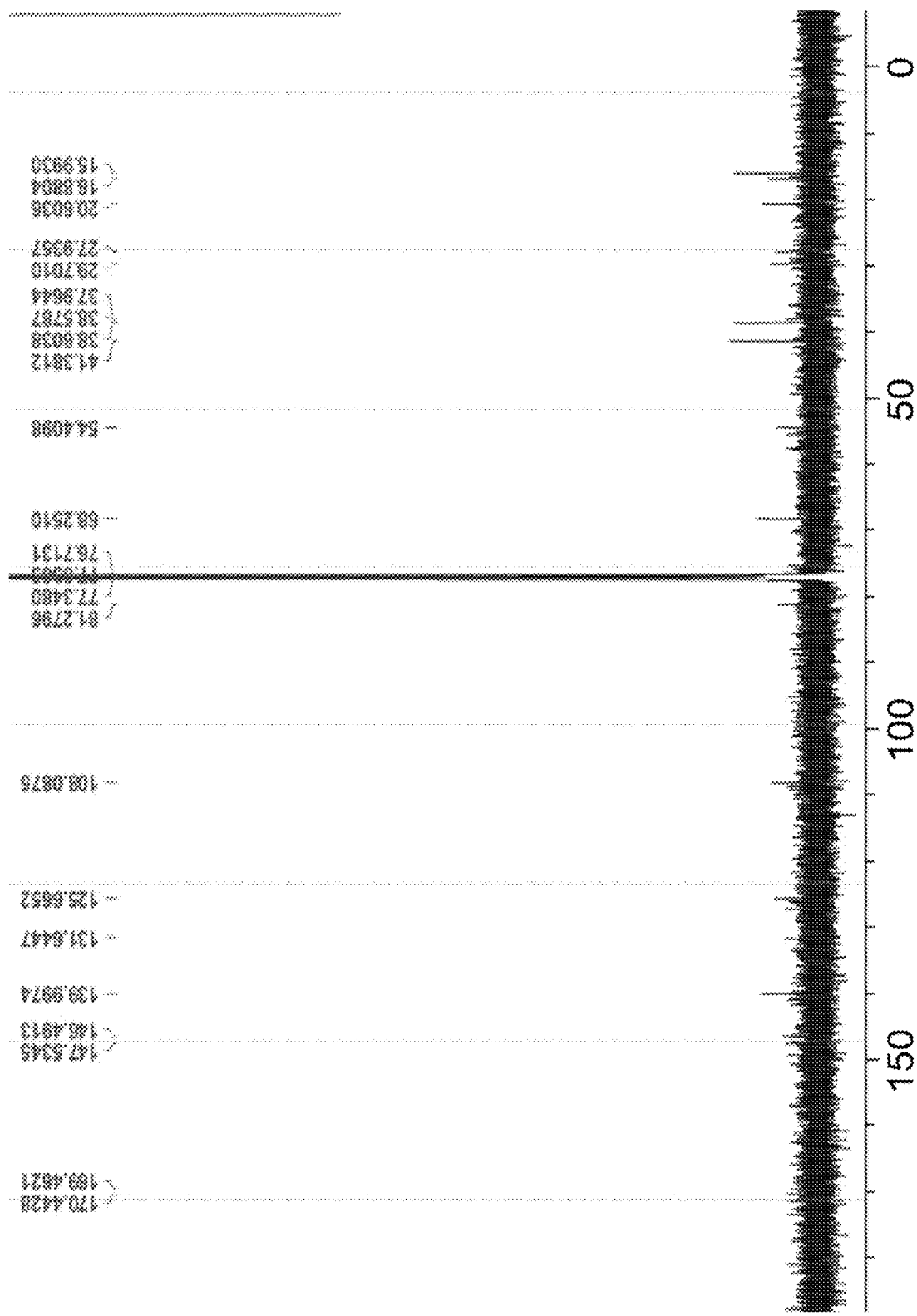

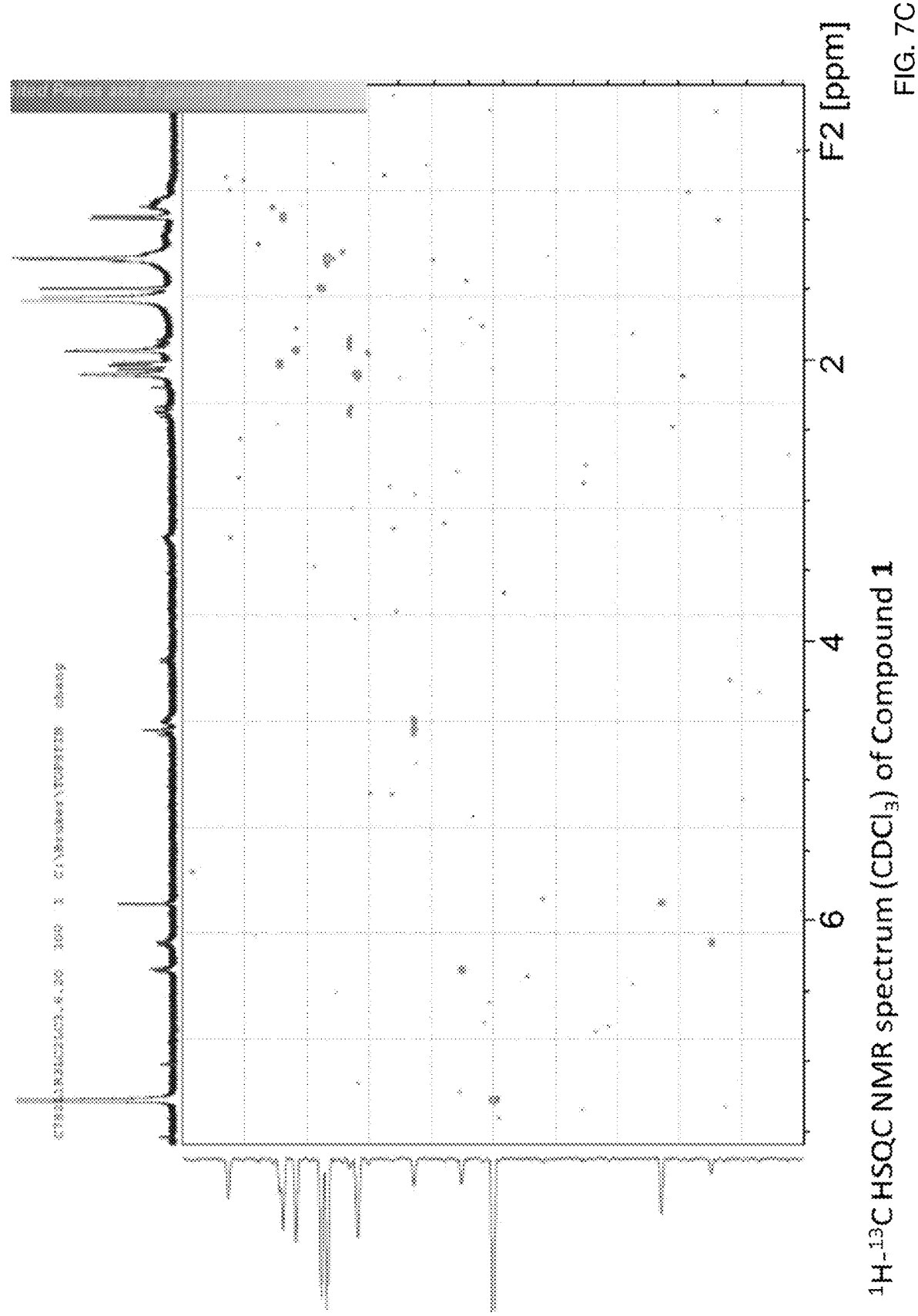

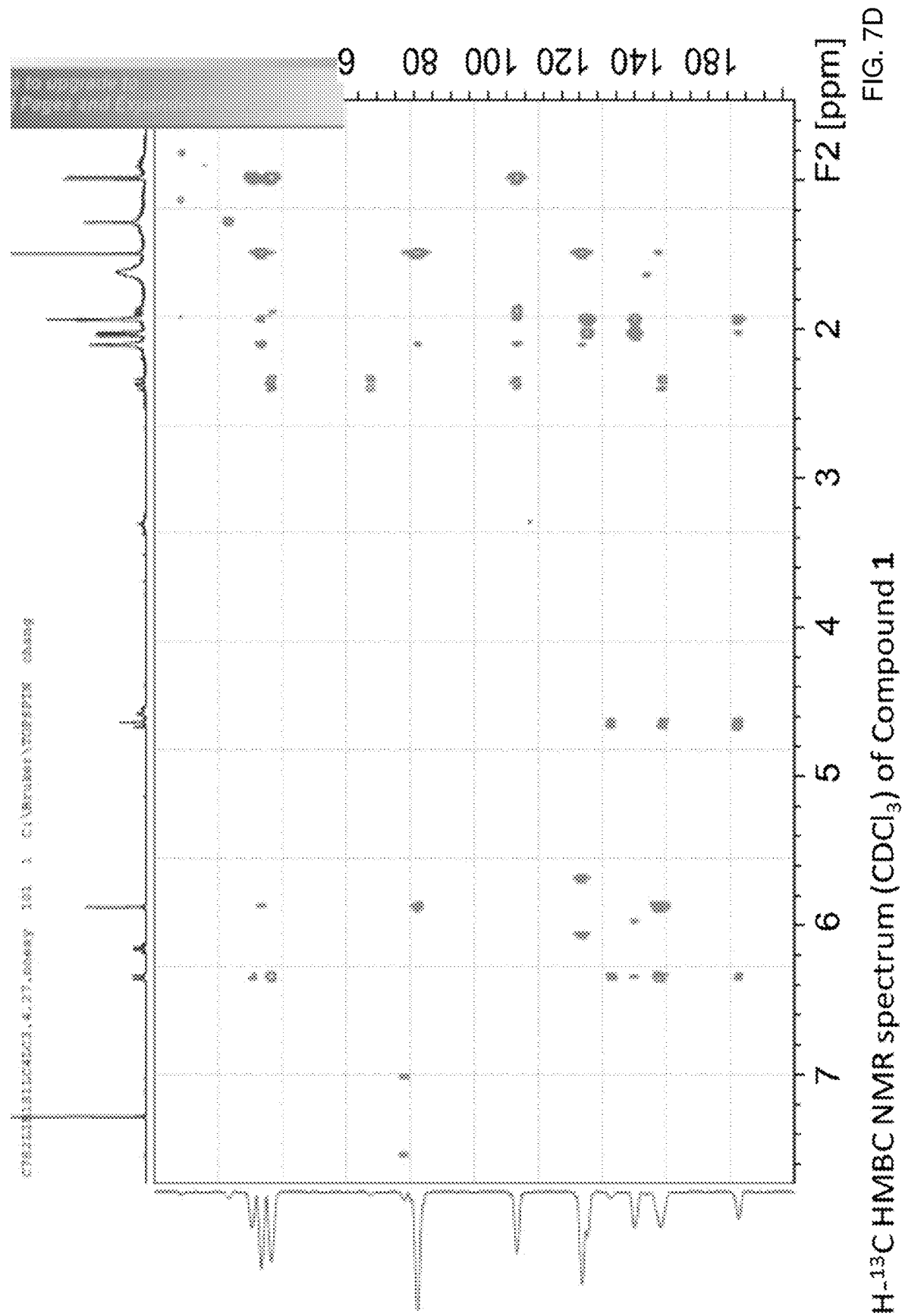
FIG. 7D $^1H$-$^{13}C$ HMBC NMR spectrum ($CDCl_3$) of Compound 1

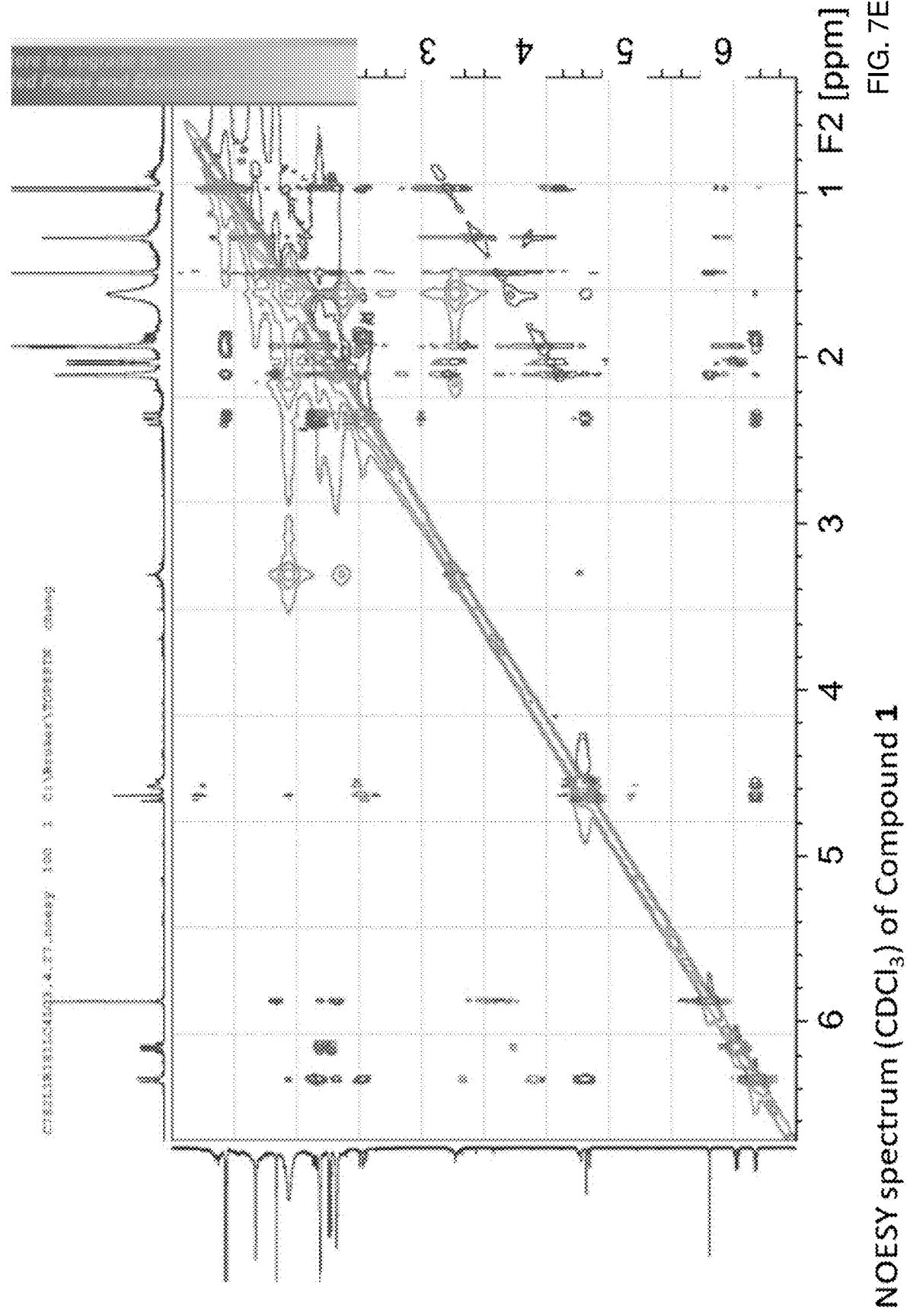
FIG. 7E NOESY spectrum (CDCl$_3$) of Compound 1

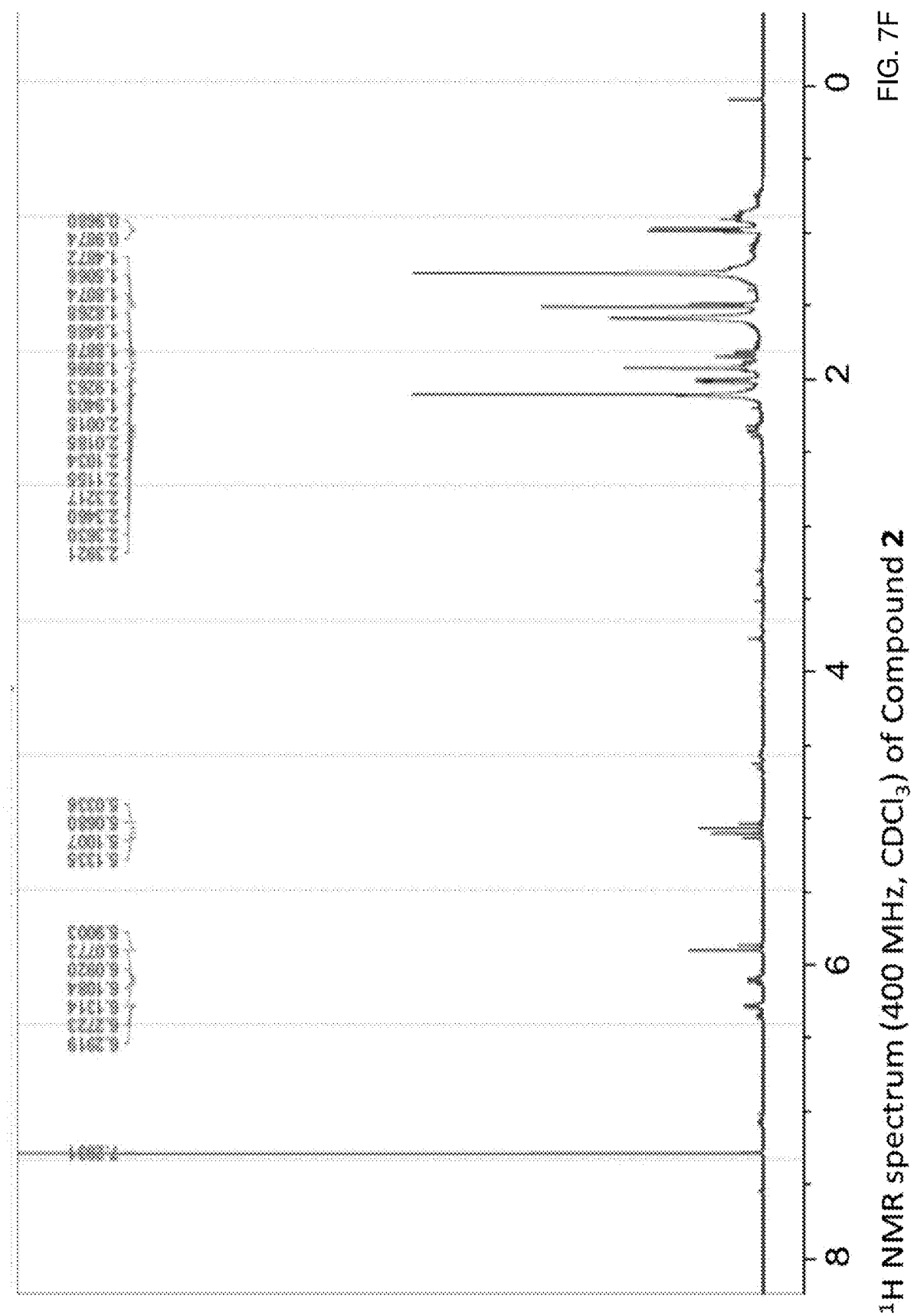

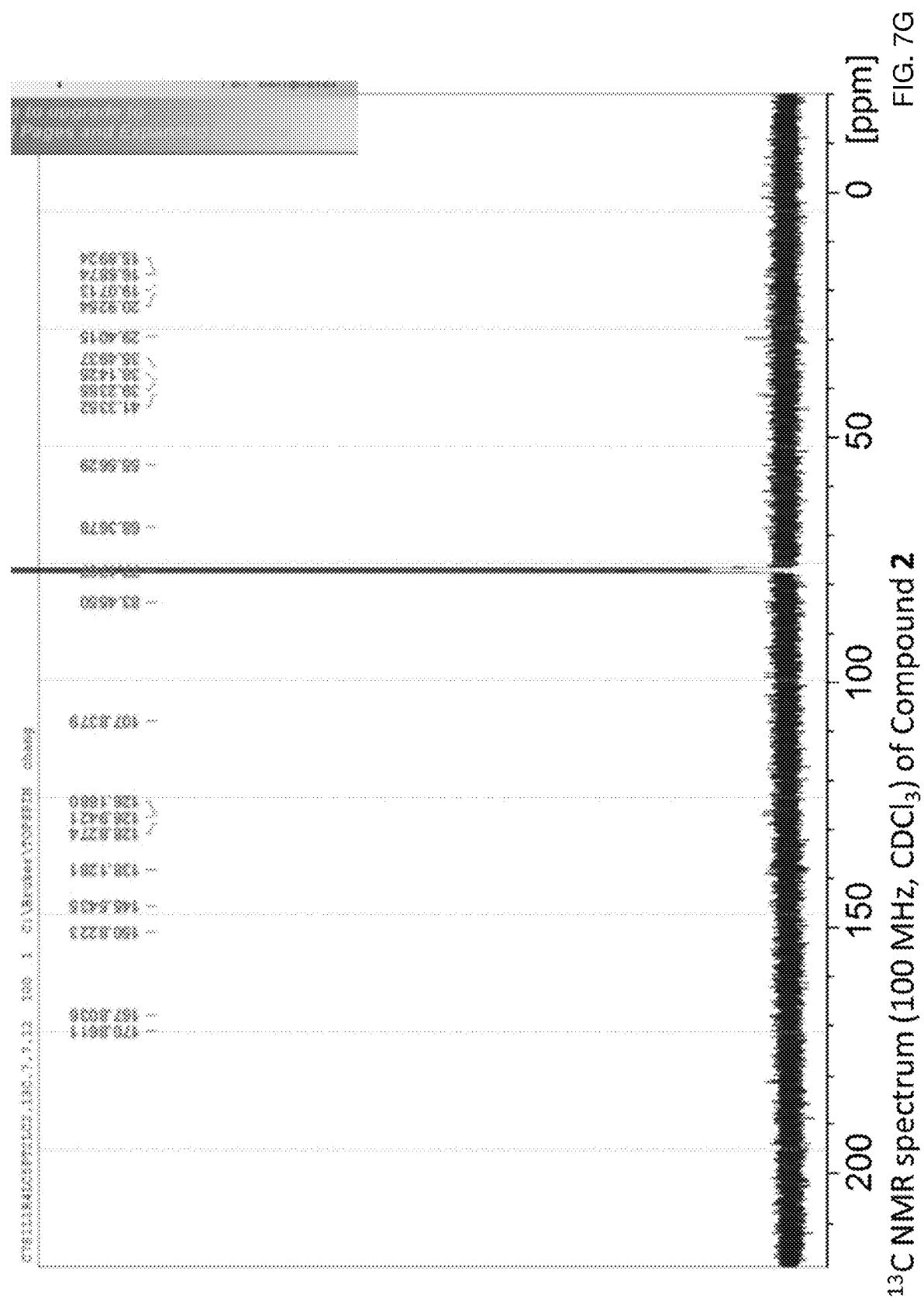

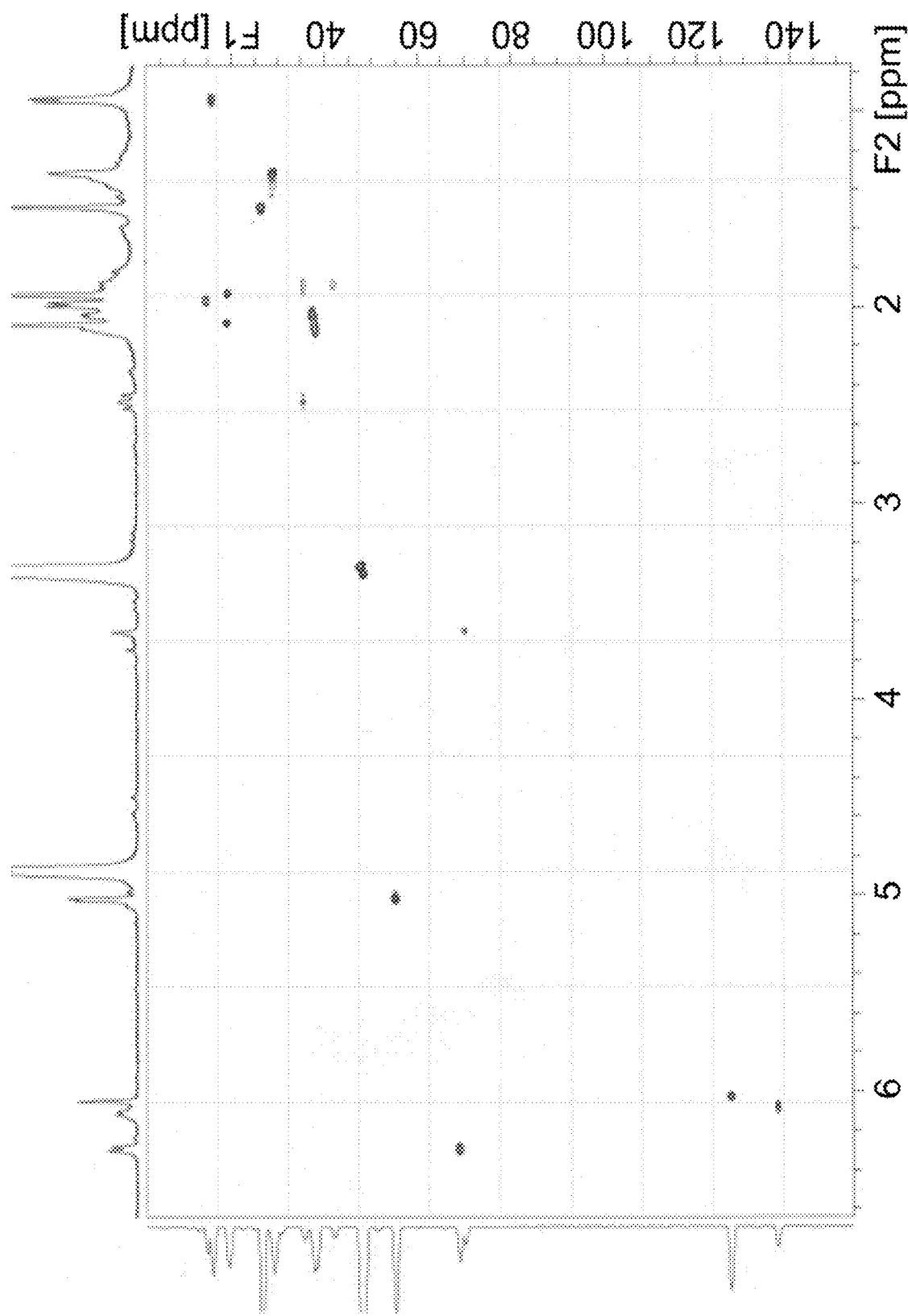

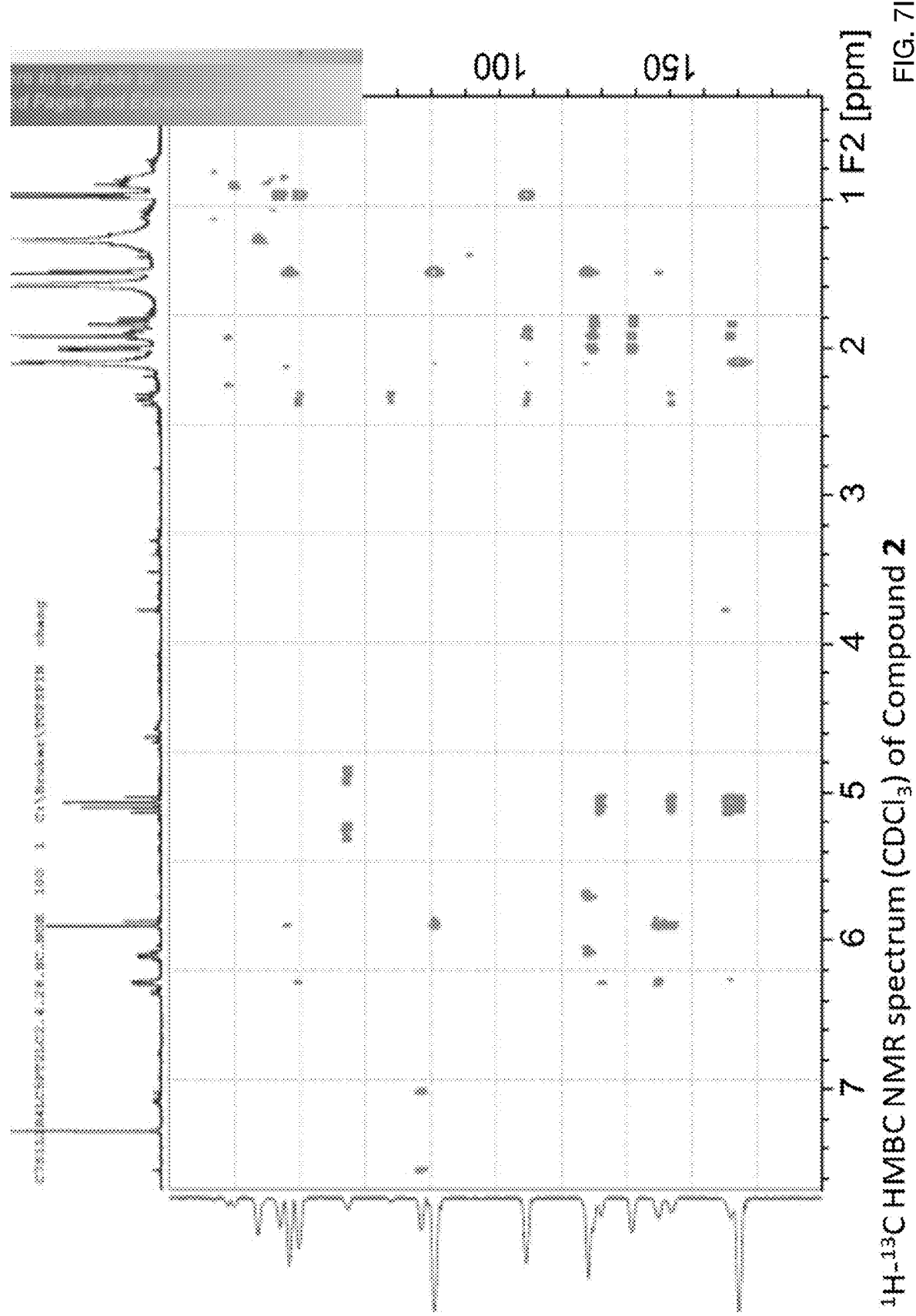
FIG. 7I $^1$H-$^{13}$C HMBC NMR spectrum (CDCl$_3$) of Compound 2

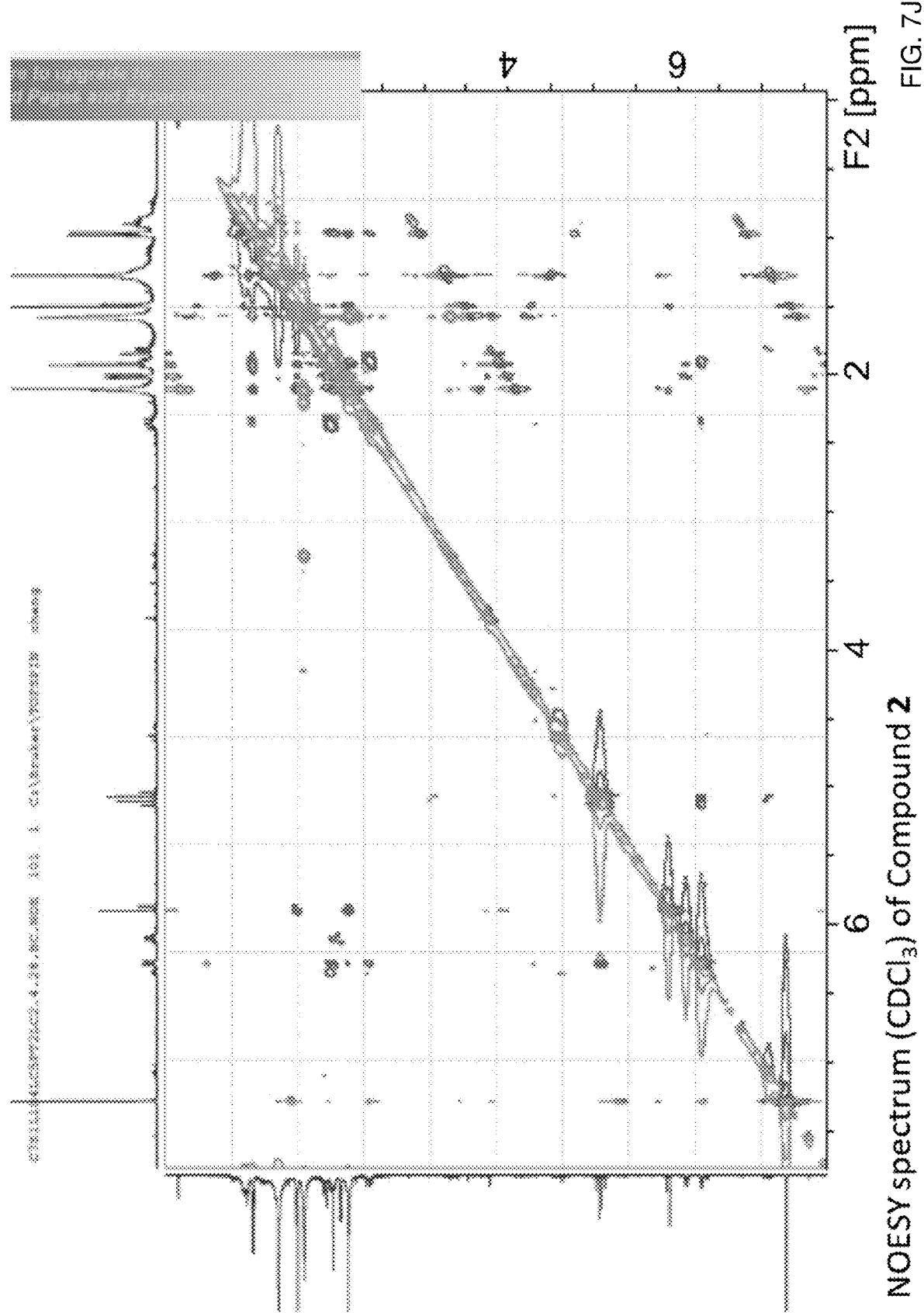
FIG. 7J NOESY spectrum (CDCl₃) of Compound 2

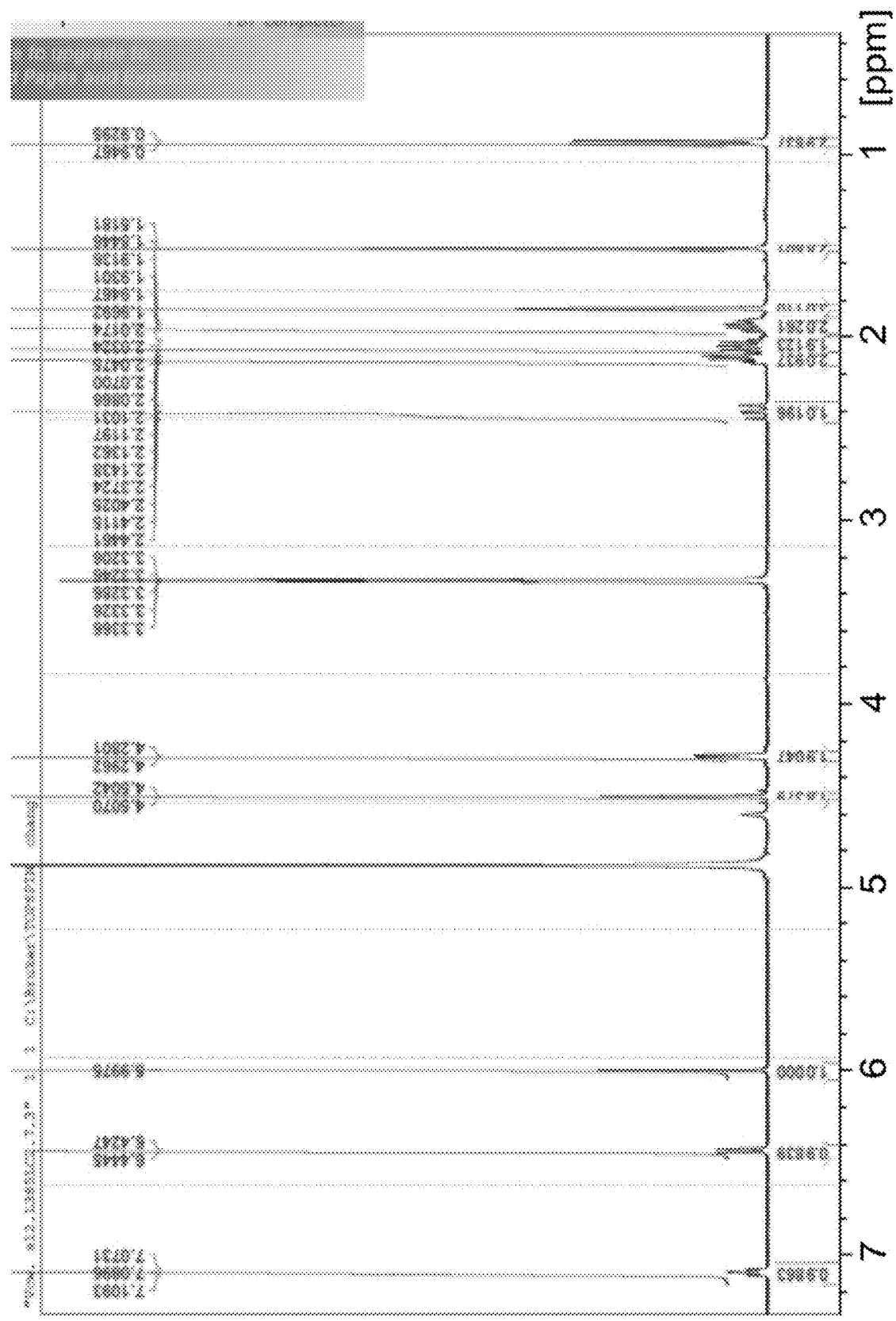

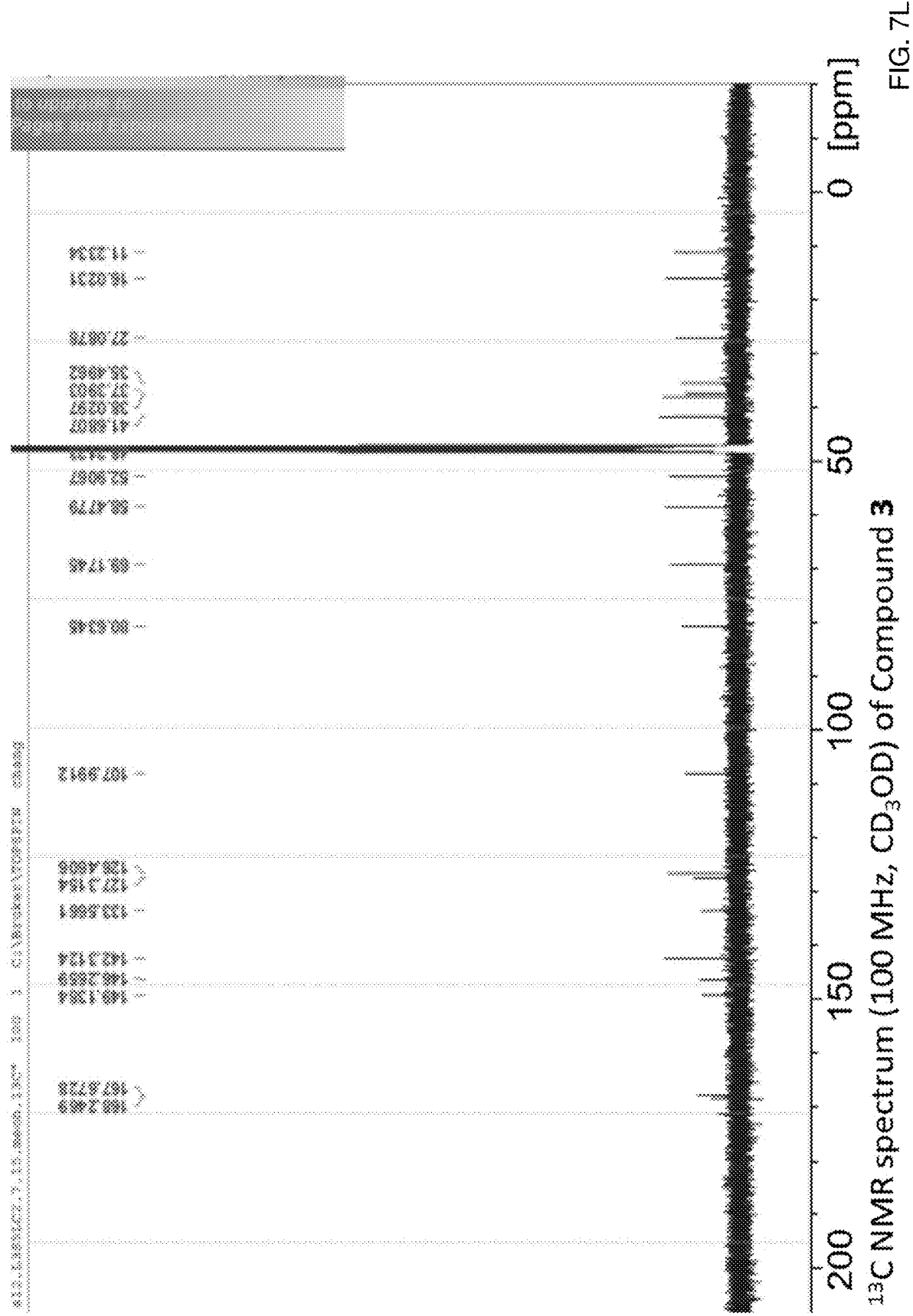

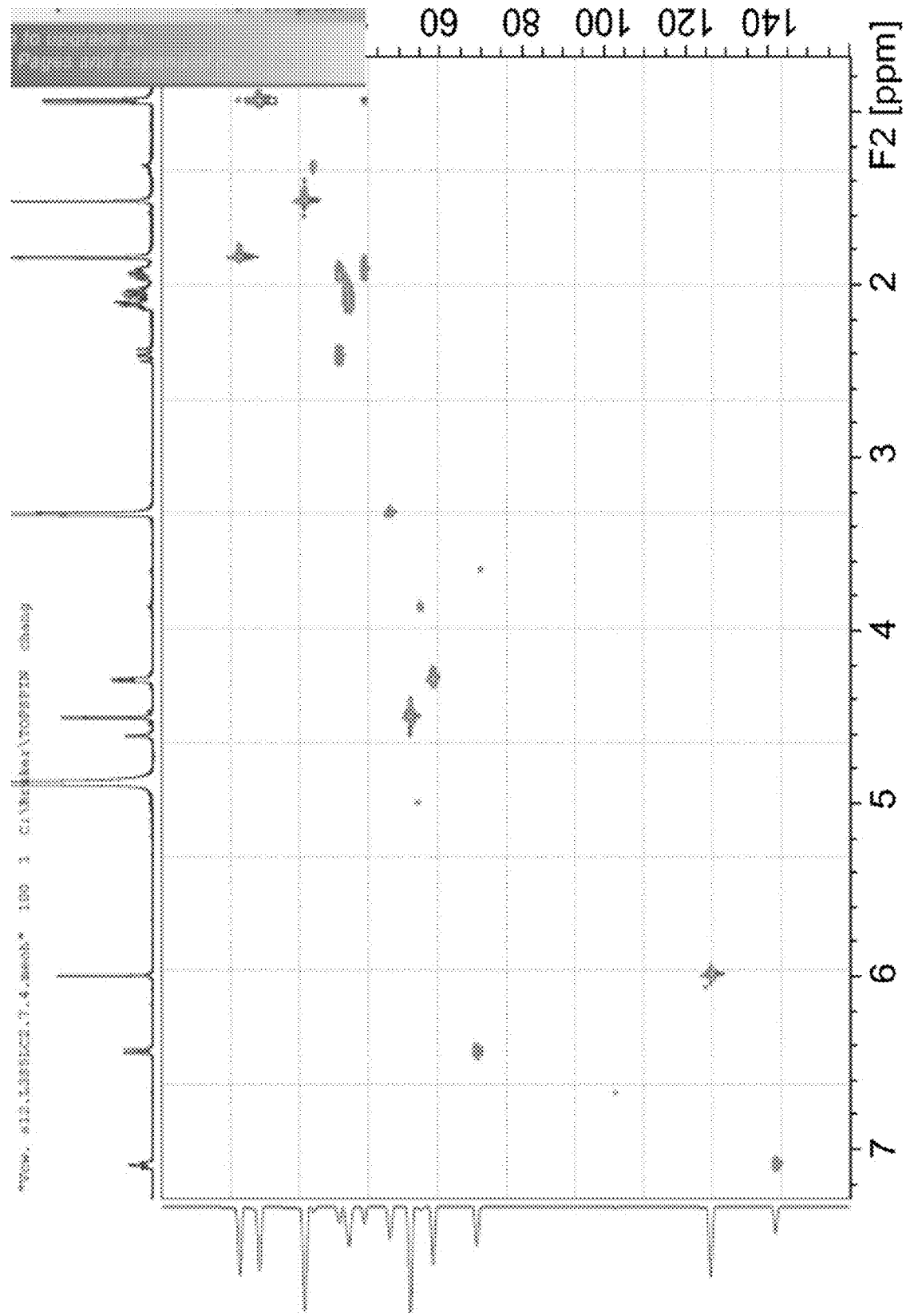
FIG. 7M ¹H-¹³C HSQC NMR spectrum (CD₃OD) of Compound 3

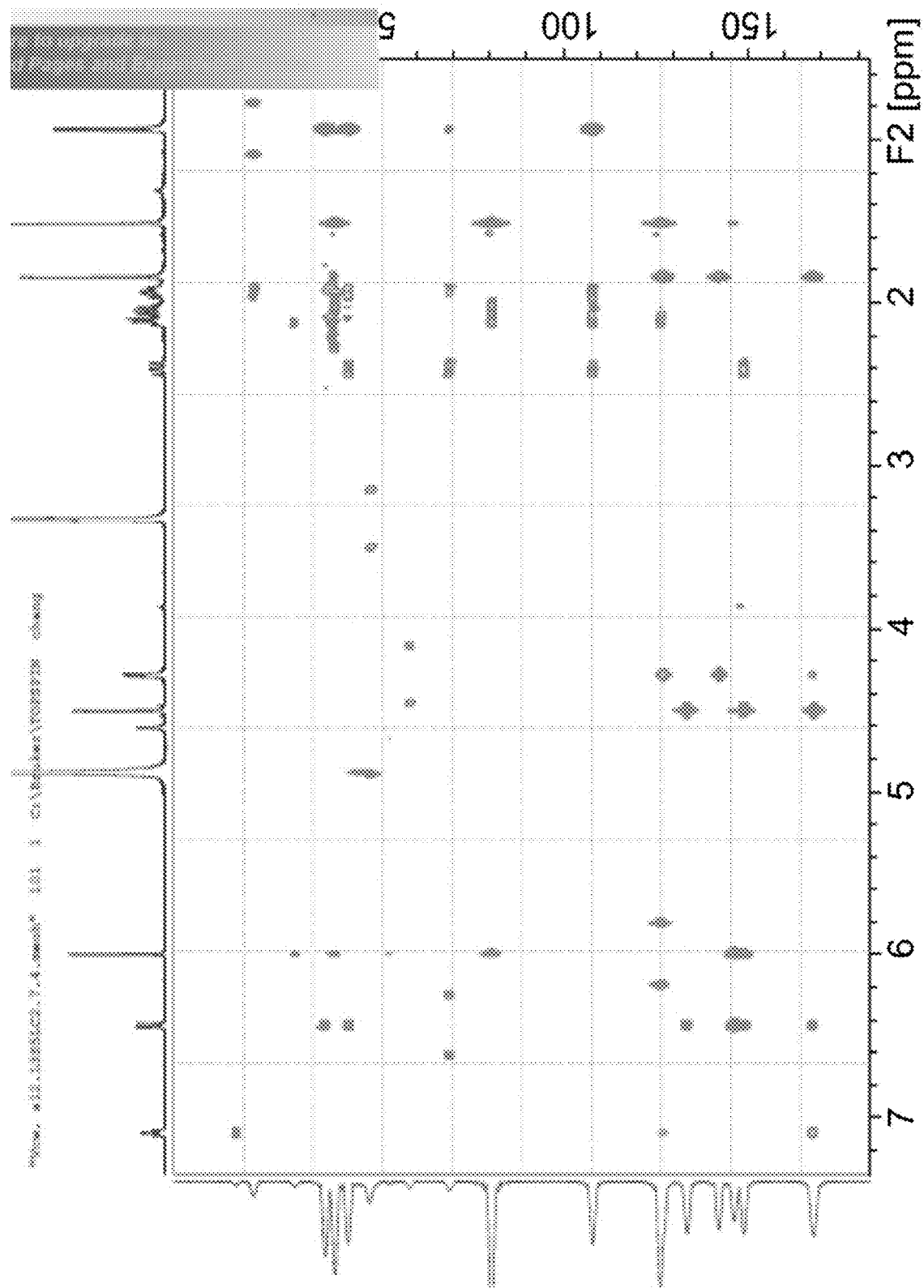
FIG. 7N $^1$H-$^{13}$C HMBC NMR spectrum (CD$_3$OD) of Compound 3

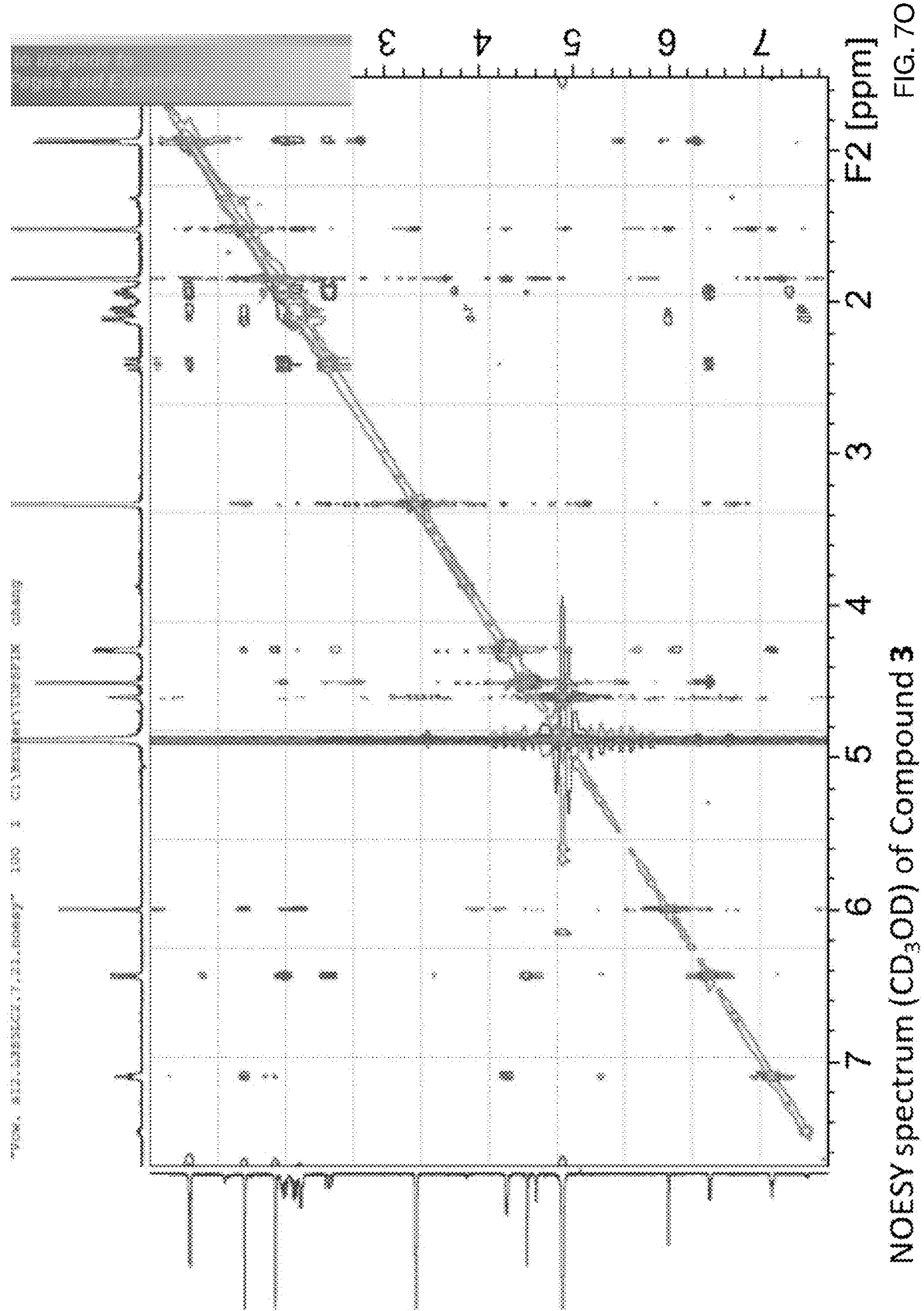
FIG. 7O NOESY spectrum (CD$_3$OD) of Compound 3

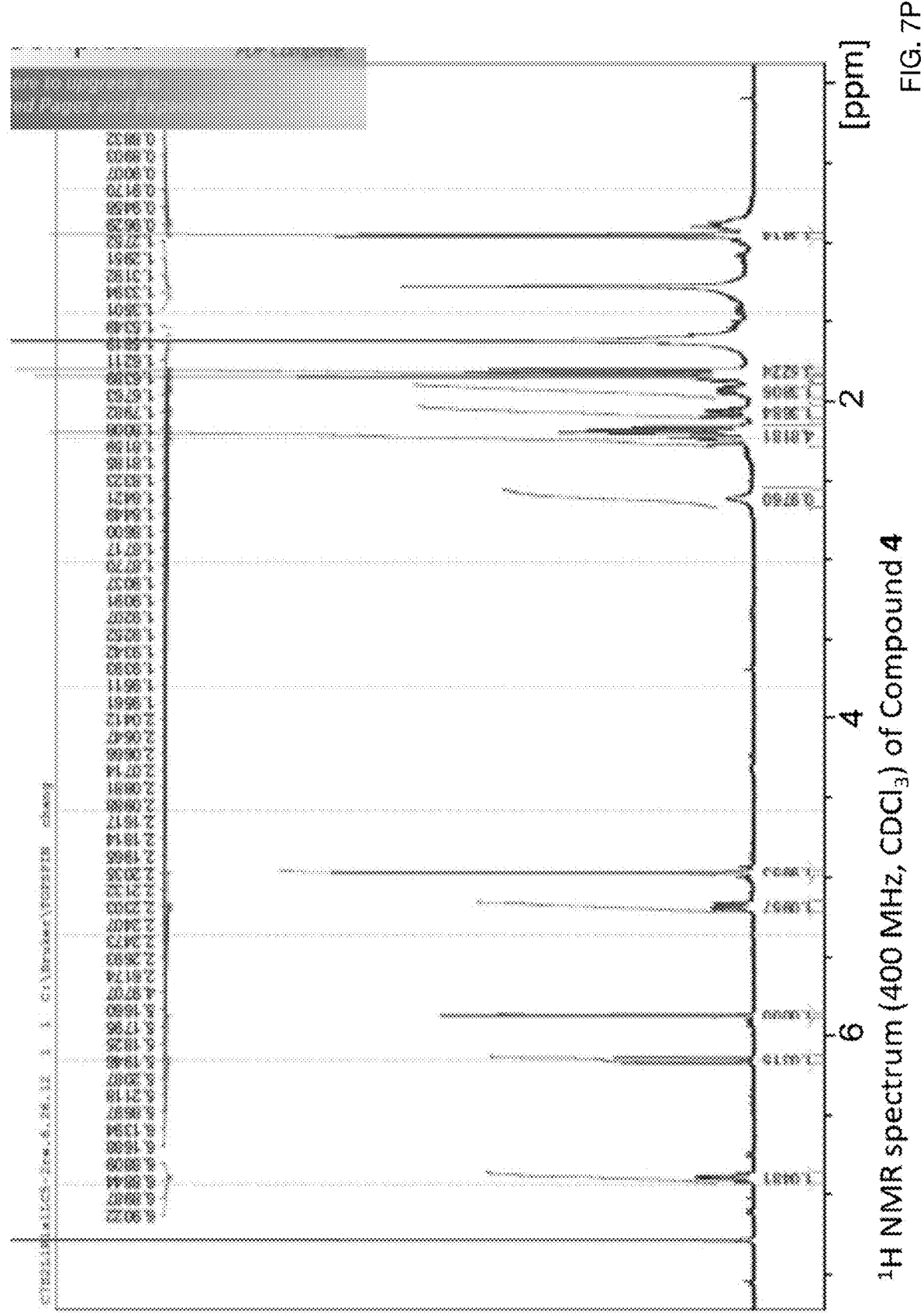
FIG. 7P $^1$H NMR spectrum (400 MHz, CDCl$_3$) of Compound 4

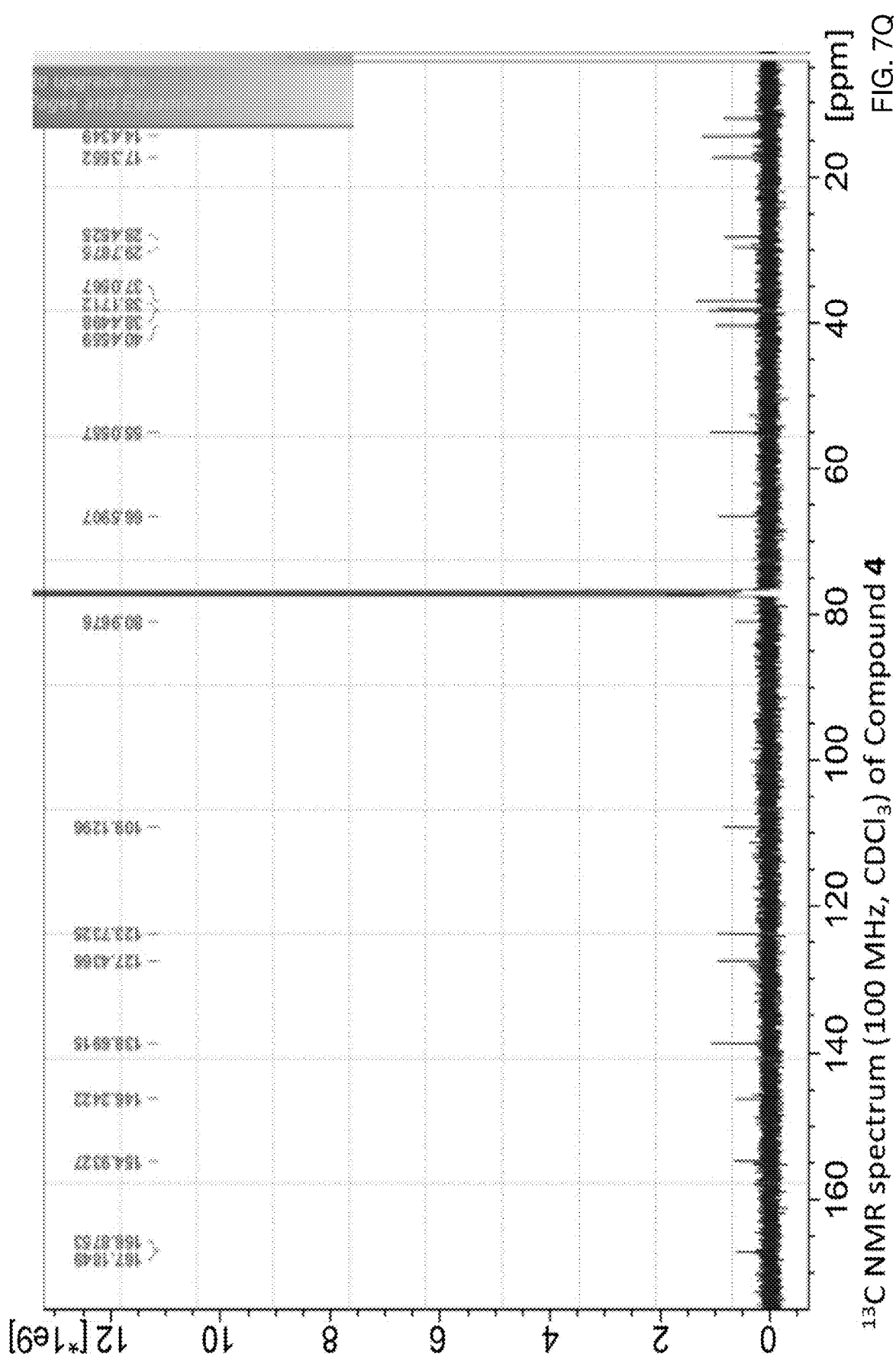

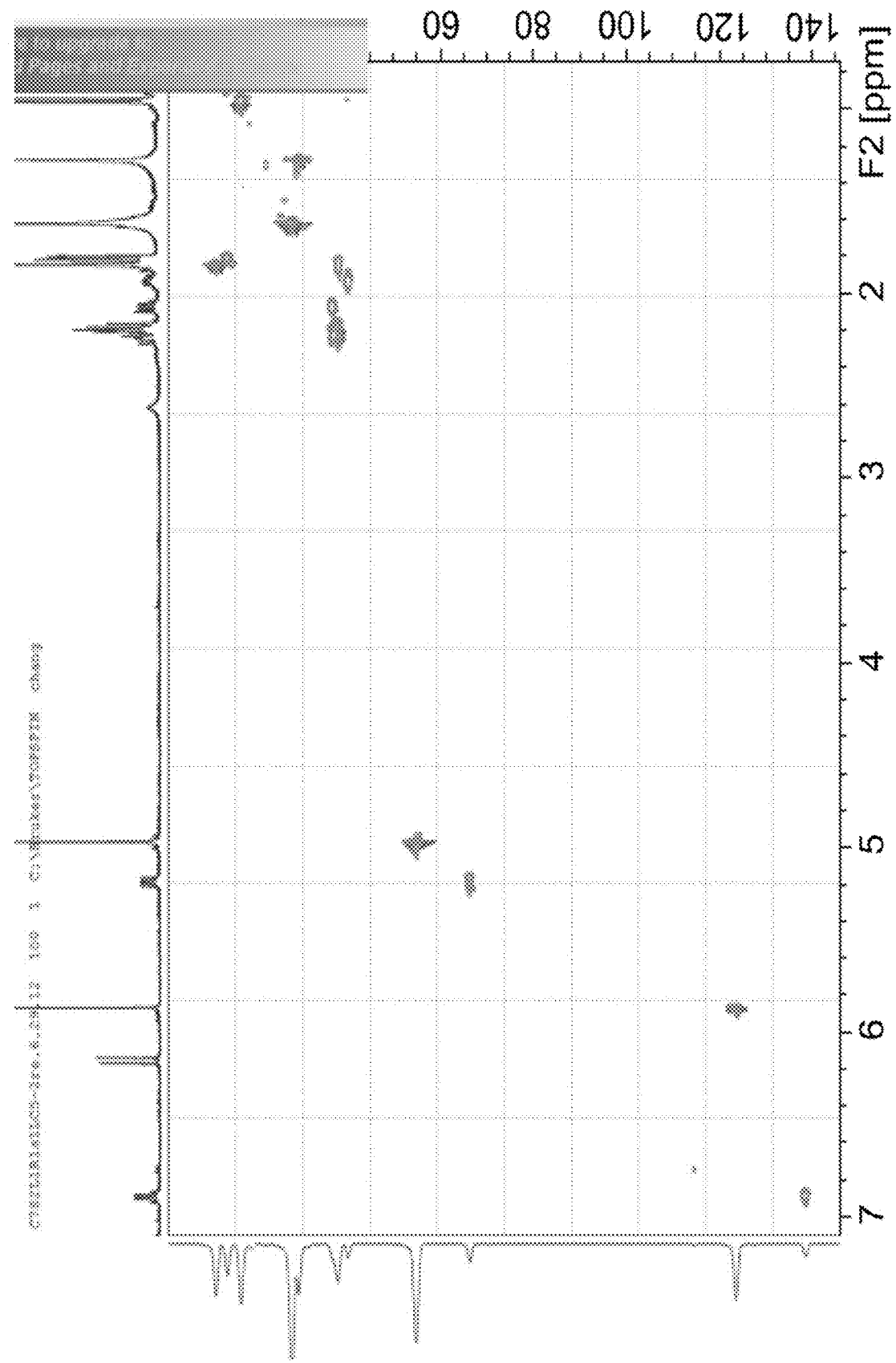
FIG. 7R $^1$H-$^{13}$C HSQC NMR spectrum (CDCl$_3$) of Compound 4

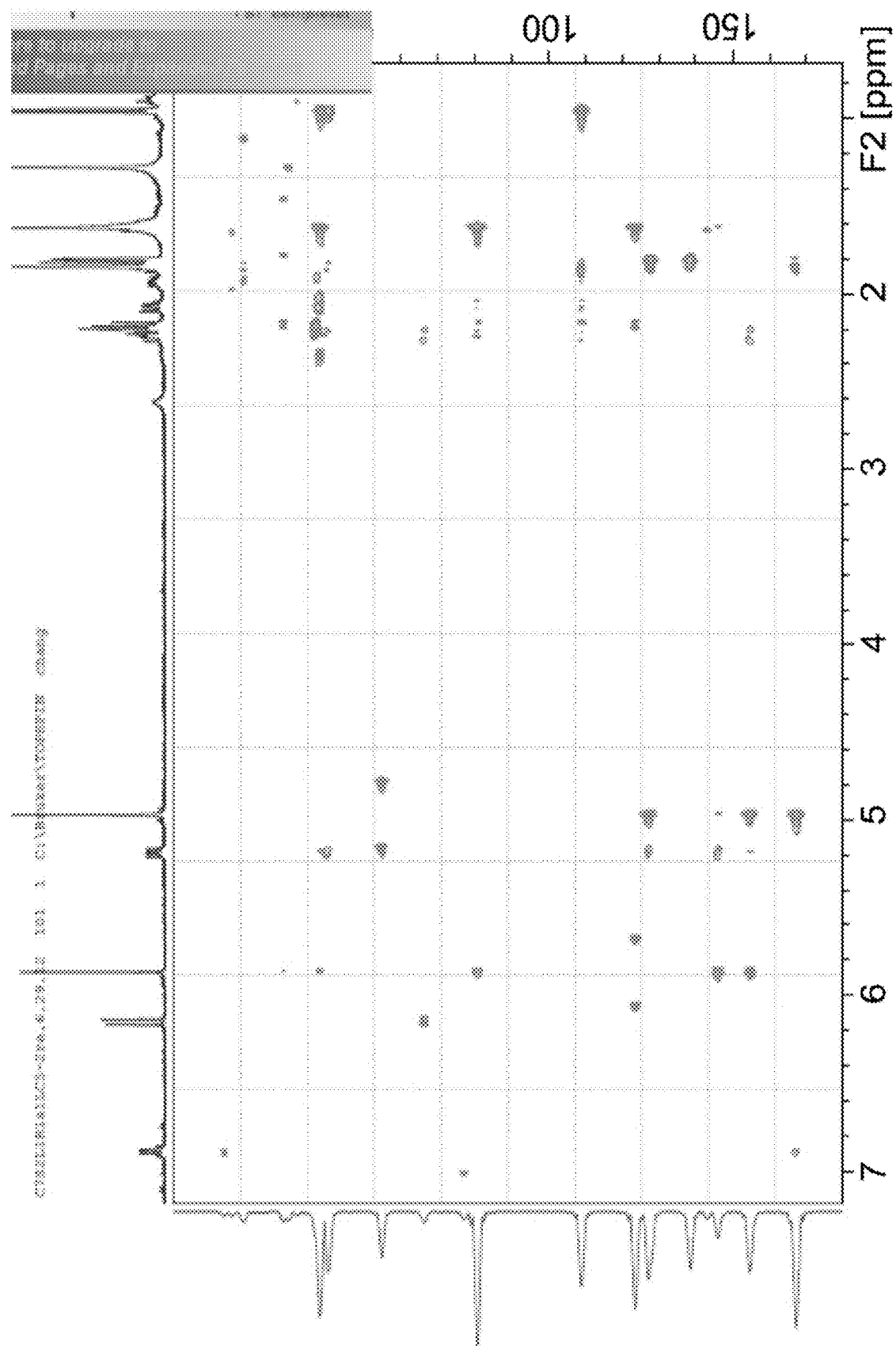
FIG. 7S $^1$H-$^{13}$C HMBC NMR spectrum (CDCl$_3$) of Compound 4

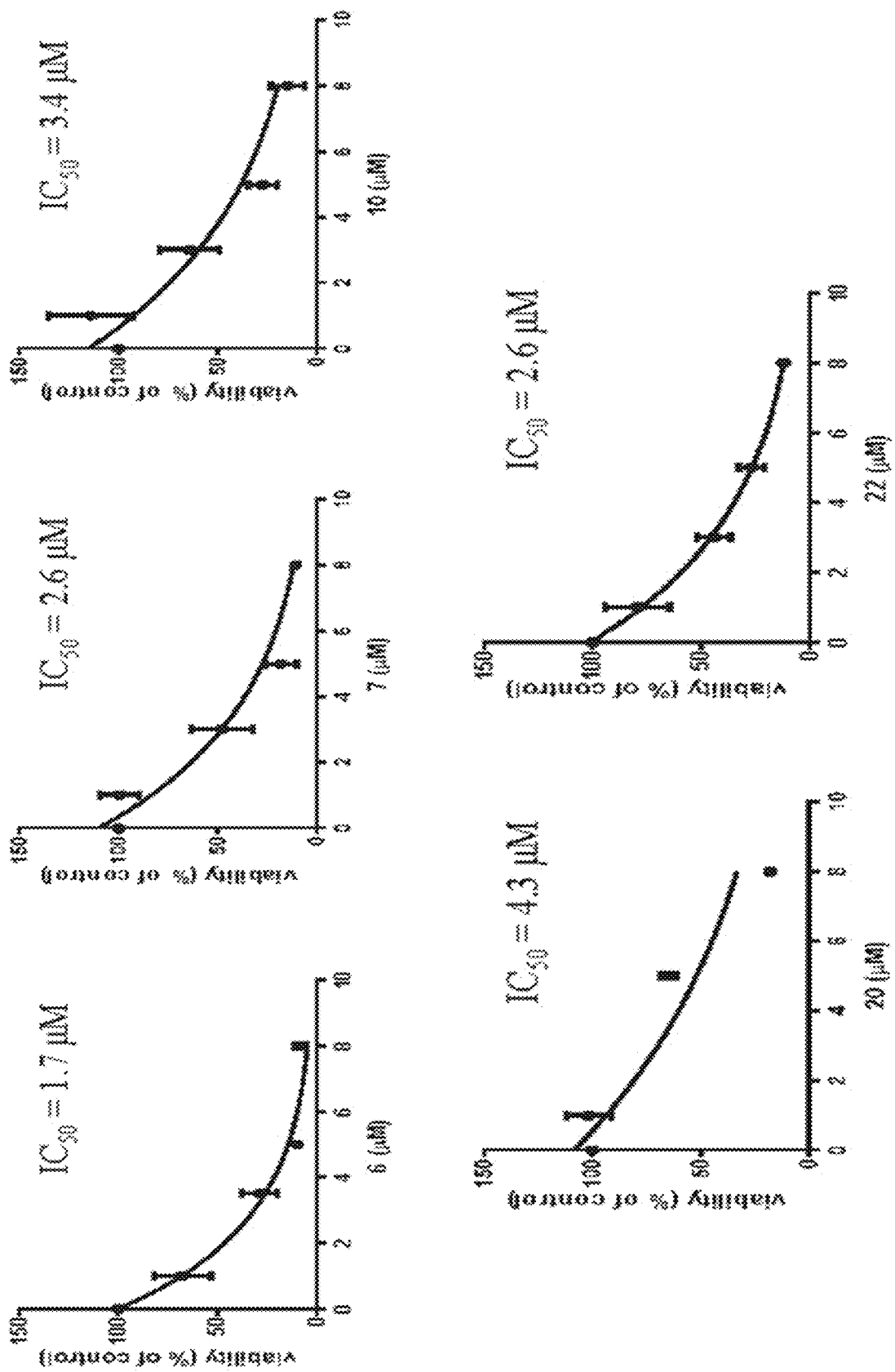
FIG. 9 A) U251MG cells

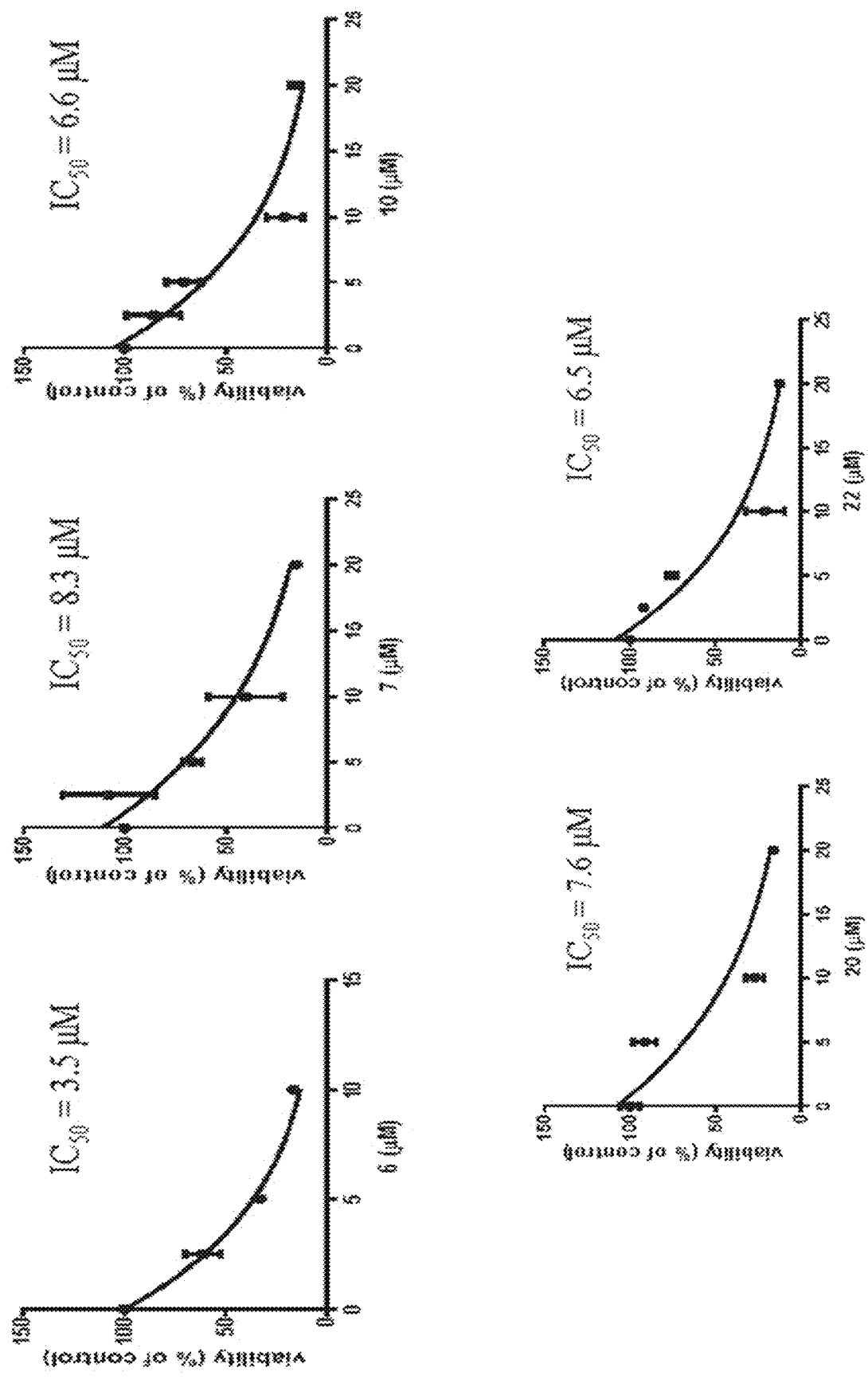

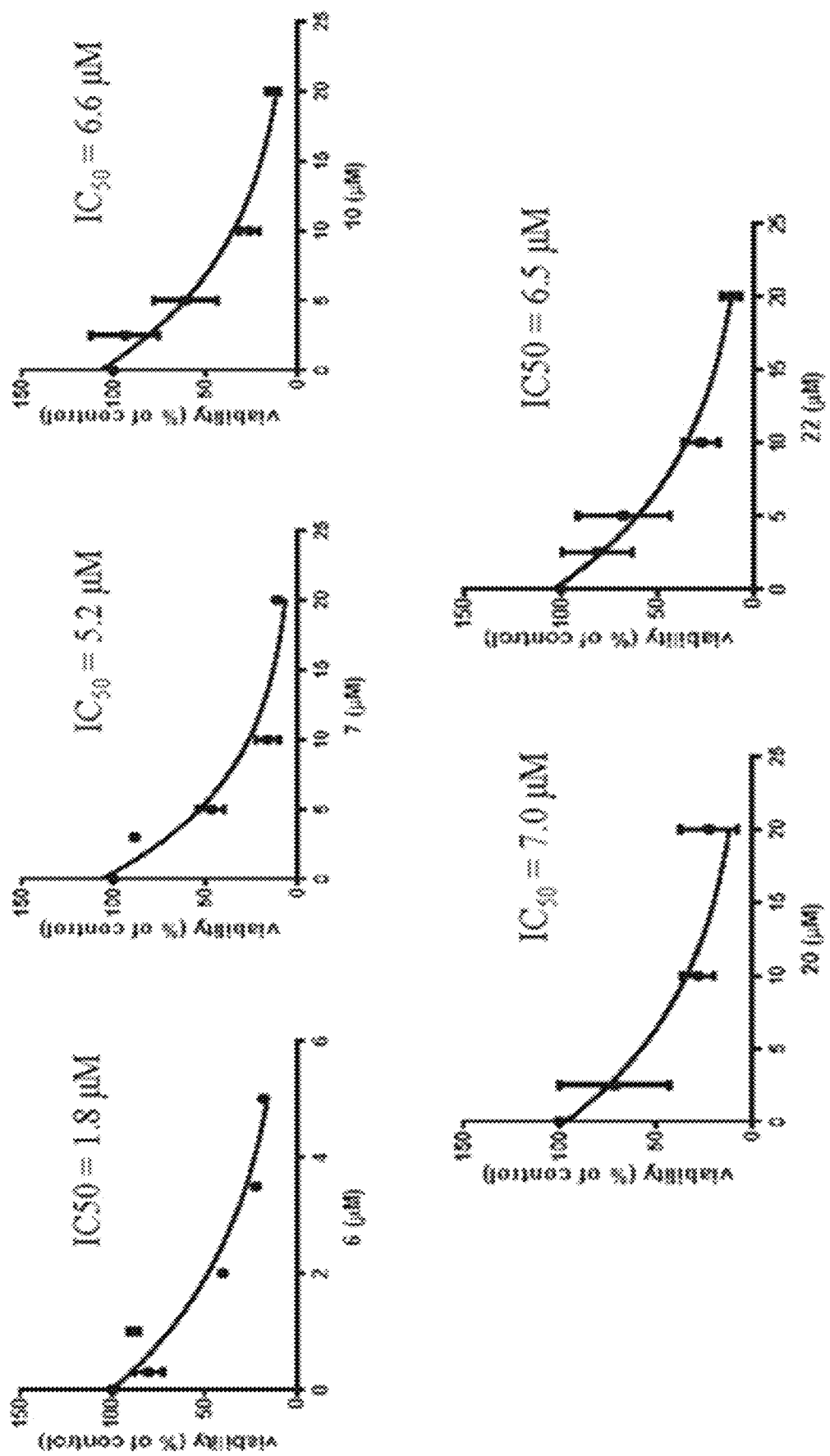
FIG. 9 C) MDA-MB-231 cells

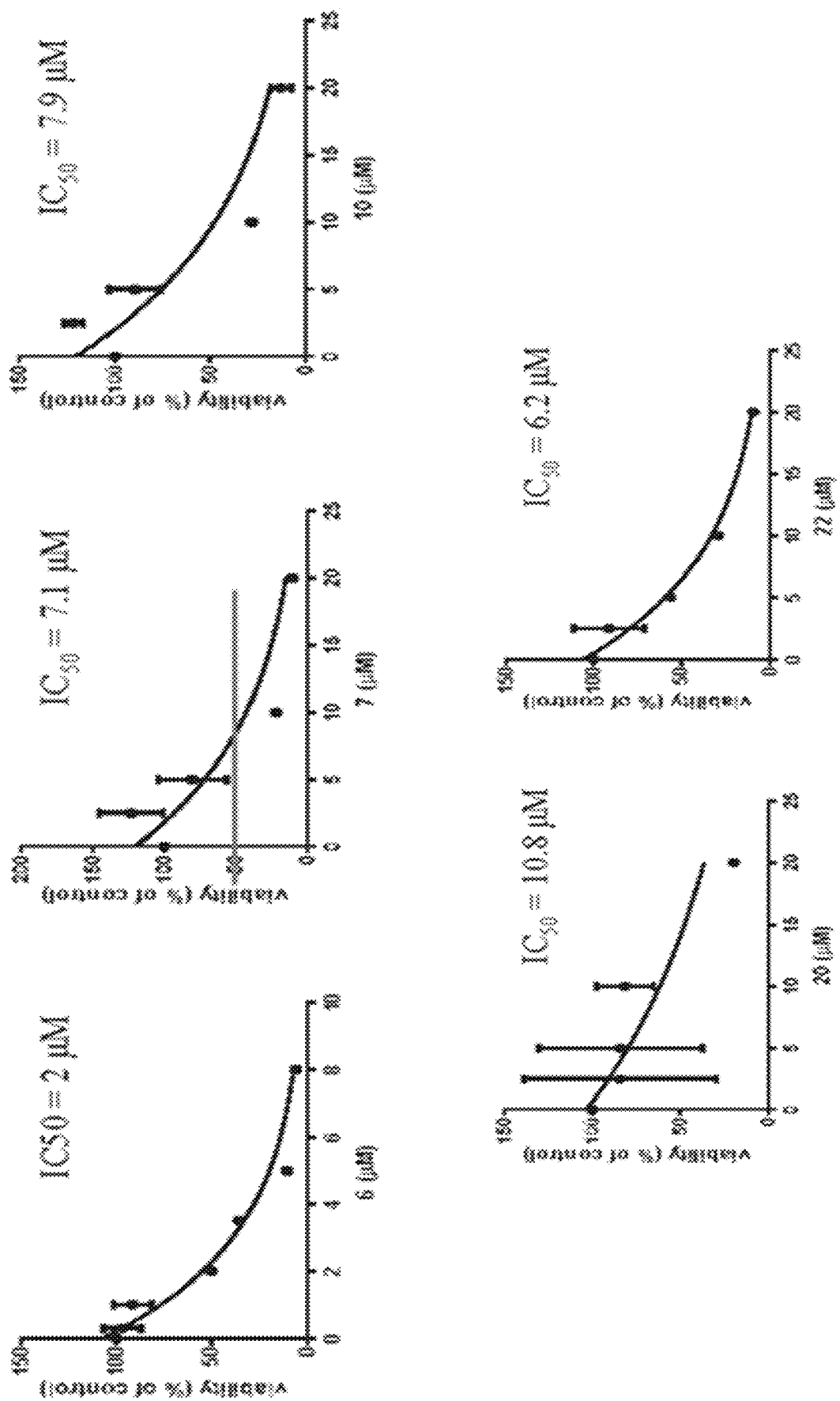
FIG. 9 D) NIH3T3 cells

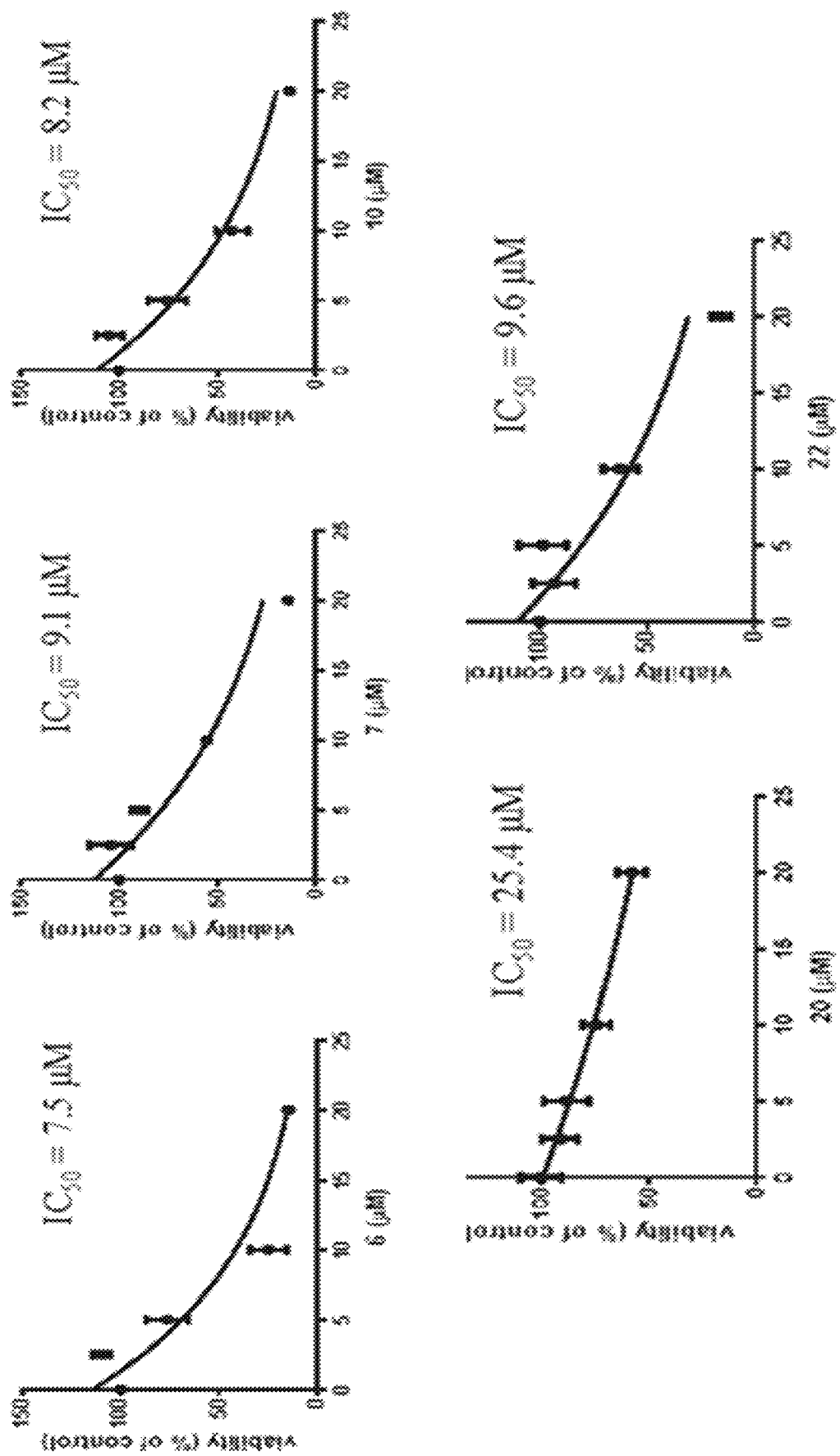

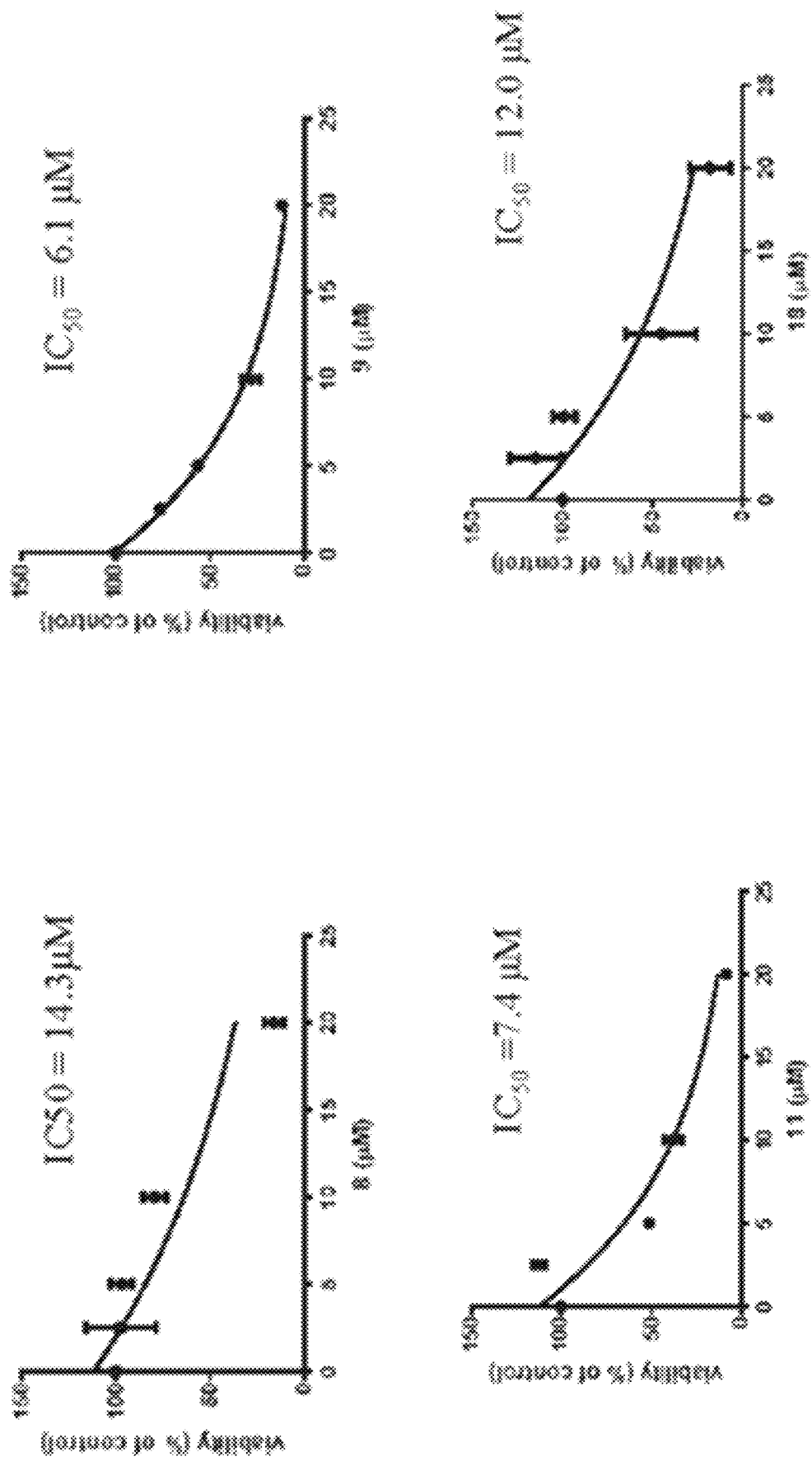
FIG. 9 F) Effects of weakly-active compounds against U251 MG cells

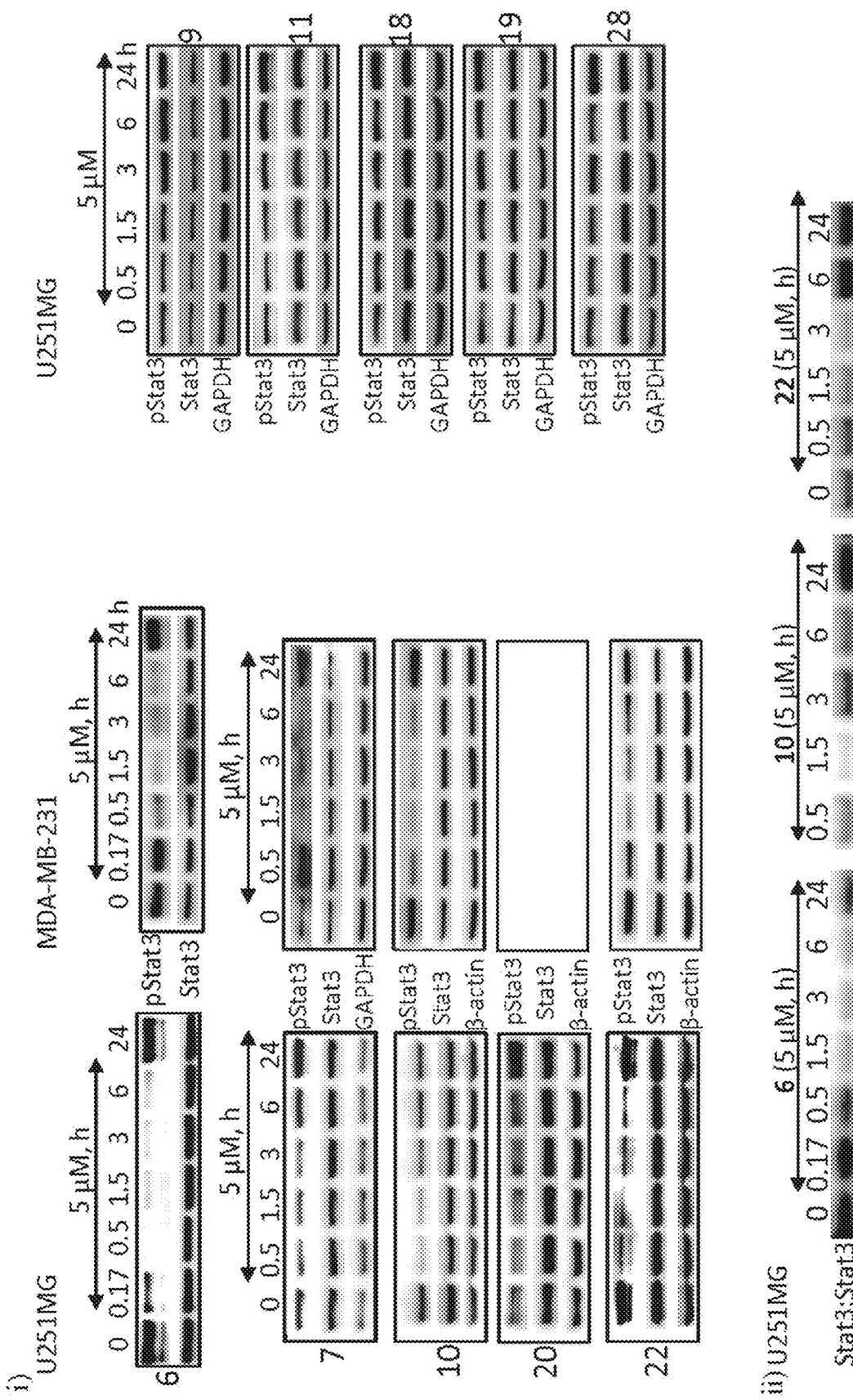

C) U251MG

D) Inhibition of STAT3 phosphorylation i) Bio-active compounds ii) Inactive compounds A) NIH3T3/hEGFR
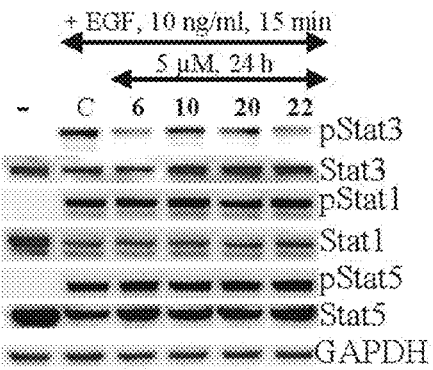
B) U251MG
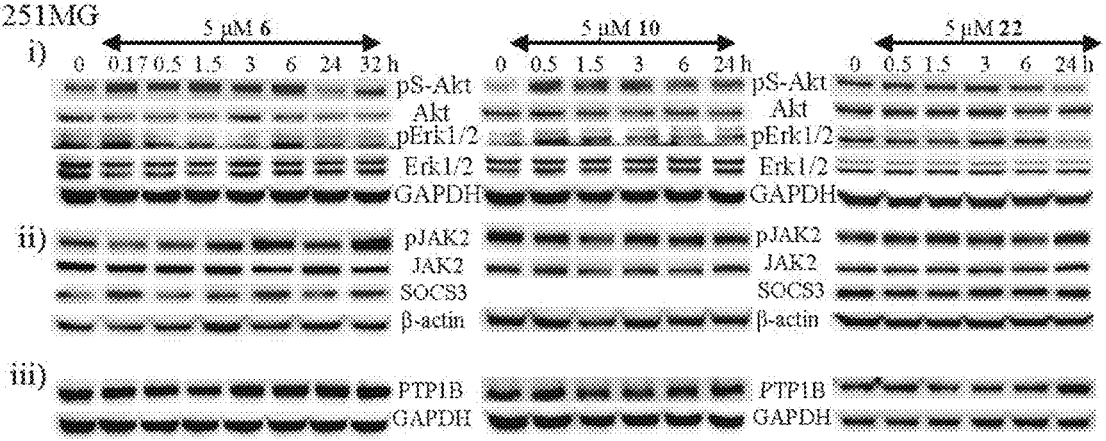
C) U251MG
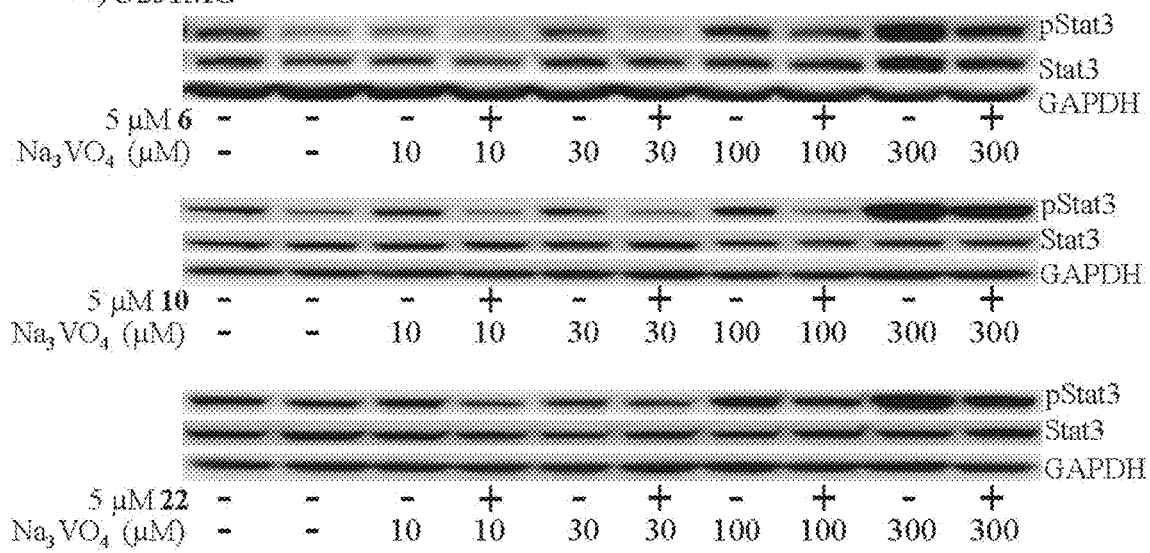
FIG. 13

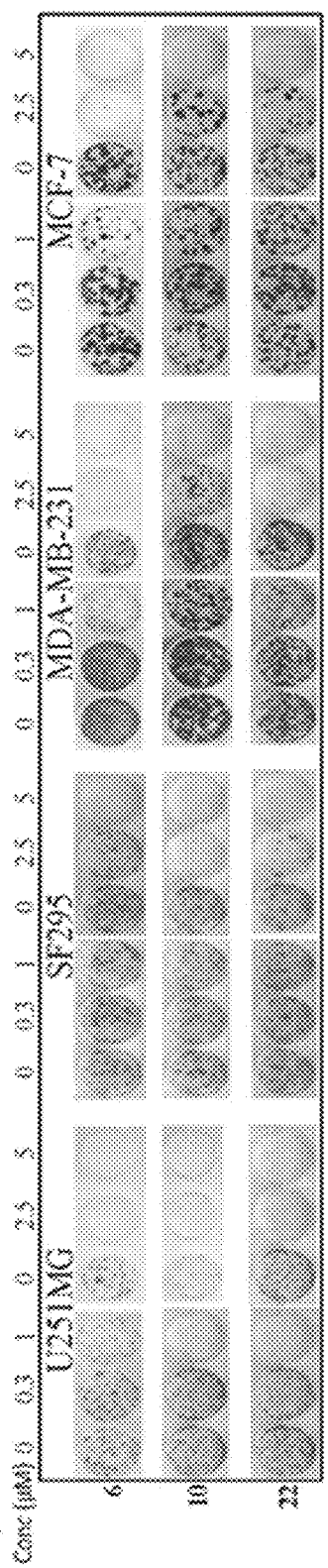
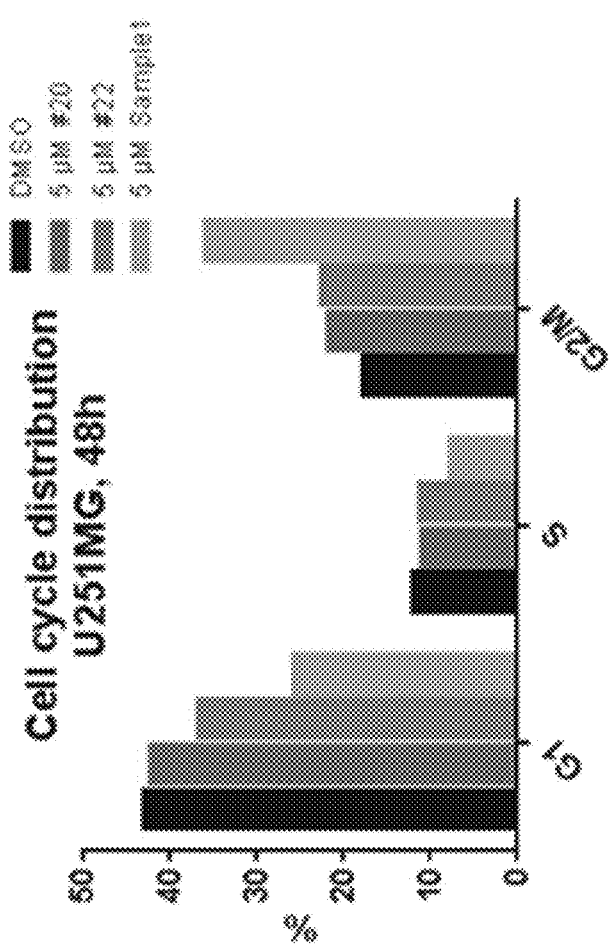
FIG. 17 A)
FIG. 17 B)

SESQUITERPENOID STAT3 INHIBITORS

RELATED APPLICATIONS

This application is a U.S. § 371 National Phase Application of International Application Number PCT/US2014/043523, filed on Jun. 20, 2014, which claims the benefit of priority to U.S. Provisional Patent Application No. 61/837,575, filed on Jun. 20, 2013. The contents of which are each incorporated by reference herein in their entireties.

GOVERNMENT RIGHTS

This invention was made with government support under grant numbers R01 CA128865, R01 CA161931, and P20 RR016467 awarded by the National Institutes of Health. The government has certain rights in the invention.

FIELD

The present disclosure is generally related to novel, potent and selective STAT3 inhibitors of Formula I and pharmaceutically acceptable salts thereof. The present disclosure also relates to pharmaceutical compositions containing the inhibitors and their use in the treatment or prevention of cancer, and other pathogenic conditions in which STAT-3 activation is implicated. As an example, the disclosure provides methods and compositions for the treatment of cancer by modulating STAT-3.

BACKGROUND

The following includes information that may be useful in understanding various aspects and embodiments of the present disclosure. It is not an admission that any of the information provided herein is prior art or relevant to the presently described or claimed inventions, or that any publication or document that is specifically or implicitly referenced is prior art.

The signal transducer and activator of transcription (STAT) proteins are a family of cytoplasmic transcription factors that mediate cellular responses to growth factors and cytokines, including promoting proliferation, differentiation, survival, development and inflammation (Bromberg, J., Signal transducers and activators of transcription as regulators of growth, apoptosis and breast development, Breast Cancer Res., 2000, 2(2): 86-90; Darnell, J. E., Jr., STATs and gene regulation, Science, 1997, 277: 1630-1635). Classical STAT activation is transient in keeping with cellular requirements and is initiated by phosphorylation on a critical tyrosine residue (Tyr705) by Janus kinase (JAKs), growth factor receptor or Src family Tyr kinases. Phosphorylation induces the formation of STAT:STAT dimers through a reciprocal pTyr-SH2 domain interaction, which then translocate to the nucleus and bind to specific DNA-response elements in target gene promoters and induce gene transcription.

By contrast, constitutively-active STAT3, a member of the STAT family, is prevalent in glioblastoma multiforme (GBM), breast cancer and many other human cancers and supports malignant development and progression. (Cattaneo, E., et al., Variations in the levels of the JAK/STAT and ShcA proteins in human brain tumors. Anticancer Res., 1998, 18: p. 2381-2387; Yu, H. and R. Jove, The STATS of Cancer-New molecular targets come of age. Nat. Rev. Cancer, 2004, 4: p. 97-105). Mechanisms by which constitutively-active STAT3 promotes tumor progression include the dysregulation of gene expression that leads to uncontrolled growth and survival of cells, enhanced tumor angiogenesis, and tumor metastasis. (Yu, H. supra; Bromberg, J. and J. E. Darnell, Jr., The role of STATs in transcriptional control and their impact on cellular function, Oncogene, 2000, 19: p. 2468-2473; Bowman, T., et al., STATs in oncogenesis, Oncogene, 2000, 19: p. 2474-2488; Turkson, J. and R. Jove, STAT proteins: novel molecular targets for cancer drug discovery, Oncogene, 2000, 19: p. 6613-6626; Turkson, J., STAT proteins as novel targets for cancer drug discovery, Expert Opin Ther Targets, 2004, 8(5): p. 409-422; Miklossy, G., T. S. Hilliard, and J. Turkson, Therapeutic modulators of STAT signaling for human diseases, Nat Rev Drug Discov, 2013, 12: p. 611-629). STAT3 activity further represses tumor immune surveillance. (Wang, T., et al., Regulation of the innate and adaptive immune responses by STAT-3 signaling in tumor cells, Nat Med, 2004, 10(1): p. 48-54). Evidence further shows cross-talk between STAT3 and other key proteins, such as NF-B represent an important component of the STAT3-dependent mechanisms for promoting malignant progression. (Yu, H., D. Pardoll, and R. Jove, STATs in cancer inflammation and immunity: a leading role for STAT3, Nat Rev Cancer, 2009, 9: p. 798-809; Grivennikov, S. I. and M. Karin, Dangerous liaisons: STAT3 and NF-kB collaboration and crosstalk in cancer, Cytokine & Growth Factor Reviews, 2010, 21: p. 11-19). Furthermore, STAT3 activity independent of its Tyr phosphorylation has recently been shown to modulate the biochemical processes of the mitochondria that in turn drives malignant transformation in specific contexts.

SUMMARY OF THE INVENTION

This invention relates in one aspect to a method for the purification of novel products derived from *Vernonia cinerea* (Vc). In another aspect, this invention relates to synthetic derivatives of the purified products. In still another aspect, this invention relates to methods of treatment using these compounds.

In one aspect, this invention relates to compounds of Formula I:

Formula I

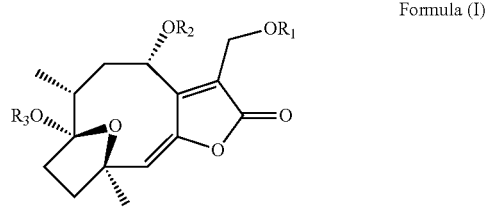

Formula (I)

In one aspect, $R_1$ is selected from the group consisting of H or methyl ($CH_3$), 4-hydroxytigloyl, tigoyl, 2-methylacryloyl, acryloyl, acetyl, proponyl, butanyl, pentanyl, hexanyl, amide, cinnamyl, triazoles, substituted triazoles, (3-(4-(trifluoromethyl)phenyl)acryl, 3-(4-fluorophenyl)acryl, 3,7-dimethylocta-2,6-dienyl, 3-methylbut-2-enyl, 3,7-dimethyloct-6-enyl, 2-methylbut-2-enyl, 2-methylbut-2-enyl, substituted or unsubstituted $C_1$-$C_4$alkyl, substituted or unsubstituted $C_1$-$C_9$heteroalkyl, isodecenyl, isopentenyl, $C_1$-$C_9$alkoxyalkyl, $C_1$-$C_9$alkylaminoalkyl, substituted or unsubstituted $C_3$-$C_6$cycloalkyl, substituted or unsubstituted aryl, substituted or unsubstituted $C_2$-$C_8$heterocycloalkyl, substituted or unsubstituted heteroaryl, $C_1$-$C_9$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_9$heterocycloalkyl); $R_2$ is selected from the group consisting of H, 4-hydroxytigloyl, tigoyl, 2-methylacryloyl, acryloyl, amide, cinnamyl, triazoles, (3-(4-(trifluoromethyl)phenyl)acryl, 3-(4-fluorophenyl)acryl, 3,7-dimethylocta-2,6-dienyl, 3-methylbut-2-enyl, 3,7-dimethyloct-6-enyl, 2-methylbut-2-enyl, 2-methylbut-2-enyl, substituted triazoles, acetyl, proponyl, butanyl, pentanyl, hexanyl, methyl ($CH_3$), substituted or unsubstituted $C_1$-$C_9$alkyl, substituted or unsubstituted $C_1$-$C_9$alkenyl substituted or unsubstituted $C_1$-$C_4$heteroalkyl, isodecenyl, isopentenyl, $C_1$-$C_9$alkoxyalkyl, $C_1$-$C_9$alkylaminoalkyl, substituted or unsubstituted $C_3$-$C_9$cycloalkyl, substituted or unsubstituted aryl, substituted or unsubstituted $C_2$-$C_9$heterocycloalkyl, substituted or unsubstituted heteroaryl, $C_1$-$C_4$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_9$heterocycloalkyl); $R_3$ is selected from the group consisting of H or methyl ($CH_3$) or acetyl; with the proviso that the compound of Formula I is not previously known. In some aspects, for example, $R_1$ is tigoyl, $R_2$ is acetyl, and $R_3$ is H. In another aspect, $R_1$ is 4-hydroxytigloyl, $R_2$ is acetyl, $R_3$ is H. In another embodiment, $R_1$ is 2-methylacryloyl, $R_2$ is acetyl, and $R_3$ is H. In some aspects, $R_1$, $R_2$, and $R_3$ may include or exclude any of the respective, recited species.

In one aspect, this invention relates to pharmaceutically active metabolites, or pharmaceutically acceptable solvates, pharmaceutically acceptable salts, or pharmaceutically acceptable prodrugs of the compounds of Formula I.

In one aspect, this invention relates to formulations comprising compounds of Formula I, which selectively inhibit STAT3.

In one aspect, this invention relates to the purified and/or synthetic hirsutinolides of this invention, including for example, compounds 6, 7, 10, 20 and 22 and the synthetic derivatives of 22, zmm-1-19, 1-20, 1-22, 1-36, 1-37, 1-72, 1-79, 1-80, and 1-82.

In one aspect, this invention relates to novel, selective and potent STAT3 inhibitors, useful as cancer therapeutics. In some aspects, the compounds of this invention are useful for inhibiting malignant transformation, tumor development and progression. In one aspect, for example, this invention relates to methods of treating cancer by administering the purified and/or synthetic hirsutinolides of this invention, including for example, the compounds of Formula I, for example, compounds 6, 7, 10, 20 and 22 and the synthetic derivatives of 22, zmm-1-19, 1-20, 1-22, 1-36, 1-37, 1-72, 1-79, 1-80, and 1-82, to suppress human glioma and breast cancer phenotypes in part by inhibiting aberrantly-active STAT3.

In one aspect, this disclosure relates to a method for synthesizing the compounds of Formula I where $R_3$ is H, $R_2$ is acetyl, and $R_3$ is 4-hydroxytigloyl, tigoyl, 2-methylacryloyl, acryloyl, cinnamyl, isodecenyl, or isopentenyl, comprising (a) first reacting the appropriate carboxylic acid with 2,4,6-trichlorobenzoyl chloride by esterification, such as the Yamaguchi esterification; and (b) reacting the resulting 2,4,6-trichlorobenzyl ester to compound 14 to yield the final compound. In alternative aspects, the 2,4,6-trichlorobenzyl ester can be reacted to compounds 8 or 17 to yield a different series of compounds. The appropriate carboxylic acid is, for example, the carboxylic acid that will yield the carbonyl component of each of the esters shown in FIG. 3.

In one aspect, this invention relates to formulations comprising compounds of FIGS. 2A-2B and/or FIG. 20, which selectively inhibit STAT3.

In one aspect, the invention relates to the inventors' design of STAT3 inhibitors which interfere with the dimerization between two monomers, and the inventors' recognition that this represents an attractive strategy to develop drugs that inhibit STAT3 activation and functions.

The present disclosure provides novel, selective STAT3 inhibitors, and pharmaceutical formulations and kits comprising the inhibitors. The compounds and pharmaceutical formulations are useful as therapeutics for cancer and other conditions mediated by aberrantly active STAT-3. In some aspects, the processes inhibited by the compounds and compositions of this invention include proliferation, survival, angiogenesis, migration/metastasis/invasion, and immunity.

In one aspect, this invention relates to a process for purifying pharmacologically-desirable active species from a mixture, thereby removing species present in the naturally occurring extract with less desirable properties.

In one aspect, this invention relates to a process for purifying pharmacologically-desirable active species from a mixture using High Performance Liquid Chromatography (HPLC), Size-Exclusion Chromatography (SEC), column chromatography, Ion Exchange Chromatography (IEX), Gel Permeation Chromatography (GPC), or any combination thereof.

In one aspect, the present disclosure provides the use of a compound of Formula I for the preparation of a medicament for the treatment of cancer. In one embodiment, tumor progression, including metastasis and/or growth is thereby inhibited and/or reduced.

In another aspect, the present disclosure provides a method of treating cancer comprising administering to a subject in need thereof a therapeutically effective amount of a pharmaceutical composition comprising a compound of any of Formula I, whereby the cancer is treated, cancer progression is stopped or slowed, and/or STAT3 is inhibited.

In one aspect, the level of STAT3 activity is reduced in cancer cells. In one aspect, the effective dose of the STAT3 inhibitor is administered at a dose ranging from 0.01 mg/kg to 20 mg/kg. The therapeutically effective dose may be, for example, about 0.01, 0.02, 0.03, 0.04, 0.05, 0.06, 0.07, 0.08, 0.09, 0.1, 0.2, 0.3, 0.4, 0.5, 0.6, 0.7, 0.8. 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.9, 3.0, 3.1, 3.2, 3.3, 3.4, 3.5, 3.6, 3.7, 3.8, 3.9, or about 4.0 mg/kg, or any range in between any two of the recited doses. In some aspects, the dose will be 0.08 mg/kg to about 0.5 mg/kg, from about 0.08 to about 0.24 mg/kg, or from about 0.24 to about 0.5 mg/kg. In another aspect, the effective dose of the STAT-3 inhibitor is given in one or more doses. For example, a therapeutically of, for example, 0.08, 0.24, or 0.5 mg/kg for each dose. In one embodiment, the dose is administered by a delivery route selected from the group consisting of intraperitoneal, intradermal, intramuscular, intraperitoneal, intravenous, topical, subcutaneous, intranasal, or epidural routes. In one aspect, the one or more effective doses of the STAT-3 inhibitor are administered orally, intravenously, intramuscularly, or subcutaneously. In one embodiment, the one or more effective doses of the STAT-3 inhibitor are administered orally. In one aspect, the one or more effective doses of the STAT-3 inhibitor are administered intravenously. In certain embodiments, the one or more effective doses of the STAT-3 inhibitor are administered subcutaneously. In one embodiment, the one or more effective doses of the STAT-3 inhibitor are administered intramuscularly.

In another aspect, the level of STAT3 activity is reduced in cancer cells. In one aspect, the effective dose of the STAT3 inhibitor is administered at a dose ranging from 0.01 microgram/kg to 4 mg/kg. The therapeutically effective dose may be, for example, about 0.01, 0.02, 0.03, 0.04, 0.05, 0.06, 0.07, 0.08, 0.09, 0.1, 0.2, 0.3, 0.4, 0.5, 0.6, 0.7, 0.8. 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.9, 3.0, 3.1, 3.2, 3.3, 3.4, 3.5, 3.6, 3.7, 3.8, 3.9, 4.0, 5.0, 6.0, 7.0, 8.0, 9.0, or about 10.0 microgram/kg, or any range in between any two of the recited doses. In some aspects, the dose will be 0.08 microgram/kg to about 0.5 microgram/kg, from about 0.08 to about 0.24 microgram/kg, or from about 0.24 to about 0.5 microgram/kg. In another aspect, the effective dose of the STAT-3 inhibitor is given in one or more doses.

In one aspect, this disclosure provides a method of treatment comprising administering to a subject in need thereof an effective amount of a pharmaceutical composition comprising a Stat3 inhibitor of this invention. In one embodiment, the subject has a glioma, breast cancer, ovarian cancer, or pancreatic cancer. In some embodiments, the subject has a solid tumor cancer. In another aspect, the solid tumor comprises sarcomas, carcinomas or lymphomas. In one embodiment, the cancer is selected from the group consisting of: brain tumors, such as gliomas, medulloblastomas, cerebral menangiomas, breast, prostate, pancreatic, ovarian, bladder, head and neck, malignant, multiple myeloma, lymphomas, including anaplastic large T cell lymphoma, Sezary syndrome, EBV-related Burkitt's Lymphoma, HSV Saimiri-dependent (T Cell), cutaneous T cell lymphoma, mycosis fungoides, leukemia, including HTLV-I dependent leukemia, erythroleukemia, acute lymphocytic leukemia (ALL), chronic lymphocytic leukemia (CLL), acute myelogenous leukemia (AML), chronic myelogenous leukemia (CML), megakaryocytic leukemia, and large granula lymphocyte (LGL) leukemia, or thyroid, lung, or kidney cancer. In some embodiments the cancer may be renal cell carcinoma, pancreatic adenocarcinoma, ovarian carcinoma, squamous cell carcinoma of the head and neck, or Hodgkin's Lymphoma.

In one aspect, this invention relates to a method of using formulations comprising the compounds of Formula I for the treatment of cancer in subjects.

The inventions described and claimed herein have many attributes and embodiments, including, but not limited to, those set forth, or described, or referenced, in this Brief Summary. It is not intended to be all-inclusive and the inventions described and claimed herein are not limited to, or by the features or embodiments identified in, this Brief Summary, which is included for purposes of illustration only and not restriction. Additional embodiments may be disclosed in the Detailed Description below.

DETAILED DESCRIPTION

The present disclosure is based on the surprising discovery that certain sesquiterpene lactone Stat3 inhibitors, including synthetic derivatives of sesquiterpene lactone compounds purified from Vc, had unexpected selective anti-cancer cell growth activity.

The present disclosure features, in some embodiments, novel STAT3 inhibitors, methods to purify compounds from a natural extract to obtain selective and potent Stat3 inhibitors and methods of using novel STAT3 inhibitors to treat cancer.

The present disclosure features, in some embodiments, novel, potent and selective STAT3 inhibitors, including sesquiterpene lactone inhibitors.

Constitutively activated STAT3 has been found to play a role in cancerous cells and the substantially faster proliferation, invasiveness and rate of cancerous cells compared to cells of the non-cancerous origin. In some embodiments, the selective STAT3 inhibitors of this invention can suppress cancer cell growth, including proliferation, survival, angiogenesis, migration/invasion and/or immunity. The inhibition of STAT3 can be achieved by inhibiting dimerization of STAT3.

STAT3:STAT3 protein complexes are mediated through reciprocal pTyr705SH2 domain interactions. Most drugs targeting STAT3 include a phosphoryl group to mimic pTyr705. While the phosphate functionality is regarded as being essential to targeting the SH2 domain, it is unsuitable for drug discovery as it suffers from poor cell permeability and metabolic degradation. As described herein, it was surprisingly ascertained that the compounds of Formula I are highly potent STAT3 inhibitors with micromolar potency against cancer cells, including breast cancer cells and some of the most aggressive brain cancer cells identified to this date.

*Vernonia cinerea* Less (Asteraceae) (Vc) is an annual herb that grows in South-East Asia, India and China. ("Dictionnaire des plantes utiliesees au Cambodge," Olympic, Phnom Penh, 2000, p. 915, "Flora of British India, III," London: L. Reeve and Co. Ltd., 1882, p. 233). It has been used for malaria, pain, inflammation, infections, diuresis, cancer, abortion, and various gastro-intestinal disorders. (Kirtikar, K. R.; and Basu, B. D. "Indian Medicinal Plants, II," India: New Connaught Place, Dehradun, 1975, p. 1322, Jain, S. P., Puri, H. S., J. Ethnopharmacol. 1984, 12, 213-222, Chea, A.; Hout, S.; Long, C.; Marcourt, L.; Faure, R.; Azas, N.; Elias, R.javascript; Chem. Pharm. Bull 2006, 54, 1437-1439, Tandon, M.; Shukla, Y. N.; Tripathi, A. K; Singh, S. C. Phytother. Res. 1998, 12, 195-199; Pratheeshkumar, P.; Kuttan, G. Immunopharmacol. Immunotoxicol. 2011, 33, 533-538; Grainger, C. R. J. Roy. Soc. Health, 1996, 116, 107-109). The phytochemicals previously reported from *V. cinerea* include (but not in purified isolated form) sesquiterpene lactones, steroidal glycosides, triterpenoids, and flavonoids. (Kuo, Y.-H.; Kuo, Y.-J.; Yu, A.-S.; Wu, M.-D.; Ong, C.-W.; Kuo, L.-M. Y.; Huang, J.-T.; Chen, C.-F.; Li, S.-Y. Chem. Pharm. Bull. 2003, 51, 425-426, Gunasingh, C.; Barnabas, G.; Nagarajan, S. Indian J. Pharm. Sci. 1981. 43, 114; Misra, T. N.; Singh, R. S.; Upadhyay, J.; Srivastava, R. Phytochemistry 1984, 23, 415-417). However, while it may be desirable to utilize Vc extracts for pharmacological use, the combination of multiple species within the extraction would result in multiple remedies, some of which may not be desirable. For example, a pregnant female may not desire to use Vc extracts (some of which are reported to induce abortion, supra) to treat pain. Thus, it is desirable to either isolate purified compounds of the Vc extracts or synthesize purified compounds which are derivative of those identified in Vc extracts for use in addressing specific maladies.

Curcumin, cucurbitacin I, withaferin A, betulinic acid, oleanolic acid and resveratrol and their analogs have been shown to differentially inhibit the JAK-STAT3 pathway. Inhibition of JAK-STAT3 signaling by the natural products suppressed tumor cell growth in vitro and tumor growth in vivo in certain cases [Miklossy, G., T. S. Hilliard, and J. Turkson, Therapeutic modulators of STAT signaling for human diseases, Nat Rev Drug Discov, 2013, 12: p. 611-629].

This disclosure features, in some embodiments, selective sesquiterpene lactone inhibitors of STAT3 purified from *Vernonia cinerea* (Vc), and compounds synthesized therefrom. For example, in some embodiments, this invention features the compounds of Formula I, including purified hirsutinolides, for example, compounds 6, 7, 10, 20 and 22 and synthetic derivatives of compound 22, for example, compounds zmm-1-19, 1-20, 1-22, 1-36, 1-37, 1-72, 1-79, 1-80, and 1-82. In some embodiments, the present disclosure features, in some embodiments, synthetic novel, potent and selective STAT3 inhibitors, including sesquiterpene lactones.

In some embodiments, the compounds of this invention selectively inhibit cancer. In some embodiments, the compounds of this invention suppress human glioma and breast cancer in part by inhibiting aberrantly-activated STAT3.

The synthetic derivatives of hirsutinolides such as compound 22 may be accomplished by methods described herein. While the synthetic routes used to create the novel STAT3 inhibitor compounds allowed for variation at the $R_1$, $R_2$, and $R_3$ sites of Formula I, it was surprisingly shown herein that optimizing the $R_1$ site yields selective, potent inhibitors of STAT3, useful for inhibiting tumor and cancer cells and for the treatment of cancer.

This disclosure relates in one aspect to a method for the purification of novel selective STAT3 inhibitor compounds derived from *Vernonia cinerea* (Vc). In another embodiment, this invention features synthetic derivatives of these purified compounds. In other embodiments, this invention features methods of using these compounds as a new class of selective inhibitors of STAT3 signaling, and for the treatment of cancer.

In one embodiment, this disclosure relates to compounds of Formula I, which selectively inhibit STAT3.

In one aspect, the selective STAT3 inhibitor compounds inhibit STAT3 and selectively inhibit tumors and cancer cells may exhibit a five-fold, six-fold, seven-fold, eight-fold, nine-fold, ten-fold, fifteen-fold, twenty-fold, twenty-five fold, thirty-fold, forty-fold, fifty-fold, one hundred-fold or higher fold difference in inhibiting cancer cells and non-cancer cells such as fibroblast cells.

In one embodiment, this invention relates to compounds of Formula I, where $R_1$ is selected from the group consisting of H or methyl ($CH_3$), 4-hydroxytigloyl, tigoyl, 2-methylacryloyl, acryloyl, acetyl, proponyl, butanyl, pentanyl, hexanyl, amide, cinnamyl, isodecenyl, isopentenyl, triazoles, substituted triazoles, (3-(4-(trifluoromethyl)phenyl)acryl, 3-(4-fluorophenyl)acryl, 3,7-dimethylocta-2,6-dienyl, 3-methylbut-2-enyl, 3,7-dimethyloct-6-enyl, 2-methylbut-2-enyl, 2-methylbut-2-enyl, substituted or unsubstituted $C_1$-$C_4$alkyl, substituted or unsubstituted $C_1$-$C_9$heteroalkyl, $C_1$-$C_9$alkoxyalkyl, $C_1$-$C_9$alkylaminoalkyl, substituted or unsubstituted $C_3$-$C_6$cycloalkyl, substituted or unsubstituted aryl, substituted or unsubstituted $C_2$-$C_8$heterocycloalkyl, substituted or unsubstituted heteroaryl, $C_1$-$C_9$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_9$heterocycloalkyl); $R_2$ is selected from the group consisting of H, 4-hydroxytigloyl, tigoyl, 2-methylacryloyl, acryloyl, amide, cinnamyl, triazoles, substituted triazoles, (3-(4-(trifluoromethyl)phenyl)acryl, 3-(4-fluorophenyl)acryl, 3,7-dimethylocta-2,6-dienyl, 3-methylbut-2-enyl, 3,7-dimethyloct-6-enyl, 2-methylbut-2-enyl, 2-methylbut-2-enyl, acetyl, proponyl, butanyl, pentanyl, hexanyl, isodecenyl, isopentenyl, methyl ($CH_3$), substituted or unsubstituted $C_1$-$C_9$alkyl, substituted or unsubstituted $C_1$-$C_9$alkenyl substituted or unsubstituted $C_1$-$C_4$heteroalkyl, $C_1$-$C_9$alkoxyalkyl, $C_1$-$C_9$alkylaminoalkyl, substituted or unsubstituted $C_3$-$C_9$cycloalkyl, substituted or unsubstituted aryl, substituted or unsubstituted $C_2$-$C_9$heterocycloalkyl, substituted or unsubstituted heteroaryl, $C_1$-$C_4$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_9$heterocycloalkyl); $R_3$ is selected from the group consisting of H or methyl ($CH_3$) or acetyl; with the proviso that the compound is not previously known.

In further embodiments, this disclosure relates to compounds of Formula I where, for example, $R_3$ is H, $R_2$ is acetyl, and $R_1$ is tigoyl. In another embodiment, this disclosure relates to compounds of Formula I where, for example, $R_3$ is H, $R_2$ is acetyl, and $R_1$ is 4-hydroxytigloyl. In another embodiment, this disclosure relates to compounds of Formula I where, for example, $R_3$ is H, $R_2$ is acetyl, and $R_1$ is 2-methylacryloyl.

In one embodiment, previously known compounds which have been identified are 8α-(2-methylacryloyloxy)-hirsutinolide, 8α-tigloyloxyhirsutinolide, 8α-tigloyloxyhirsutinolide-13-O-acetate, 8α-(2-methylacryloyloxy)-hirsutinolide-13-O-acetate, vernolide-B, 8α-hydroxyhirsutinolide, vernolide-A, loliolide, isololiolide, (3R)-3-hydroxy-ionone, apigenine, or (9Z,12S,13S)-dihydroxy-9-octadecanoic acid. These molecules have also been purified by the method disclosed herein from Vc extracts, shown to selectively inhibit cancer. For example, the compounds selectively inhibit cancer cells, as described herein, for example, in the Examples section, below.

In one embodiment, this disclosure relates to the compounds in Formula I, or a pharmaceutically acceptable salt, crystal or polymorph thereof.

In one embodiment, this disclosure relates to a pharmaceutical composition comprising a compound, salt, crystal or polymorph in any one of the compounds in Formula I, and a pharmaceutically acceptable excipient.

In one embodiment, this disclosure relates to a method for synthesizing the compounds of Formula I where $R_3$ is H, $R_2$ is acetyl, and $R_3$ is 4-hydroxytigloyl, tigoyl, 2-methylacryloyl, acryloyl, cinnamyl, isodecenyl, or isopentenyl, comprising (a) first reacting the appropriate carboxylic acid with 2,4,6-trichlorobenzoyl chloride by esterification, for example, the Yamaguchi esterification; and (b) reacting the resulting 2,4,6-trichlorobenzyl ester to compound 14 to yield the final compound. In alternative embodiments, the 2,4,6-trichlorobenzyl ester can be reacted to compounds 8 or 17 to yield a different series of compounds. The experimental details of this set of embodiments are described in the Examples, below.

In one embodiment, this invention relates to pharmaceutically active metabolites, or pharmaceutically acceptable solvates, pharmaceutically acceptable salts, enantiomers, polymorphs, or pharmaceutically acceptable prodrugs of the compounds of Formula I.

In one embodiment, this invention relates to formulations comprising compounds of Formula I, which selectively inhibit STAT3.

In one embodiment, this invention relates to a composition for use in selectively treating tumor cells having a constitutively activated STAT3, comprising an effective amount of a STAT3 inhibitor of Formula I. In another embodiment, this invention relates to formulations comprising compounds of FIGS. 2A-2B and/or FIG. 10, which selectively inhibit STAT3.

In one embodiment, this invention relates to a composition comprising a substantially pure STAT3 inhibitor of Formula I. "Purified" or "pure" is defined as greater than 85, 88, 90, 92, 95, 96, 97, 98, 98.5, or greater than 99% purity, as determined by HPLC. In some embodiments, "substantially pure" is defined as greater than 90% purity, as determined by HPLC.

In one embodiment, this invention relates to purified hirsutinolides which may be purified from Vc or synthesized, including for example, compounds 6, 7, 10, 20 and 22 and synthetic derivatives of 22, zmm-1-19, 1-20, 1-22, 1-36, 1-37, 1-72, 1-79, 1-80, and 1-82.

In one embodiment, this invention relates to novel, selective and potent STAT3 inhibitors, useful as cancer therapeutics. These compounds are useful, for example, for treating cancer. In some embodiments, the compounds of this invention are useful for treating solid tumors, for example, glioma and breast cancer or other cancers described herein. In some aspects, the compounds of this invention are useful for inhibiting malignant transformation, tumor development and progression.

In one embodiment, the invention relates to the inventors' design of Stat3 inhibitors which interfere with the dimerization between two monomers, and the inventors' recognition that this represents an attractive strategy to develop drugs that inhibit Stat3 activation and functions.

In one embodiment, this disclosure relates to novel, selective STAT-3 inhibitors, and pharmaceutical formulations and kits comprising the inhibitors. The compounds and pharmaceutical formulations are useful as therapeutics for cancer and other conditions mediated by aberrantly active STAT-3. In some aspects, the processes inhibited by the compounds and compositions of this invention include proliferation, survival, angiogenesis, migration/metastasis/invasion, and immunity.

Further synthesis of novel compounds of this invention can be accomplished by the reaction scheme detailed in FIG. 20 or by other synthetic methods.

The present disclosure features, in some embodiments, a novel method for purifying selective STAT3 inhibitors of this invention from Vc extracts. While Vc extracts contain compounds that inhibit certain cancer cells, such as cancer cells that have constitutively activated STAT3, the extracts also contain compounds which exhibit an inhibitory effect against non-cancer cells, such as cells required for homeostasis or other normal cells, such as fibroblasts, or other cells that do not have constitutively activated STAT3. Thus, to reduce the toxicity of the compounds of this invention purified from Vc extracts, the compounds which exhibit a high inhibitory effect against non-cancer cells, such as homeostatic cells or other normal cells must be removed. It has been surprisingly found that removing the non-selective compounds from the purified compounds of this invention yields highly selective, potent inhibitors of STAT3 useful in treating cancer and/or tumors.

This present disclosure describes methods of using High Performance Liquid Chromatography (HPLC) to produce a purified compound in which the amount of the toxic non-selective compounds is reduced. In some embodiments, HLPC may be used in tandem with Gravitational column chromatography (over silica gel). In other embodiments, a series of subsequent purifications of the fractions collected from a prior purification step can be performed to obtain the purified compounds. In some embodiments, compound 14 can be obtained by the purification method described herein, or by other methods known in the art.

In some embodiments, the selective STAT3 inhibitors of this invention may exhibit a five-fold, six-fold, seven-fold, eight-fold, nine-fold, ten-fold, fifteen-fold, twenty-fold, twenty-five fold, thirty-fold, forty-fold, fifty-fold, one hundred-fold or higher fold difference in inhibiting cancer cells and non-cancer cells such as fibroblast cells and/or other cells that do not have constitutively activated STAT3.

In one embodiment, the method of purifying a compound of Formula I from *Vernonia cinerea* leaves is comprised of (a) macerating the leaves; (b) performing a methanol extraction of the macerated leaves to obtain an extract; (c) performing a first HPLC or Gravitiational column chromatography purification step on the extract and collecting fractions; (d) identifying the fractions which are to be further purified; (e) performing a second HPLC purification step and collecting fractions; (f) identifying the fractions requiring further purification; and (g) performing an additional HPLC purification step; (h) removal of the mobile phase to yield the purified compound.

It should be appreciated by those skilled in the art that other methods of purifying the compounds than those cited herein that can be used. For example, High Performance Liquid Chromatography (HPLC), Size-Exclusion Chromatography (SEC), Gravitational column chromatography, Ion Exchange Chromatography (IEX), Gel Permeation Chromatography (GPC), Chiral HPLC, Supercritical Fluid Chromatography (SFC), Capillary Electrophoresis, or any combination thereof may be employed. A variety of mobile and stationary phases may be employed so as to achieve a similar result as that described in this disclosure. In addition, a variety of mobile phase flow rates, mobile phase gradient change rates, and mobile phase gradients may be employed to also purify the STAT3 inhibitor compounds. A variety of stationary phase materials, and stationary phase column geometries may be employed to also purify the STAT3 inhibitor compounds. The maceration solvent can be, for example, any polar solvent, including but not limited to dimethylsulfoxide (DMSO), methanol, ethanol, n-propanol, i-propanol, acetone, $CHCl_3$, $CH_2Cl_2$, N,N-dimethyl formamide (DMF), 2-butanone, and/or ethyl acetate or any combination thereof.

The present disclosure features, in some embodiments, a novel method for the treatment of cancer using novel STAT3 inhibitors. Treatment includes using formulations of the purified or synthesized compounds to inhibit tumor cell growth in vitro and in vivo. The present disclosure features, in some embodiments, a method of treating cancer, comprising administering to a subject in need thereof, a therapeutically effective amount of a pharmaceutical composition comprising a purified and/or synthetic STAT3 inhibitor of this invention, as set forth herein, or a pharmaceutically acceptable salt thereof. In one embodiment cancer progression is inhibited, for example, reduced. In one embodiment, the pharmaceutical composition comprises the STAT3 inhibitor of Formula I, or a pharmaceutically acceptable salt thereof.

Practitioners in the art will appreciate that the formulation employed in the Example below comprises Dimethylsulfoxide (DMSO) at concentration range from 0.1 to 5% in water, but other formulations may be employed with other pharmaceutical excipients or other drug delivery agents or articles of manufacture. In some embodiments, the delivery method of the treatment may be varied, including but not limited to oral, parenteral, subcutaneous, intravenous, or transdermal delivery or other modes or routes of delivery described herein.

In one embodiment, a pharmaceutical composition is used in selectively treating tumor cells having a constitutively activated STAT3, comprising an effective amount of a STAT3 inhibitor of Formula I In some embodiments, the effective dose of the STAT3 inhibitor is administed at a dose ranging from 0.01 microgram/kg to 4 mg/kg. The therapeutically effective dose may be, for example, about 0.01, 0.02, 0.03, 0.04, 0.05, 0.06, 0.07, 0.08, 0.09, 0.1, 0.2, 0.3, 0.4, 0.5, 0.6, 0.7, 0.8. 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.9, 3.0, 3.1, 3.2, 3.3, 3.4, 3.5, 3.6, 3.7, 3.8, 3.9, 4.0, 5.0, 6.0, 7.0, 8.0, 9.0, or about 10.0 mg/kg or from about 0.01, 0.02, 0.03, 0.04, 0.05, 0.06, 0.07, 0.08, 0.09, 0.1, 0.2, 0.3, 0.4, 0.5, 0.6, 0.7, 0.8. 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.9, 3.0, 3.1, 3.2, 3.3, 3.4, 3.5, 3.6, 3.7, 3.8, 3.9, 4.0, 5.0, 6.0, 7.0, 8.0, 9.0, or about 10.0 microgram/kg, or any range in between any two of the recited doses. In some aspects, the dose will be 0.08 microgram/kg to about 0.5 microgram/kg, from about 0.08 to about 0.24 microgram/kg, or from about 0.24 to about 0.5 microgram/kg, 0.05 mg/kg to about 5 g/kg or any range between any two of the recited doses. In one embodiment, the effective dose of STAT3 is from about 0.08 mg/kg to about 0.5 mg/kg, from about 0.08 to about 2.5 mg/kg, or from about 0.08 to about 2.0 mg/kg, or from about 1.0 to 2.0 mg/kg, to treat cancer. In another aspect, the effective dose of the STAT-3 inhibitor is given in one or more doses. For example, the dosage amount may be from 0.01 mg of drug per kilogram of subject body mass (mg/kg) to 5 mg/kg.

In one embodiment, an effective dose is defined by the amount of single or total compound administered in order to achieve a relative reduction in tumor volume compared to an untreated control of over 50% of the treated tumor to untreated tumor at sixty-five days after administration of the compound, for example a compound of Formula I, such as a compound shown in FIG. 19. In one embodiment, the effective dose of STAT3 is given in one or more doses. For example, a therapeutically of, for example, 0.08, 0.24, or 0.5 mg/kg for each dose.

In one embodiment, one or more effective doses of STAT3 are administered orally to treat cancer. In one embodiment, one or more effective doses of STAT3 are administered parenterally, subcutaneously, intravenously, or intramuscularly to treat cancer. In one embodiment, the cancer treated by this method is a solid tumor. In one embodiment, the cancer which is treated is selected from the group consisting of: brain tumors, glioma, medulloblastomas, cerebral menangiomas, lung, breast, prostate, pancreatic, ovarian, bladder, head and neck, thyroid, brain, and kidney. In one embodiment, the method of treating cancer relates to dosing each dose of the STAT3 inhibitor between about 0.01 mg/kg and less than about 4.0 mg/kg.

In one embodiment, the dose is administered by a delivery route selected from the group consisting of intraperitoneal, intradermal, intramuscular, intraperitoneal, intravenous, topical, subcutaneous, intranasal, or epidural routes. In one aspect, the one or more effective doses of the STAT-3 inhibitor are administered orally, intravenously, intramuscularly, or subcutaneously. In one embodiment, the one or more effective doses of the STAT-3 inhibitor are administered orally. In one aspect, the one or more effective doses of the STAT-3 inhibitor are administered intravenously. In certain embodiments, the one or more effective doses of the STAT-3 inhibitor are administered subcutaneously. In one embodiment, the one or more effective doses of the STAT-3 inhibitor are administered intramuscularly.

In one embodiment, this disclosure provides a method of treatment comprising administering to a subject in need thereof an effective amount of a pharmaceutical composition comprising a Stat3 inhibitor of this invention. In one embodiment, the subject has a glioma, breast cancer, or pancreatic cancer. In some embodiments, the subject has a solid tumor cancer. In another aspect, the solid tumor includes or excludes sarcomas, carcinomas or lymphomas. In one embodiment, the cancer includes or excludes: brain tumors, such as gliomas, medulloblastomas, cerebral menangiomas, breast, prostate, pancreatic, ovarian, bladder, head and neck, malignant, multiple myeloma, lymphomas, including anaplastic large T cell lymphoma, sezary syndrome, EBV-related Burkitt's Lymphoma, HSV Saimiri-dependent (T Cell), cutaneous T cell lymphoma, mycosis fungoides, leukemia, including HTLV-I dependent leukemia, erythroleukemia, acute lymphocytic leukemia (ALL), chronic lymphocytic leukemia (CLL), acute myelogenous leukemia (AML), chronic myelogenous leukemia (CML), megakaryocytic leukemia, and large granula lymphocyte (LGL) leukemia, or thyroid, lung, or kidney cancer. In some embodiments the cancer includes or excludes renal cell carcinoma, pancreatic adenocarcinoma, ovarian carcinoma, suamous cell carcinoma of the head and neck, or Hodgkin's Lymphoma.

In one embodiment, this invention relates to a method of using formulations comprising the compounds of Formula I for the treatment of cancer in subjects.

Any compound herein this disclosure can be used in any method of this invention. For example, any compounds of Formula I can be used to treat breast or glioma cancer.

DEFINITIONS

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which comprise oxygen, nitrogen, sulfur, or phosphorous, atoms replacing one or more carbons of the hydrocarbon backbone. The term "aromatic-alkyl" includes alkyl groups substituted with one or more aryl groups. The term "lower alkyl" as used herein refers to 9 or fewer carbons.

The term "aryl" includes groups with aromaticity, including 5- and 6-membered single-ring aromatic groups that may include from zero to four heteroatoms, as well as multicyclic systems with at least one aromatic ring, and also stilbenes (substituted and non-substituted) and vinyl stilbenes (substituted and non-substituted). Examples of aryl groups include benzene, phenyl, pyrrole, furan, thiophene, thiazole, isothiazole, imidazole, triazole, substituted triazoles, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused, or bridged, with alicyclic or heterocyclic rings which are not aromatic, so as to form a multicyclic system (e.g., tetralin, methylenedioxyphenyl).

The term "alkylene" refers to divalent saturated aliphatic groups and includes both straight chain and branched chain groups. The term includes the carboxylic acids and corresponding esters and amides, containing or reacting to unsaturated carbon-carbon double bonds. For example, this term includes, but is not limited to all (Z, and E configurations of the carbon-carbon double bond) of the enantiomers of: (3-(4-(trifluoromethyl)phenyl)acrylic acid, 3-(4-fluorophenyl)acrylic acid, cinnamic acid, 3,7-dimethylocta-2,6-dienoic acid, 3-methylbut-2-enoic acid, 3,7-dimethyloct-6-enoic acid, 2-methylbut-2-enoic acid, 2-methylbut-2-enoic acid.

As used herein, a "subject" refers to an animal that is the object of treatment, observation or experiment. "Animal" includes cold- and warm-blooded vertebrates and invertebrates, such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, apes, and prenatal, pediatric, and adult humans.

As used herein, "preventing" or "protecting" means preventing in whole or in part, or ameliorating, or controlling.

As used herein, the term "treating" refers to both therapeutic treatment and prophylactic, or preventative, measures, or administering an agent suspected of having therapeutic potential. The term includes preventative (e.g., prophylactic) and palliative treatment.

The term "a pharmaceutically effective amount", as used herein, means an amount of active compound, or pharmaceutical agent, that elicits the biological, or medicinal, response in a tissue, system, animal, or human that is being sought, which includes alleviation or palliation of the symptoms of the disease being treated and/or an amount sufficient to have utility and provide desired therapeutic endpoint. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; cause loss of viability, inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, e.g., by assessing the time to disease progression and/or determining the response rate.

The term "pharmaceutically acceptable", as used herein, means that the substance or composition must be compatible chemically and/or toxicologically, with the other ingredients comprising a formulation, and/or the mammal being treated therewith.

The term "cancer" refers to, or describes, the physiological condition in mammals that is typically characterized by unregulated cell growth and/or hyperproliferative activities. A "tumor" comprises one or more cancerous cells. Examples of cancer include, but are not limited to, carcinoma, lymphoma, blastoma, sarcoma, and leukemia or lymphoid malignancies. In one embodiment, the cancer is a solid tumor. More particular examples of such cancers include breast cancer, cervical cancer, ovarian cancer, bladder cancer, endometrial or uterine carcinoma, prostate cancer, glioma and other brain or spinal cord cancers, squamous cell cancer (e.g., epithelial squamous cell cancer), lung cancer, including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, liver cancer, hepatoma, colon cancer, rectal cancer, colorectal cancer, salivary gland carcinoma, kidney or renal cancer, vulval cancer, thyroid cancer, hepatic carcinoma, anal carcinoma, penile carcinoma, as well as head and neck cancer. In one embodiment, the treatment comprises treatment of solid tumors. In one embodiment, the tumors comprises sarcomas, carcinomas or lymphomas.

In some embodiments, the cancer is selected from the group consisting of: brain tumors, such as gliomas, medulloblastomas, cerebral menangiomas, pancreatic cancer, multiple myeloma, lymphomas, including anaplastic large T cell lymphoma, sezary syndrome, EBV-related Burkitt's Lymphoma, HSV Saimiri-dependent (T Cell), cutaneous T cell lymphoma, mycosis fungoides, leukemia, including HTLV-I dependent leukemia, erythroleukemia, acute lymphocytic leukemia (ALL), chronic lymphocytic leukemia (CLL), acute myelogenous leukemia (AML), chronic myelogenous leukemia (CML), megakaryocytic leukemia, and large granula lymphocyte (LGL) leukemia, thyroid cancer, brain cancer, lung cancer, and kidney cancer. In some embodiments the cancer may be renal cell carcinoma, pancreatic adenocarcinoa, ovarian carcinoa or Hodgkin Lymphoma.

A "metabolite" is a product produced through metabolism in the body of a specified compound, or salt thereof. Metabolites of a compound may be identified using routine techniques known in the art, and their activities determined, using tests such as those described herein. Such products may result e.g., from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The phrase "pharmaceutically acceptable salt" as used herein, refers to pharmaceutically acceptable organic, or inorganic, salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule, such as an acetate ion, a succinate ion, or other counter ion. The counter ion may be any organic, or inorganic, moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, e.g., treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like If the compound of the invention is an acid, the desired pharmaceutically acceptable salt may be prepared by any suitable method, e.g., treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A "solvate" refers to an association, or complex, of one or more solvent molecules and a compound of the invention. Examples of solvents that form solvates include, but are not limited to, water, isopropanol, ethanol, methanol, DMSO, ethylacetate, acetic acid, and ethanolamine.

Purification of Compounds from Extracts of *Vernonia cinerea*

Compounds purified from a chloroform-soluble partition of a methanol extract from the combined leaves and stems of *Vernonia cinerea* were shown to selectively inhibit the STAT3 activity in tumor cells such as glioblastoma cells (type U251MG) and breast cancer cells (type MDA-MB-231). For example, the compounds inhibited, e.g., promoted loss of viability of the two types of tumor cells in vitro, but exhibited less inhibition of non-cancer cells such as normal NIH-3T3 mouse fibroblasts. The difference inhibitory activity was around a two-fold to a four-fold or higher difference in inhibiting cancer cells compared to inhibition of non-cancer cells such as fibroblast cells. In some embodiments, there may be a five-fold, six-fold, seven-fold, eight-fold, nine-fold, ten-fold, fifteen-fold, twenty-fold, twenty-five fold, thirty-fold, forty-fold, fifty-fold, one hundred-fold or higher fold difference in inhibiting cancer cells and non-cancer cells such as fibroblast cells.

To obtain the purified, selective compounds, the chloroform partition of the combined leaves and stems of *V. cinerea* was repeatedly subjected to column chromatography on silica gel, RP-18 gel, Sephadex LH-20 gel, and preparative HPLC to obtain four new sesquiterpene lactones, 1-4, along with twelve known compounds (5-16).

Compound 1 was obtained as a white amorphous powder and gave a molecular ion at m/z 401.1724 [M+Na]$^+$ (calcd for $C_{20}H_{26}O_7Na$, 401.1726) in the positive-ion HRESIMS, corresponding to a molecular formula of $C_{20}H_{26}O_7$. The IR absorption band at 1760 cm$^{-1}$ and a strong absorption around 290 nm in the UV spectrum indicated the presence of a conjugated lactone group. The $^{13}C$ NMR spectrum showed characteristic signals that further supported the γ lactone group [$δ_C$, 169.4 (C-12), 147.5 (C-7), 146.4 (C-6), and 131.6 (C-11)] (Table 1).

TABLE 1

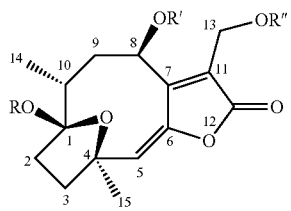

Compounds and associated side chains, and their activities against U251, MDA-MB-231, NIH3T3 and Stat3

| | | | | Activity against | | | |
|---|---|---|---|---|---|---|---|
| Compounds | R | R' | R" | U251 | 231 | 3T3 | Stat3 |
| 6 | H | (side chain) | (side chain) | +++ | +++ | +++ | +++ |
| 7 | H | (side chain) | (side chain) | ++ | + | +/− | + |

TABLE 1-continued

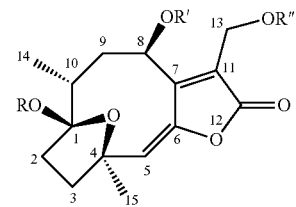

Compounds and associated side chains, and their
activities against U251, MDA-MB-231, NIH3T3 and Stat3

| Compounds | R | R' | R" | Activity against U251 | 231 | 3T3 | Stat3 |
|---|---|---|---|---|---|---|---|
| 8 | H | (O=C-C(CH3)=CH-CH3 group) | H | +/− | nd | nd | nd |
| 9 | CH3 | (O=C-C(=CH2)CH3 group) | (O=C-CH3 group) | +/− | nd | nd | − |
| 10 | CH3 | (O=C-C(CH3)=CH-CH3 group) | (O=C-CH3 group) | ++ | + | +/− | ++ |
| 11 | H | H | (O=C-CH3 group) | +/− | nd | nd | + |
| 14 | H | H | H | − | nd | nd | nd |
| 15 | CH3 | H | H | − | nd | nd | nd |
| 17 | CH3 | (O=C-C(CH3)=CH-CH3 group) | H | − | nd | nd | nd |
| 18 | H | (O=C-C(=CH2)CH3 group) | H | +/− | nd | nd | − |
| 19 | H | (O=C-CH=C(CH3)- group) | H | − | nd | nd | − |
| 20 | H | (O=C-C(CH3)=CH-CH3 group) | (O=C-CH3 group) | ++ | + | +/− | + |

TABLE 1-continued

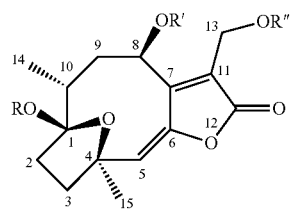

Compounds and associated side chains, and their
activities against U251, MDA-MB-231, NIH3T3 and Stat3

| | | | | Activity against | | | |
|---|---|---|---|---|---|---|---|
| Compounds | R | R' | R" | U251 | 231 | 3T3 | Stat3 |
| 21 | H | [structure: tigloyl-type with OH] | H | − | nd | nd | nd |
| 22 | H | H | [structure: tigloyl] | ++ | + | +/− | ++ |
| 28 | CH₃ | [structure: methacryloyl] | H | − | nd | nd | − | nd, not determined;
+, active;
−, no activity,
+/−, poorly active.

The NMR and HSQC spectra revealed two methyls at [δH, 0.97 (d, J=6.8 Hz)/δC, 16.8 (CH3-14) and δH, 1.48 (s)/δC, 27.9 (CH3-15)], three methylenes at [δH, 2.16 m/δC, 38.5 (C-2), δH, 2.16 m/δC, 38.6 (C-3), and δH, 2.36 (dd, J=15.62, 11.6 Hz, H-9α), 1.87 (m, H-9β)/δC, 37.9 (C-9)], a methine at δH, 1.90 (m)/δC, 41.3 (C-10), an oxymethine downfield shifted at δH, 6.34 (d, J=8.0 Hz)/δC, 68.2 (C-8), and an olefinic signal at δH, 5.87 (s)/δC, 125.6 (C-5), all of which suggested the presence of a hirsutinolide-type sesquiterpene. The 1H NMR spectrum revealed additional oxygenated methylene protons at [δH, 4.65 (d, J=13.2 Hz, H-13a) and 4.56 (d, J=13.2 Hz, H-13b)], which showed two- and three-bond correlation peaks with C-7, C-12, and C-11 in the HMBC spectrum (Table 1), and suggested that this oxymethylene group was attached to the γ lactone moiety. In addition, the 1H and 13C NMR spectra showed an olefinic signal at δH, 6.17 (q, J=7.6 Hz)/δC, 139.9 (C-3'), two methyl groups downfield shifted at [δH, 2.02 (d, J=7.6 Hz)/δC, 15.9 (C-4') and δH, 1.93 (s)/δC, 20.6 (C-5')], an olefinic quaternary carbon at δC, 128.2 (C-2'), and an ester carbonyl carbon at δC, 170.4 (C-1'), that were indicative of a tigloyl moiety based on the HSQC and HMBC analyses. The 1H and 13C NMR spectra of 1 were almost identical, to those of 8α-tigloyloxy-hirsutinolide, with the following exceptions: the signal for an olefinic proton (H-3') at δH, 7.03 in 8α-tigloyloxy-hirsutinolide was shifted upfield to δH, 6.17 in 1. In contrast, two methyl group protons at δH, 1.78 (CH3-4') and δH, 1.80 (CH3-5') in 8α-tigloyloxy-hirsutinolide were shifted downfield to 2.02 ppm and 1.93 ppm, respectively, in the tigloyl group of 1 (Table 2), implying that the olefinic (C-2'-C-3') bond was in the Z configuration. These observations were further supported by the NOESY correlation between H-3' and CH3-5' (Table 2). Additional NOESY correlations between H-8 and H-9β/H-13 along with the physicochemical data supported the same configurations in the hirsutinolide type of sesquiterpene lactone, and was comparable with literature data. (Kuo Y H, Kuo Y J, Yu A S, Wu M D, Ong C W, Kuo L M Y, Huang J T, Chen C F, Li S Y, Two novel sesquiterpene lactones, cytotoxic vernolide-A and -B, from *Vernonia cinerea*, Chem Pharm Bull 2003, 51:425-6; Youn U J, Park E J, Kondratyuk T P, Simmons C J, Borris R P, Tanamatayarat P, Wongwiwatthananukit S, Toyama O, Songsak T, Pezzuto J M, Chang L C, Anti-inflammatory sesquiterpene lactones from the flower of *Vernonia cinerea*, Bioorg Med Chem Lett 2012; 22:5559-62). In particular, X-ray crystallographic analysis defined the relative configuration of 8α-tigloyloxy-hirsutinolide obtained in our previous work. (Youn U J, Park E J, Kondratyuk T P, Simmons C J, Borris R P, Tanamatayarat P, Wongwiwatthananukit S, Toyama O, Songsak T, Pezzuto J M, Chang L C, Anti-inflammatory sesquiterpene lactones from the flower of *Vernonia cinerea*, Bioorg Med Chem Lett 2012; 22:5559-62). Therefore, compound 1 is a novel hirsutinolide geometric isomer, 8α-(2'Z-tigloyloxy)hirsutinolide.

TABLE 2

NMR data of Compounds 1-4. (a) Spectra recorded at $^1$H (400 MHz)
and $^{13}$C NMR (100 MHz) in CDCl$_3$. Chemical shift (delta) are in ppm, and
coupling constants (J, in Hz) are given in parenthesis. The assignments were based on
DEPT, COSY, NOESY, HSQC, and HMBC experiments. (b) overlapping signals.

| | 1$^a$ | | 2$^a$ | | | 3$^a$ | | 4$^b$ | |
| --- | --- | --- | --- | --- | --- | --- | --- | --- | --- |
| position | $\delta_{H, mult.}$ (J in Hz) | $\delta_C$ | $\delta_{H, mult.}$ (J in Hz) | $\delta_C$ | position | $\delta_{H, mult.}$ (J in Hz) | $\delta_C$ | $\delta_{H, mult.}$ (J in Hz) | $\delta_C$ |
| 1 | | 108.0 | | 107.8 | 1 | | 107.9 | | 109.1 |
| 2α | 2.16, m$^b$ | 38.5 | 2.10, m$^b$ | 38.1 | 2α | 2.06, m$^c$ | 37.3 | 2.20, m$^c$ | 37.0 |
| 2β | | | | | 2β | | | 2.07, m$^c$ | |
| 3 | 2.16, m$^b$ | 38.6 | 2.10, m$^b$ | 39.2 | 3 | 2.12, m$^c$ | 38.0 | 2.24, m$^c$ | 38.4 |
| 4 | | 81.2 | | 83.4 | 4 | | 80.6 | | 80.9 |
| 5 | 5.87, s | 125.6 | 5.90, s | 126.1 | 5 | 5.99, s | 126.4 | 5.86, s | 123.7 |
| 6 | | 146.4 | | 145.5 | 6 | | 146.2 | | 146.2 |
| 7 | | 147.5 | | 150.8 | 7 | | 149.1 | | 154.9 |
| 8 | 6.34, d (8.0) | 68.2 | 6.28, d (10.8) | 68.3 | 8 | 6.43, d (8.0) | 69.1 | 5.19, dd (11.6, 6.0) | 66.5 |
| 9α | 2.36, dd (15.6, 11.6) | 37.9 | 2.36, dd (15.6, 12.8) | 35.4 | 9α | 2.40, dd (14.0, 12.0) | 35.4 | 2.24, m$^c$ | 38.1 |
| 9β | 1.87, m | | 1.83, m | | 9β | 1.94, m | | 1.84, m | |
| 10 | 1.90, m | 41.3 | 1.88, m | 41.3 | 10 | 1.91, m | 41.6 | 1.94, m | 40.4 |
| 11 | | 131.6 | | 128.8 | 11 | | 133.5 | | 133.7 |
| 12 | | 169.4 | | 167.8 | 12 | | 168.2 | | 166.8 |
| 13α | 4.65, d (13.2) | 54.4 | 5.12, d (12.4) | 55.5 | 13 | 4.50, s | 52.9 | 4.97, s | 55.0 |
| 13β | 4.56, d (13.2) | | 5.05, d (12.4) | | 14 | 0.93, d (6.8) | 16.0 | 0.95, d (7.6) | 17.3 |
| 14 | 0.97, d (6.8) | 16.8 | 0.97, d (7.6) | 16.6 | 15 | 1.51, s | 27.0 | 1.61, s | 28.4 |
| 15 | 1.48, s | 27.9 | 1.50, s | 29.4 | 1' | | 167.0 | | 167.1 |
| 1' | | 170.4 | | 170.8 | 2' | | 127.3 | | 127.4 |
| 2' | | 128.2 | | 126.9 | 3' | 7.08, t (6.4) | 142.3 | 6.88, q (6.8) | 138.6 |
| 3' | 6.17, q (7.6) | 139.9 | 6.10, q (8.5) | 138.1 | 4' | 4.28, d (6.4) | 58.4 | 1.81, d (6.8) | 14.4 |
| 4' | 2.02, d (7.6) | 15.9 | 2.01, d (8.4) | 15.8 | 5' | 1.84, s | 11.2 | 1.84, s | 12.0 |
| 5' | 1.93, s | 20.6 | 1.92, s | 19.0 | OH-8 | | | 6.15, d (11.6) | |
| COCH$_3$ | | | | 170.7 | | | | | |
| COCH$_3$ | | | 2.10, s | 20.9 | | | | | |

Compound 2 was obtained as a white amorphous powder. It had a molecular ion at 443.1817 [M+Na]$^+$ (calcd for C$_{22}$H$_{28}$O$_8$Na, 443.1829) in the HRESIMS. The $^1$H and $^{13}$C NMR spectra of 2 were similar to those of 1, except for an additional methyl group at $\delta_H$, 2.10 (3H, s)/$\delta_C$, 20.9 and a carbonyl carbon at $\delta_C$, 170.7, consistent with an acetyl moiety. The HMBC spectrum showed a correlation peak between the oxymethylene proton (H-13) and the ester carbonyl carbon ($\delta_C$, 170.7), suggesting that the acetyl group was attached to an oxygen atom at C-13. The chemical shifts and the NOESY correlation between H-3' and CH$_3$-5' in the tigloyl group supported the cis (Z) olefinic double bond between C-2' and C-3'. The stereochemistry of asymmetric carbons of 2 was the same as in 1, by comparison of the physicochemical data and NOESY correlations of the two compounds. Thus, compound 2 was elucidated as a new geometric isomer, 8α-(2'Z-tigloyloxy)hirsutinolide-13-O-acetate.

Compound 3 was obtained as a white amorphous powder and its molecular formula was established as C$_{20}$H$_{26}$O$_8$ by HRESIMS (observed, 417.1660; calcd for [M+Na]$^+$ 417.1672). The UV, IR, and NMR spectra of 3 indicated a hirsutinolide skeleton comparable to those of 1 and 2. However, the $^1$H NMR spectrum revealed additional oxygenated methylene protons at $\delta_H$, 4.28 (2H, d, J=6.4 Hz, H-4'), which showed two- and three-bond HMBC correlations with the two olefinic carbons (C-2' and C-3'), indicating the attachment of an oxymethylene group instead of a methyl group at C-3' of the tigloyl moiety. The specific splitting pattern and the coupling constant of the olefinic proton (H-3') at $\delta_H$, 7.08 (t, $^3$J$_{H-3', H-4'}$=6.4 Hz) appeared to result from coupling with the oxymethylene proton (H-4'), and further supported the presence of the 4-hydroxytigloyl moiety (Table 2). In addition, the HMBC correlation observed between H-8 and the ester carbonyl carbon (C-1') demonstrated that the 4-hydroxytigloyl group was attached to C-8 of the sesquiterpene lactone molecule. The relative stereochemistry of 3 was determined in a manner similar to those of 1 and 2. Accordingly, compound 3 is proposed as a new compound, 8α-(4-hydroxytigloyloxy)-hirsutinolide.

Compound 4 was obtained as a white amorphous powder with a molecular ion at m/z 401.1722 [M+Na]$^+$ (calcd for C$_{20}$H$_{26}$O$_7$Na, 401.1723) in the HRESIMS, corresponding to an elemental formula of C$_{20}$H$_{26}$O$_7$. The 1D and 2D NMR spectra of 4 showed a (2'E)-tigloyl moiety, three methylenes, two methyls, an olefinic, an oxymethine, and a γ lactone group, indicating a hirsutinolide-type sesquiterpene lactone, initially assumed from the spectra data to be similar to 8α-tigloyloxyhirsutinolide (6). (Borkosky S, Bardon A, Catalan Cesar A. N, Diaz J. G, Herz W. Glaucolides, hirsutinolides and other sesquiterpene lactones from *Vernonanthura pinguis*. Phytochemistry 1997, 44:465-70). However, the $^1$H NMR spectrum of 4 showed an additional hydroxyl proton doublet at $\delta_H$, 6.15 (1H, d, J=11.6 Hz), which correlated with C-7/C-8/C-9 in the HMBC spectrum (Table 2), indicated that the hydroxyl group was connected to C-8. In addition, magnetically equivalent oxygenated methylene protons at $\delta_H$, 4.97 (2H, s, H-13) were observed in the $^1$H NMR spectra, which also showed a three-bond correlation with a lactone carbonyl carbon (C-12) and an ester carbonyl carbon (C-1') of the tigloyl moiety in the HMBC spectrum. These observations unambiguously indicated that the tigloyl group was attached at C-13 through an oxygen atom (Table 1). The NOESY correlation peaks between α-oriented OH-8 proton and H-9α, and between H-13 and H-8 (Table 2), along with the physicochemical analyses of 4 supported the same relative configurations compared to those of 1-3. Therefore, the structure of 4 was established as a new compound, 8α-hydroxy-13-O-tigloyl-hirsutinolide.

The other twelve isolates were identified as the known compounds, 8α-(2-methylacryloyloxy)-hirsutinolide (5) (Borkosky, supra), 8α-tigloyloxyhirsutinolide (6) (Borkosky, supra), 8α-tigloyloxyhirsutinolide-13-O-acetate (7) (Borkosky, supra), and Jakupovic J, Banerjee S, Castro V, Bohlmann F, Schuster A, Msonthi J. D, Keeley S. Poskeanolide, a seco-germacranolide and other sesquiterpene lactones from *Vernonia* species Phytochemistry 1986; 25:1359-64], 8α-(2-methylacryloyloxy)-hirsutinolide-13-O-acetate (8) (Borkosky, supra and Jakupovic, supra], vernolide-B (9) (Kuo, supra), 8α-hydroxyhirsutinolide (10) (Youn, supra], and vernolide-A (11) (Youn, supra), loliolide (12) (Park K E, Kim Y A, Jung H A, Lee H J, Ahn J W, Lee B J, Seo Y, Three norisoprenoids from the brown alga *Sargassum thunbergii*, J Korean Chem Soc 2004; 48:394-8), isololiolide (13) (Park, supra), (3R)-3-hydroxy-ionone (14) (Perez C, Trujillo J, Almonacid L N, Trujillo J, Navarro E, Alonso S J, Absolute structures of two new C13-norisoprenoids from *Apollonias barbujana*, J Nat Prod 1996; 59:69-72), apigenine (15) (Wada H, Satake T, Murakami T, Kojima T, Saiki Y, Chen C M. Chemical and chemotaxonomic study of pteridophytes, Studies of the chemical constituents of *Alsophila spinulosa* Tryon, Chem Pharm Bull 1985; 33:4182-7), (9Z,12S,13S)-dihydroxy-9-octadecanoic acid (16) (Gardner H W, Hou C T, Weisleder D, Brown W. Biotransformation of linoleic acid by *Clavibacter* sp. ALA2: heterocyclic and heterobicyclic fatty acids, Lipids 2000; 35:1055-60), by comparison of their physical and spectral data with published values. Compounds 12-14 and 16 are were isolated and purified for the first time from this plant source. These compounds were thus isolated from a mixture of compounds which also contained species which were highly inhibitory to housekeeping cells (such as fibroblast cells), such as NIH3T3 fibroblasts. Because the fibroblast-inhibiting compounds were removed, the purified compounds present utility as pharmacological agents as they present a reduced toxicity profile.

Using Purified Compounds and Synthesized Compounds to Inhibit STAT3 in Tumor Cells A bioassay comprising the CyQuant (Invitrogen, Carlsbad, Calif.) system was used in conjunction with the use of-guided fractionation of Vc extracts was conducted in which extracts, fractions, and sub-fractions were sequentially evaluated for effects against the growth of human cancer cells harboring aberrantly-active STAT3, compared to the effects on cells that do not. These studies led to the identification of active and inactive hirsutinolides (FIG. 2). The CyQuant assay was further used to screen all the purified hirsutinolides at an initial concentration of 5 micromolar for activity against the growth of human glioma, U251MG, U373MG and SF295 cells, breast cancer, MDA-MB-231 cells, and NIH3T3 mouse fibroblasts which do not harbor aberrantly active STAT3.

Formulations comprising any one of compounds 1-22 were evaluated for their inhibitory effects against aberrant STAT3 activity in the U251MG glioblastoma cancer cell and MDA-MB-231 breast cancer cells, and the viability of the two tumor lines that harbor constitutively-active STAT3, compared to normal NIH-3T3 mouse fibroblast. As compared with the blank, control compounds 4 and 7-9 showed 64% to 88% inhibitory effects against the viability of U251MG glioblastoma cell line. Compound 7 showed similar inhibitory effects in all of the tested cell lines. Compounds 2 and 6 showed weak inhibitory effect in the U251 MG glioblastoma cell line. However, the other compounds were inactive in the tested cell lines (FIGS. 5A-5B). Further, treatment of U251MG (glioblastoma multiforme tumor) or MDA-MB-231 (breast tumor) cells with compound 7 inhibited intracellular phospho-Tyrosine STAT3 (pY705STAT3) (FIGS. 5A-5B), suggesting the potential that inhibition of aberrant STAT3 activity in the tumor cells contribute to the loss of viability induced by two compounds. Therefore, there are some compounds in the unpurified extract (such as compound 7) which are highly active against the NIH3T3 fibroblasts, and therefore non-selective. Purifying away the non-selective compounds from the selective compounds of interest (those containing desirable anti-tumor properties, for example), such as compound 4, which has a lower inhibitory effect on the NIH3T3 fibroblasts yet also exhibits a high inhibitory effect on U251 MG (gliomablastoma multiforme tumor) or MDA-MB-231 (breast tumor) cells, therefore yielded selective inhibitors from the extract of Vc having a different toxicity profile compared to the unpurified extract.

Of the hirsutinolides (FIG. 2), compounds 6, 7, 10, 20 and 22 differentially suppressed the viability of malignant cells (FIGS. 8A-8C). Compounds 7, 10, 20 and 22 were selective against the growth of human glioma U251MG cells that harbor constitutively-active STAT3, while 6 inhibited the growth of all cells tested (FIGS. 8A-8C). Dose-response studies confirmed the activities of the compounds against various cell lines (FIGS. 7A-7E). More specifically, the studies provided the $IC_{50}$ values of 1.7, 2.6, 3.4, 4.3 and 2.6 micromolar for compounds 6, 7, 10, 20 and 22, respectively, for the inhibition of U251MG cell viability (FIG. 7A), $IC_{50}$ values ranging from 3.5-8.3 micromolar for effects of the compounds against U373MG, $IC_{50}$ values ranging from 1.8-7.0 micromolar for effects of the compounds against MDA-MB-231, $IC_{50}$ values ranging from 7.5-25.4 micromolar for activities of the compounds against SF295, and $IC_{50}$ values ranging from 2-10.8 micromolar for activities of the compounds against normal NIH3T3 (FIGS. 9B-9E). By contrast, compounds 8, 9, 11, 14, 18, 19 and 28 have moderate to weak activity against the cell lines when similarly tested at 5 micromolar (FIGS. 8A-8C, and Table 1). For comparison, the known compounds, costinulide and parthenolide, which are also sesquiterpene lactones are non-specfically active against glioma U251MG and normal NIH3T3 mouse fibroblasts (FIG. 8C).

Based on the preferential inhibitory effects of 22 against glioma U251 MG cell growth (FIGS. 8A-8C), it was synthesized ab initio, as were its structural analogs using 14 as a starting material. CyQuant assays showed the synthetic derivatives, zmm-1-19, 1-20, 1-22, 1-36, 1-37, 1-72, 1-79, 1-80, and 1-82 retained the inhibitory potency as 22 (FIG. 10). Notably, zmm-1-37 and 1-78 also inhibited breast cancer, MDA-MB-231, while zmm-1-36 lost cell-type specificity compared to 1-37 (FIG. 10).

A variety of sesquiterpene lactones have been shown to possess considerable anti-inflammatory activity. Several studies for sesquiterpene lactones have provided an evidence that DNA binding of NF-κB was prevented by alkylation of cysteine-38 in the p65/NF-κB subunit. (Garcia-Pineres A J, Castro V, Mora G, Schmidt T J, Strunck E, Pahl H L, Merfort I, Cysteine 38 in p65/NF-κB plays a crucial role in DNA binding inhibition by sesquiterpene lactones, J Biol Chem 2001; 276:39713-20; Garcia-Pineres A J, Lindenmeyer M T, Merfort I, Role of cysteine residues of p65/NF-κB on the inhibition by the sesquiterpene lactone parthenolide and N-ethyl maleimide, and on its transactivating potential, Life Sci 2004; 75:841-56). There are strong indications that this is a general mechanism for sesquiterpene lactones, which possess α,β-unsaturated carbonyl structures such as α-methylene-γ-lactones or α,β-unsaturated cyclopentenones. These functional groups are known to react with nucleophiles, especially with the sulfhydryl group of cysteine, in a Michael-type addition. (Schmidt T J. Toxic activities of sesquiterpene lactones: Structural and biochemical aspects, Curr Org Chem 1999; 3:577-608). Two sesquiterpene lactones, dehydrocostuslactone and costunolide were reported to induce a rapid drop in intracellular glutathione content and consequently inhibited the tyrosine-phosphorylation of STAT3 in cells treated with IL-6, while, dihydrocostunolide, a structural analogue of costunolide lacking only the α,β-unsaturated carbonyl group failed to exert inhibitory action toward STAT3 tyrosine phosphorylation, indicating that this unsaturation in the lactone ring may play a pivotal role in its biochemical activity. (Butturini E, Cavalieri E, Carcereri de Prati A, Darra E, Rigo A, Shoji K, Murayama N, Yamazaki H, Watanabe Y, Suzuki H, Mariotto S, Two naturally occurring terpenes, dehydrocostuslactone and costunolide, decrease intracellular GSH content and inhibit STAT3 activation, PLoS One 2011; 6:e20174). Studies of germacranolide type sesquiterpene lactones, costunolide and parthenolide, herein show that these are generally toxic to U251MG and normal NIH3T3 irrespective of the pSTAT3 STATus. Further, the inhibition of pSTAT3 at 5 micromolar was negligible or weak, compared to compound 7. These results suggest costunolide and parthenolide likely have broad effects on multiple targets.

Hirsutinolide-type sesquiterpene lactones, 1-11 isolated from *V. cinerea* possess an α,β-unsaturated-γ-lactone ring and a 1β,4β-expoxy group as common functional groups. Although the structure-activity relationship of the sesquiterpene lactones has not been investigated thoroughly, our results suggest the hirsutinolide type sesquiterpene lactone possessing an α,β-unsaturated-γ-lactone moiety and an ester carbonyl group at C-13 position may enhance the STAT3 inhibitory activity in these cancer cell lines.

Synthesis of STAT3 Inhibitors which are Derived from Purified Compounds of Vc Extract Based on the preferential inhibitory effects of 22 against glioma U251 MG cell growth (FIGS. 8A-8C), it was synthesized ab initio, as were its structural analogs using 14 as a starting material. CyQuant assay shows the synthetic derivatives, zmm-1-19, 1-20, 1-22, 1-36, 1-37, 1-72, 1-79, 1-80, and 1-82 retained the inhibitory potency as 22 (FIG. 9). Notably, zmm-1-37 and 1-78 also inhibited breast cancer, MDA-MB-231, while zmm-1-36 lost cell-type specificity compared to 1-37 (FIG. 10).

Evaluation of Vc-derived hirsutinolides and the synthetic analogs of 22 yielded evidence that the bulky lipophilic side chain at position 13 is vital for both anticancer and STAT3 inhibitory activities (compare 6 and 22 to 14, and 10 to 15) (FIG. 2, and Table 1). When a smaller group (e.g., acetoxy) is present at position $R_3$, a bulkier group at $R_2$ enhanced activity (compare 6, 10 and 20 with an extra $CH_3$ group to 7 and 9). A sole appendage at position $R_2$ is insufficient for activity (see 8, 17, 18 and 19). The specific synthesis are described below in the Examples section.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Use of Synthesized Compounds Derived from Purified Compound 14 to Differentially Inhibit Cells with Varying Degrees of STAT3 Activation As aberrant STAT3 activity promotes cell proliferation, survival, and other tumor processes that support malignant cell phenotype; this invention relates in one embodiment to the identification of synthetic compounds that inhibit active STAT3 and cancer cell growth.

As the newly identified hirsutinolides inhibit growth of malignant cells that harbor aberrantly-active STAT3 and because STAT3 activity is involved in cancer cell growth and survival, isolated and synthesized compounds were tested against intracelluar STAT3 activity. U251MG and MDA-MB-213 cells harboring aberrantly-active STAT3 were treated with 5 micromolar of exemplary compounds 6, 7, 10, 20 or 22 in DMSO/water solutions for 0-24 h. The time-course studies showed early inhibition at 15-30 min of pY705STAT3, as analyzed by immunoblotting, with no change in total STAT3 (FIG. 11A(i)), and of STAT3 DNA-binding activity, as analyzed by electrophoretic mobility shift assay (EMSA) (FIG. 11A(ii)), and apparent weakened inhibitory activities at later than 6 h (FIG. 11A-11D), even though the same treatment conditions would ultimately lead to loss of viable cells (FIGS. 8A-8C and 9A-9F). Immunoblotting analysis further showed treatment of U251MG cells with increasing concentrations of the compounds for 2 h showed dose-dependent inhibition of pY705STAT3, with no change in total STAT3 (FIG. 11C). Comparatively, the known sesquiterpene lactones, costinulide and parthenolide, which had shown general cytotoxicity (FIG. 8C), had little effect on STAT3 activity. Further, the weakly-active hirsutinolides, 9, 11, 18, 19 or 28 had little effects on pY705STAT3 (FIGS. 11A-11D). Furthermore, similar to compound 22, treatment of U251MG cells with its synthetic analogs, zmm-1-19, 1-20, 1-22, 1-36 and 1-37 inhibited pY705STAT3 (FIG. 11D(i)), while the semi-synthesized agents, zmm-1-18, 1-21 and 1-23 showed little effects on pY705STAT3 (FIG. 11D(ii)).

To further determine the effects of the bioactive agents on STAT3 activity, nuclear extracts prepared from v-Src-transformed mouse fibroblasts (NIH3T3/v-Src) containing active STAT3 were directly incubated with 5 micromolar compounds for 30 min at room temperature prior to performing STAT3 DNA-binding activity in vitro with EMSA analysis. Results show strong inhibition of STAT3 DNA-binding activity by compounds 6, 7, 10, 20 and 22, in a dose-dependent manner as shown for compound 6 (FIG. 12A(ii)), while the inactive hirsutinolides, compounds 8, 9, 18, 19 and 28 had moderate to no effect (FIG. 12A(i)). Interestingly, the moderately active compound 11, which had little effect on intracellular STAT3 activation (FIG. 11B), inhibited STAT3 activity when co-incubated with STAT3 in this DNA-binding assay (FIG. 12A(i)). These studies indicate that agents directly interact with STAT3 and disrupt STAT3:STAT3 dimers, thereby inhibiting its DNA-binding activity.

Mechanism of Inhibition of Intracellular STAT3 Activity

By selectively labeling the 68 kDa construct of STAT3, encompassing residues 127-711 at the methyl groups of 37 Val, 59 Leu, and 35 Ile using previously described protocols. (Ayala, I., et al., An efficient protocol for the complete incorporation of methyl-protonated alanine in perdeuterated protein, Journal of biomolecular NMR, 2009, 43: p. 111-9; Gelis, I., et al., Structural basis for signal-sequence recognition by the translocase motor SecA as determined by NMR, Cell, 2007, 131: p. 756-69; Goto, N. K., et al., A robust and cost-effective method for the production of Val, Leu, Ile (delta 1) methyl-protonated 15N-, 13C-, 2H-labeled proteins, Journal of biomolecular NMR, 1999, 13: p. 369-74; Hu, W., et al., Selective editing of Val and Leu methyl groups in high molecular weight protein NMR, Journal of biomolecular NMR, 2012, 53: p. 113-24), we successfully obtained a quality, well-dispersed two-dimensional (2D)$^1$H-$^{13}$C heteronuclear multiple quantum correlation (HMQC)

spectrum for the unphosphorylated STAT3 (FIG. 12, part B). Focusing on compounds 6 and 10, indicate significant chemical shift changes in a dose-dependent manner, which indicate direct binding to STAT3. The interaction appears to have a slow dissociation rate constant, because the signals of the free and bound STAT3 are distinct. This finding indicates that their affinity for STAT3 is very high, with $K_d$ less than 1 nanomolar. There are similarities in their interactions with STAT3. The compounds caused the disappearance of the same set of resonances in the Leu/Val region of the spectrum, indicating that they bind to the same region. However, the new resonances from the spectrum of the complexes are quite different between the two compounds, indicating that their binding modes on STAT3 are significantly different. Notably, it is only a subtle structural difference in terms of a methoxy group in compound 10, indicating that this structural difference may be the cause of the different binding modes for compounds 6 and 10.

To determine the specificity of agents, mouse fibroblasts over-expressing the human EGF receptor (NIH3T3/hEGFR) were treated with the compounds and stimulated with EGF. Immunoblotting analysis shows treatment with 5 micromolar of compounds 6, 10 or 22 had no effects on EGF-induced pSTAT1 or pSTAT5, compared to effects on pSTAT3 (FIGS. 13A-13C). Further, similar treatment had little or no effects on pJAK2, pSrc, pS-Akt, pErk1/2, or suppressors of cytokine signaling (SOCS). For comparison, treatment of U251 MG cells with the known of sesquiterpene lactones, costinulide and parthenolide showed minimal effects on pY705STAT3.

Results so far show that agents do not inhibit protein tyrosine kinases (JAKs, pEGFR) or promote the induction of SOCS as a mechanism to suppress pY705STAT3 or STAT3 DNA-binding activity in tumor cells. To further investigate into the mechanism of inhibition of STAT3 induction, effects on protein tyrosine phosphates (PTPs) were determined. Immunoblotting analysis shows that treatment of U251MG cells with 5 micromolar of compounds 6, 10 or 22 had little or no effects on PTP1B levels (FIGS. 13A-13C). Moreover, immunoblotting analysis of whole-cell lysates from U251MG cells treated with 5 micromolar of compounds 6, 10 or 22 alone or in combination with 10-300 micromolar of the protein phosphaste inhibitor, sodium orthovanadate ($Na_2VO_4$) for 3 h shows ortho vanadate failed to overcome the inhibitory effect of the agents on intracellular pY705STAT (FIGS. 13A-13C), suggesting compounds 6, 10 or 22 may not induce PTPs as a mechanism to suppress pSTAT3. Instead, the potent inhibitory effects of agents (5 micromolar) countered the robust pY705STAT3 induction by orthovanadate alone. This indicates that agents may block the events leading up to pY705STAT3 induction.

Given the NMR and SPR results that agents directly interact with STAT3, which could potentially disrupt its activation and functions inside cells, we pursued a co-immunoprecipitation with immunoblotting analysis focusing on the interaction of STAT3 with the EGF receptor (EGFR). U251MG cells were treated with 6 for 0-3 h following which STAT3 was immunoprecipitated and immunoprobed for EGFR. The baseline STAT3 co-immunoprecipitation with EGFR was substantially diminished in response to the treatment with compound 6 for 0.5-3 h (FIG. 14), compare lanes 6, 9, and 12 to 3), suggesting the treatment with compound 6 disrupts the association of STAT3 with EGFR.

Some other types of sesquiterpene lactones, including parthenolide. (Wen, J., et al., Oxidative stress-mediated apoptosis. The anticancer effect of the sesquiterpene lactone parthenolide, J Biol Chem., 2002, 277: p. 38954-64) and costinulide (Butturini, E., et al., Two naturally occurring terpenes, dehydrocostuslactone and costunolide, decrease intracellular GSH content and inhibit STAT3 activation, PLoS One, 2011, 6(5): p. e20174) suppress the intracellular glutathione (GSH) pool. To determine if the isolated or synthesized compounds performed similarly, an investigation was performed to determine if the novel hirsutinolides could similarly alter glutathione levels. U251 MG cells were treated with compounds 6, 22 or costunolide as the positive control and assayed for glutathione levels. Unlike constinulide that suppressed GSH levels, treatment with compounds 6 or 22 did not repress GSH levels (FIG. 15).

Analysis of Proteomic Changes of STAT3 by the Purified and Synthesized Compounds.

To investigate the possibility that the hirsutinolides could induce global molecular changes in the sensitive malignant cells, lysates were prepared from U251 MG cells untreated or treated with 6 or 22 for 1 h and analyzed by isobaric peptide labeling and nanoLC-MS/MS analysis (iTRAQ) proteomics method (Ross, P. L., et al., Multiplexed protein quantitation in *Saccharomyces cerevisiae* using amine-reactive isobaric tagging reagents, Mol Cell Proteomics., 2004. 3: p. 1154-69), as described in the Examples section. A search was pursed of the 341,908 mass spectrometry spectra using ProteinPilot (version 4.5; Applied Biosystems) against the National Center for Biotechnology Information non-redundant reference sequence (NCBInr) human database and based on the criteria of choosing only proteins with at least 95% confidence and with a "Local False Discovery Rate" no higher than 5%, as calculated from the slope of the accumulated Decoy database hits by the PSPEP estimation. This search led to 3,498 highly confident protein identifications, 52 of which were considered significant based on the ProteinPilot program. Of these, 8 fell within the upper 1.3 (1×1.3) and lower 0.77 (1/1.3). Heat shock protein (Hsp) 70, vimentin and TNFα-induced protein 2 (TNAP2) were down 2- to 3-fold in cells treated with 6 only, translational activator GCN1, glucose-6-phosphate 1-dehydrogenase (G6PDH) isoform a, and thioredoxin reductase 1 (TX-NRD1) (cytoplasmic isoform 3) were down 2- to 3-fold in cells treated with 22 only, while microtubule-associated protein 1B (MAP1B) was down nearly 2-fold and importin subunit α-2 was up 2-fold in both treatment conditions. Immunoblotting analysis validated reduced expression of Hsp70 and vimentin, or GCN1 in cells treated with 6 or 22, respectively (FIG. 16).

Hirsutinolides Suppress Colony Survival, Induce Cell Cycle Arrest and Apoptosis, and Inhibit Migration of Glioma and Breast Cancer Cells Harboring Constitutively-Active STAT3

The effect of the isolated or synthesized compounds in a colony survival assay was performed. One-time treatment with 6, 10 or 22 induced a dose-dependent suppression of U251MG and MDA-MB-231 colony numbers, with significant decreases at 1 micromolar and higher (FIGS. 17A-17B, U251MG, MDA-MB-231). Compound 6 further induced substantial inhibition of MCF-7 colony numbers at 1 micromolar and higher, while 10 and 22 inhibited MCF-7 colony numbers at 2.5 micromolar or higher (FIGS. 17A-17B, MCF-7). Effect on SF295 occurred at 2.5 micromolar and higher (FIG. 17A-17B SF295). These studies suggest that both 10 and 22 have 2.5-fold preferential effects on the colony survival of U251MG and MDA-MB231 cells that harbor aberrantly-active STAT3 over MCF-7 cells that do not, while 6 is less specific in its effects.

Flow cytometry analysis further shows that treatment with compound 6 for 48 h induced cell cycle arrest at G2/M phase (FIG. 17B). Wound-healing assays showed treatment with 6, 10 or 22 for 19 h when cell viability is unaffected (FIG. 18B) suppressed the numbers of U251 cells migrating into the denuded area (FIG. 18A).

Compound (6) Inhibits Tumor Growth in Subcutaneous Human Glioblastoma and Breast Tumor Xenografts in Mice Compound 6 inhibited growth of mouse subcutaneous xenografts of human glioma U251MG and breast MDA-MB-231 tumors that harbor aberrantly-active STAT3 when administered via oral gavage (1 or 2 mg/kg, 100 µL, every day) (FIG. 19). No significant changes in body weights or obvious signs of toxicity, such as loss of appetite, decreased activity, or lethargy were observed.

The Results herein indicate that Vc-derived hirsutinolides are compounds with potent anti-tumor cell effects against human glioblastoma cells, and to a lesser extent, human breast cancer cells. Compounds 6, 7, 10, 20 and 22 are notable in their ability to suppress cell viability, colony formation and migration, and induce cell cycle arrest and apoptosis in both human glioma and breast cancer cells in vitro. As shown herein, compounds 10, 20 and 22 have more specific and preferential effects against glioma cells. Further, the antitumor efficacy demonstrated by compound 6 against human glioma in vivo in mouse subcutaneous xenograft provides proof of concept for the potential therapeutic application of the hirsutinolides.

That Vc-derived hirsutinolides, compounds 6, 7, 10, 20 and 22 modulate tumor cell phenotype indicates a common underlying mechanism for their antitumor cell-activities. The inhibition of aberrantly-active STAT3 in tumor cells represents one of the key potentially mechanisms for hirsutinolides to induce antitumor malignant effects. Using compounds 6 and 10, structural data was obtained indicating that the bioactive hirsutinolides directly interact with STAT3 and disrupt STAT3:STAT3 dimers. The results further indicate the disruption of STAT3 binding to receptors, such as EGFR, inside cells. These mechanisms contribute to the inhibition of STAT3 activity and STAT3-dependent gene transcription. There is a correlation between the inhibitory activities against STAT3 signaling, or the lack thereof, and the antitumor cell effects against human glioma and breast cancer cells that harbor abnormal STAT3 activity, or the lack thereof for the inactive agents.

BRIEF DESCRIPTION OF THE FIGURES

The patent application file contains at least one drawing executed in color. Copies of this patent or patent application publication with color drawing(s) will be provided by the Office upon request and payment of the necessary fee.

FIGS. 2A-2B depicts exemplary compounds investigated for anti-cancer activity.

FIGS. 7A-7S show NMR Data for compounds 1-4. S1. $^1$H NMR spectrum (400 MHz, $CDCl_3$) of Compound 1, S2. $^{13}$C NMR spectrum (100 MHz, $CDCl_3$) of Compound 1, S3. $^1$H-$^{13}$C HSQC NMR spectrum ($CDCl_3$) of Compound 1, S4. $^1$H-$^{13}$C HMBC NMR spectrum ($CDCl_3$) of Compound 1, S5. NOESY spectrum ($CDCl_3$) of Compound 1, S6. $^1$H NMR spectrum (400 MHz, $CDCl_3$) of Compound 2, S7. $^{13}$C NMR spectrum (100 MHz, $CDCl_3$) of Compound 2, S8. $^1$H-$^{13}$C HSQC NMR spectrum ($CDCl_3$) of Compound 2, S9. $^1$H-$^{13}$C HMBC NMR spectrum ($CDCl_3$) of Compound 2, S10. NOESY spectrum ($CDCl_3$) of Compound 2, S11. $^1$H NMR spectrum (400 MHz, $CD_3OD$) of Compound 3, S12. $^{13}$C NMR spectrum (100 MHz, $CD_3OD$) of Compound 3, S13. $^1$H-$^{13}$C HSQC NMR spectrum ($CD_3OD$) of Compound 3, S14. $^1$H-$^{13}$C HMBC NMR spectrum ($CD_3OD$) of Compound 3, S15. NOESY spectrum ($CD_3OD$) of Compound 3, S16. $^1$H NMR spectrum (400 MHz, $CDCl_3$) of Compound 4, S17. $^{13}$C NMR spectrum (100 MHz, $CDCl_3$) of Compound 4, S18. $^1$H-$^{13}$C HSQC NMR spectrum ($CDCl_3$) of Compound 4, S19. $^1$H-$^{13}$C HMBC NMR spectrum ($CDCl_3$) of Compound 4, S20. NOESY spectrum ($CDCl_3$) of Compound 4.

FIGS. 9A-9F show the viability of cells after exposure to purified hirsutinolide compounds, demonstrating that the compounds suppress viability of glioblastoma and breast cancer cells. CyQuant cell proliferation assay and the effects of 72-h treatment with (A-E) active hirsutinolide natural products 6, 7, 10, 20 and 22 on human glioma (U251MG, U373MG, and SF295) and breast cancer (MDA-MB-231) cells harboring activated STAT3, or normal mouse fibroblasts (NIH3T3) that do not; (F) weakly-active hirsutinolides, 8, 9, 11 and 18 on human glioma (U251MG) cells.

FIGS. 11A-11D show the Effect of hirsutinolides on STAT3 activation in tumor cells. U251MG or MDA-MB-231 cells treated with (A and B) 5 micromolar of more active (A) or weakly-active (B) natural products for the 0-2 h and whole-cell lysates of equal total protein prepared and subjected to immunoblotting analysis for pY705STAT3, STAT3, β-actin or GAPDH (A(i) and B)) or nuclear extracts of equal total protein prepared and subjected to STAT3 DNA-binding with EMSA analysis (A(ii)); or (C) increasing concentration of 6, 10, or 22 for 2 h and whole-lysates of equal total protein prepared and subjected immunoblotting analysis for pY705STAT3, STAT3, or GAPDH; or (D) the designated semi-synthesized analogs of 22 for 0-24 h and subjected to immunoblotting analysis for pY705STAT3, STAT3, or β-actin. Positions of STATs:DNA complexes or proteins in gel are labeled; control lanes (0) represent nuclear extracts or whole-cell lysates prepared from 0.05% DMSO-treated cells. Data are representative of at least three to four independent determinations.

FIGS. 13A-13C show analyses of STAT1, STAT3, STAT5, Akt, Erk1/2, JAK2, SOCS, and PTP1B activation or STAT3-EGFR association and the effects of active hirsutinolides and sodium orthovanadate. (A-C) SDS-PAGE and Western blotting analysis of whole-cell lysates of equal total protein prepared from (A) EGF-stimulated NIH3T3/hEGFR cells pre-treated with the 5 micromolar of the designated agents for 24 h and probing for pY705STAT3, STAT3, pY701 STAT1, STAT1, pY694STAT5, STAT5 or GAPDH, or the human glioma, U251MG cells treated with 5 micromolar of the designated inhibitors for (B) 0-32 h and probing for pS-Akt, Akt, pErk1/2, Erk1/2, pJAK2, JAK2, SOCS3, PTP1B, pSTAT3, STAT3, β-actin or GAPDH; or (C) 3 h in the absence or presence of increasing concentration of $Na_3VO_4$ and probing for pSTAT3, STAT3 or GAPDH/.

FIGS. 17A-17B show that purified hirsutinolide compounds inhibit colony survival, induce cell cycle arrest and apoptosis and inhibit cell migration in vitro: (A) Cultured human glioma (U251MG and SF295) and breast (MDA-MB-231) cancer cells that harbor constitutively-active STAT3, and the human breast cancer MCF-7 cells that do not were seeded as single-cells and treated once with 0-5 μM of the indicated hirsutinolides and allowed to culture until large colonies were visible, which were stained with crystal violet and imaged; (B) cell cycle distribution analysis of human glioma U251MG cells treated or untreated with 5 micromolar of the designated compounds for 48 h and processed by propidium iodide (PI) staining and analyzed by flow cytometry for DNA content.

EXAMPLES

Figure 1:
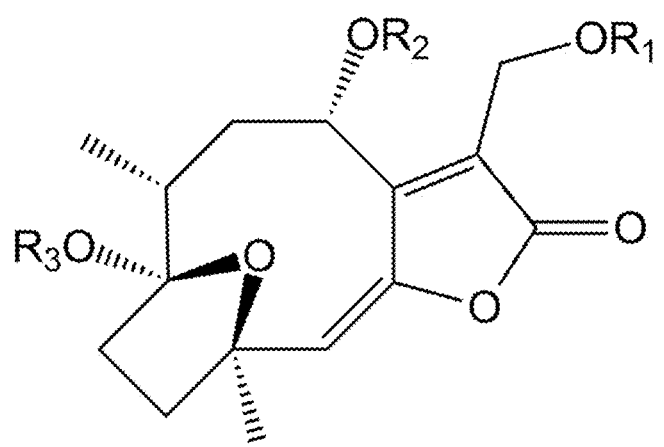
FIG. 1 shows the general structure (Formula I) of compounds investigated for anti-cancer activity.
Figure 2B:
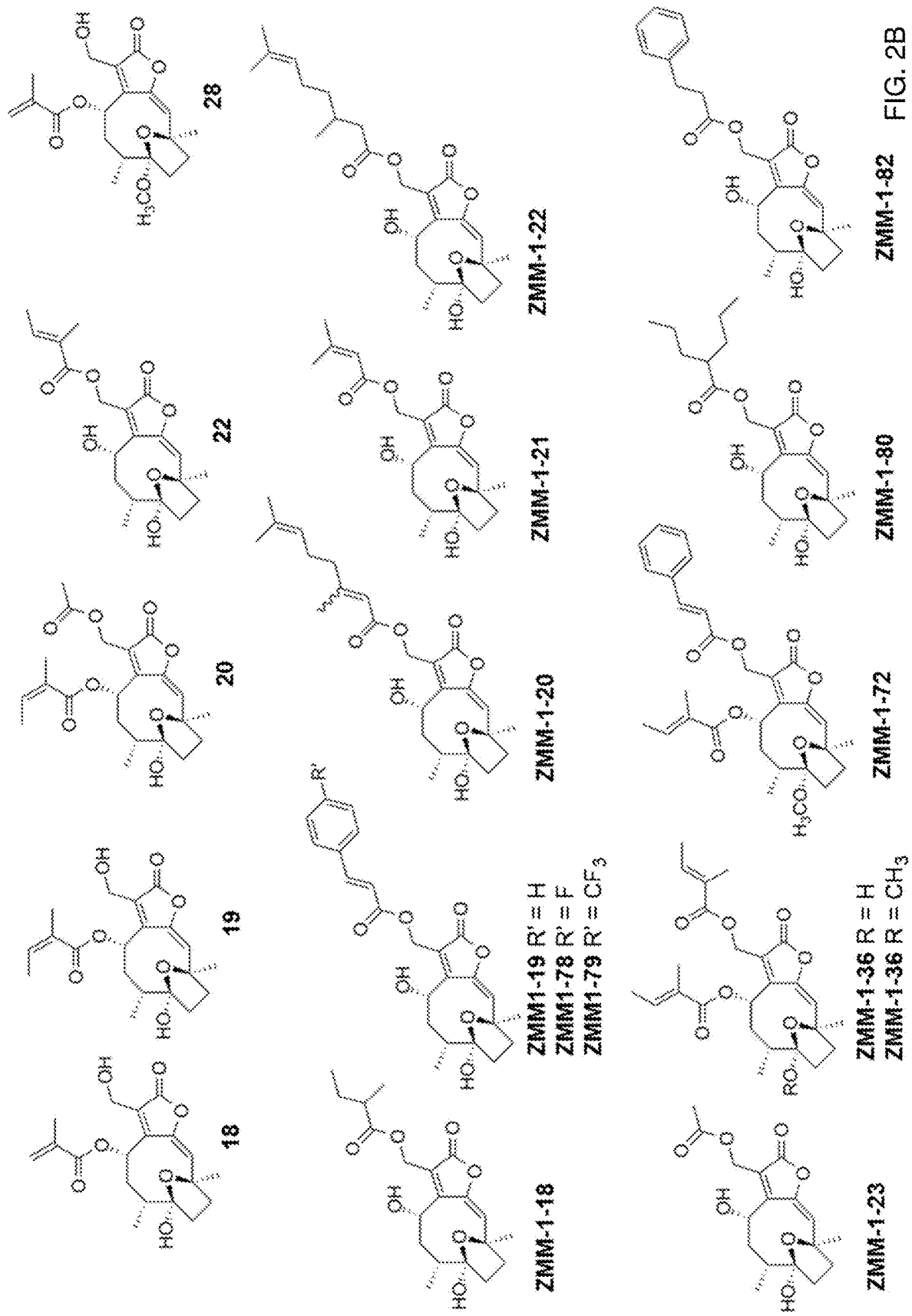

The invention is now described with reference to the following Examples. These Examples are provided for the purpose of illustration only, and the invention is not limited to these Examples, but rather encompasses all variations that are evident as a result of the teaching provided herein.

The Examples below demonstrate that the potent and selective STAT-3 inhibitors of Formula I have efficacy for treating cancer. Aspects and embodiments of the instant disclosure stem from the unexpected result that certain STAT-3 inhibitor formulations have surprising, and unexpected, utility and efficacy when administered to a subject cell type.

The therapeutically effective STAT-3 inhibitors of this invention can be prepared according to the synthetic scheme outlined above, or via the specific extraction method as described below. However, the invention is not limited to those methods. The compositions may also be prepared as described for structurally related compounds in the literature.

General Experimental Procedures.

Optical rotations were measured on a Rudolph Research Autopol IV multiwavelength polarimeter. UV spectra were run on a Shimadzu PharmaSpec-1700 UV-visible spectrophotometer. CD spectra were recorded on a JASCO J-815 spectropolarimeter. IR spectra were measured on a Bruker Tensor-27 FT-IR spectrometer. NMR spectroscopic data were recorded at room temperature on a Bruker Avance DRX-400 spectrometer, and the data were processed using TopSpin 3.1 software. High-resolution electrospray ionization mass spectra (HRESIMS) were obtained with an Agilent 6530 LC-qTOF High Mass Accuracy mass spectrometer operated in the positive- and negative-ion modes. Analytical TLC was performed on 0.25 mm thick silica gel $F_{254}$ glass-backed plates (Sorbent Technologies). Column chromatography was carried out with silica gel (230-400 mesh; Sorbent Technologies) and RP-18 (YMC GEL ODS-A, 12 nm, S-150 μm) were used for column chromatography. Semipreparative (10×150 mm) columns were used for semipreparative HPLC, and was conducted on a Beckman Coulter Gold-168 system equipped with a photodiode array detector using an Alltech reversed-phase Econosil C-18 column (10 μm, 10×250 mm) with a flow rate of 1.5 mL/min.

Plant Material.

The leaves and stems of *V. cinerea* were provided by Lampang Herb Conservation Club, Lampang Province, Thailand, in May 2011. Plant identification was confirmed by comparison with voucher specimen at the Forest Herbarium, Bangkok, Thailand.

Cell Lines and Reagents.

Normal mouse fibroblasts (NIH3T3) and counterparts transformed by v-Src (NIH3T3/v-Src) or overexpressing the human EGF receptor (NIH3T3/hEGFR), and the human breast cancer (MDA-MB-231) cells have all been previously reported. (Turkson, J., et al., Phosphotyrosyl peptides block STAT3-mediated DNA-binding activity, gene regulation and cell transformation, J. Biol. Chem., 2001, 276: p. 45443-45455; Garcia, R., et al., Constitutive activation of STAT3 by the Src and JAK tyrosine kinases participates in growth regulation of human breast carcinoma cells, Oncogene, 2001, 20: p. 2499-2513; Johnson, P. J., et al., Overexpressed pp60c-src can induce focus formation without complete transformation of NIH 3T3 cells, Mol. Cell. Biol., 1985. 5: p. 1073-1083). These cells were grown in Dulbecco's modified Eagle's medium (DMEM) containing 10% heat-inactivated fetal bovine serum (FBS). The human glioma lines, U251MG, U373MG and U87MG (Sigma-Aldrich Corporation, St. Loius, Mo.) and SF-295 (DCTD Tumor Repository of the National Cancer Institute, Frederick, Md.) were obtained from the designated sources. The glioma cells were cultured in Roswell Park Memorial Institute (RPMI) medium-1640 supplemented with 10% FBS.

Example 1

Immunoprecipitation and SDS-PAGE/Western Blotting Analysis

These studies were performed as previously reported. (Xu, Y., et al., Targeting STAT3 suppresses growth of U251 cell-derived tumours in nude mice, J Clin Neurosci., 2012, 19: p. 443-6.) Whole-cell lysates preparation, immunoprecipitation and immunoblotting analysis were performed. Lysates of equal total protein prepared in the lysis buffer (50 mM Hepes, pH 7.5, 150 mM NaCl, 2 mM EDTA, 1% Triton X-100, 0.1% SDS), were subjected to IP or Western blotting analysis. Antibodies against STAT3, pY705STAT3, Src, pY416Src, Erk1/2, and pT202/Y204Erk1/2 and GAPDH (Cell Signaling Technology, Danvers, Mass.), and anti-β-actin, and HSP105 (Santa Cruz Biotechnology, Dallas, Tex.) are from the designated sources.

Example 2

Nuclear Extract Preparation and Gel Shift Assays

Nuclear extract preparations and DNA-binding/electrophoretic mobility shift assay (EMSA) were carried out as previously described (Xu, supra). Nuclear extract preparations and DNA-binding activity/electrophoretic mobility shift assay (EMSA) were carried out as previously described. U251 MG and MDA-MB-231 cells culture were pretreated with different concentrations of the compounds for the indicated period and then harvested for nuclear extract preparation and DNA-binding assay with EMSA analysis. The $^{32}$P-labeled oligonucleotide probe used was hSIE (high-affinity sis-inducible element) from the c-fos gene, m67 variant (5'-AGCTTCATTTCCCGTAAATC-CCTA-3') that binds STAT3. Except where indicated, nuclear extracts were pre-incubated with compound for 30 min at room temperature prior to incubation with the radiolabeled probe for 30 min at 30° C. before subjecting to EMSA analysis. Where appropriate, bands corresponding to DNA-binding activities were scanned and quantified for each concentration of compound using ImageJ and plotted as percent of control (vehicle) against concentration of compound, from which the $IC_{50}$ values were derived.

Example 3

Measurement of GSH and GSSG

Reduced glutathione (GSH) and oxidized glutathione disulfide (GSSG) levels were assayed using a commercially available kit (Cayman Chemical, Ann Arbor, Mich.) and following the manufacturer's instructions.

Example 4

Nuclear Magnetic Resonance (NMR) Studies and Sample Preparation

The plasmid expressing the human STAT3β encompassing residues 127-711 was constructed by inserting the cDNA into the pET28+ expression vector between the NcoI site and the histidine tag. The plasmid was transformed into E. coli BL21 (DE3) strains (CodonPlus-RIL and TKB1) for protein expression. The transformed E. coli were initially grown in 1 L terrific broth (TB) at 37° C. into the end of the log phase, washed with 1 L M9 media lacking NMR isotopes and then rehydrated in 250 mL M9 media containing 0.25 g $^{15}NH_4Cl$, 1 g [$D_7$]-glucose, 100% $D_2O$, 2.5 g [$D_4$]-succinic acid, and the sodium salts of 60 mg [$^{13}CH_3$; 3,3-$D_2$]-alpha-ketobutyric acid and 100 mg [3-$^{13}CH_3$; 3,4,4,4-$D_4$]-alpha-ketoisovaleric acid. All isotopes were purchased from Cambridge Isotope Laboratories (Tewksbury, Mass.). Cells were allowed to recover for 1 hour in the M9 media prior to addition of 0.5 mM isopropyl β-D-1-thiogalactopyranoside (IPTG) for 24 hours at 20° C. to induce uSTAT3 expression. This way, the side chain methyl groups of IVL residues of the STAT3 protein were selectively $^{13}C/^1H$ labelled, while rest of the protein was $^{12}C/^2H$ labeled.

Soluble His-tagged STAT3 (127-711-His$_6$) was purified by nickel affinity chromatography (Ni-NTA agarose from Qiagen, Valencia, Calif.). The STAT3 eluent was exchanged into sample buffer at pH 5.5 containing 10 mM MES buffer, 2 mM TCEP and 0.03% sodium azide. NMR samples contained deuterated versions of all buffer reagents in 100% $D_2O$. Protein sample concentrations were determined by Bradford Assay (BioRad Laboratories, Hercules, Calif.) and by UV absorbance at 280 nm.

Example 5

NMR Studies of the Interaction with Compounds

NMR samples contained 20 micromolar STAT3, 10 mM MES, pH 5.5, 0.5 mM TCEP in 100% D2O. All spectra were collected at 308K using the IconNMR module of Topspin 3.1 on a Bruker 700 MHz NMR spectrometer equipped with a cryogenic probe (Bruker BioSpin, Karlsruhe, Germany). $^1H$-$^{13}C$ correlation spectra for methyl-labeled STAT3 were obtained using the 2D $^1H$-$^{13}C$ HMQC experiment to monitor the interaction between STAT3 and compounds. Spectra were processed by NMRPipe and analyze by NMRView. Isoleucines were unambiguously assigned by comparison of STAT3 spectra with Ile-to-Leu mutants. Incremental additions of compounds were made to the STAT3 samples. All compounds were dissolved in the same buffer as that of STAT3. Compound concentrations at 100 micromolar and 200 micromolar were used in the interaction study.

Example 6

Isobaric Peptide Labeling and nanoLC-M/MS Analysis (iTRAQ)

Cellular samples were prepared according to the Pennsylvania STATe University College of Medicine Mass Spectrometry and Proteomics Core (MSPC) facility (Hershey, Pa.) standard protocol, adapted from the manufacturer's instructions (Applied Biosystems Sciex, Foster City, Calif.), combined with filter-aided sample preparation, as previously reported. ([Wiśniewski, J. R., et al., Universal sample preparation method for proteome analysis. Nat Methods, 2009, 6: p. 359-62). For iTRAQ analysis (Ross, P. L., et al., Multiplexed protein quantitation in *Saccharomyces cerevisiae* using amine-reactive isobaric tagging reagents, Mol Cell Proteomics., 2004, 3: p. 1154-69), one hundred micrograms of whole-cell lysates from U251 MG cells untreated (DMSO control) or treated with 5 micromolar of compounds 22 or 6 for 1 h were independently digested, and their corresponding cellular proteins were differently labeled with 114, 115 or 117 tags, respectively, using iTRAQ reagents. Dried, labeled peptides were then reconstituted and subjected to ion exchange chromatography. A total of 8 fractions were separated on an Eksigent ChipLC and nanosprayed into a 5600 TripleTOF mass spectrometer at the MSPC facility. Protein identification and quantification for iTRAQ samples were carried out using ProteinPilot™ software (version 4.5; Applied Biosystems, MDS-Sciex, Framingham, Mass.). Only proteins identified with at least 95% confidence and with "Local False Discovery Rate" no higher than 5%, as calculated from the slope of the accumulated Decoy database hits by the Proteomics System Performance Evaluation Pipeline (PSPEP) estimation (Tang, W. H., I. V. Shilov, and S. L. Seymour, Nonlinear fitting method for determining local false discovery rates from decoy database searches. J Proteome Res, 2008, 7: p. 3661-7) were selected.

Example 7

Colony Survival Assay

This assay was performed as previously reported (Xu, Y., supra). The assay was performed as previously reported. Briefly, cells were seeded as single-cell in 6-well plates (250 cells per well), treated once the next day with compounds for 72 h, and allowed to grow until large colonies were visible. Colonies were stained with crystal violet for 4 h and counted with FluorChem imaging system (Protein Simple, Santa Clara, Calif.).

Example 8

Cell Cycle Analysis and Apoptosis Assay

Cells in subconfluent cultures were treated with DMSO or compound for the indicated times, processed, and analyzed by flow cytometry for cell cycle profile or apoptosis. Cells in subconfluent cultures were treated with DMSO or compound for the indicated times. For cell cycle analysis, samples were prepared according to the manufacturer's (BD Biosciences, Franklin Lake, N.J.) instructions. Cells were fixed in 70% ice cold ethanol and stored in −20° C. The stored cells were washed twice with ice-cold phosphate-buffered saline (PBS) and resuspended in propidium iodide (PI)/RNAse staining buffer (BD Biosciences). After incubation at room temperature in darkness for 15 min, the samples were analyzed with BD Accuri C6 flow cytometer and software (BD Biosciences).

Example 9

Wound Healing Assay for Migration

This assay was performed as previously reported. (Xu, Y., supra). Briefly, subconfluent cultures of U251MG cells in 6-well plates were wounded using pipette tips and treated with compound or vehicle (DMSO) and allowed to migrate into the denuded area over a 19 h period. The migration of cells was visualized at a 10× magnification using an Axiovert 200 inverted fluorescence microscope (Zeiss), with pictures taken using a mounted Canon Powershot A640 digital camera.

Example 10

Mice and In Vivo Tumor Studies

Six-week-old female athymic nude mice were purchased from Taconic (Renssealer, N.Y.) or Jackson (Indianapolis, Ind. or Bar Harbor, Nebr.) Laboratories and maintained in the institutional animal facilities approved by the American Association for Accreditation of Laboratory Animal Care. Athymic nude mice were injected s.c. in the left flank area with $3.5 \times 10^6$ human breast cancer, MDA-MB-231 cells in 100 μL PBS or $6.5 \times 10^6$ U251MG glioblastoma cells in 200 μL of equal mixture of PBS and Matrigel. After 5-11 days, tumors of a 30-100 mm³ volume were established. Animals with established tumors were grouped, so that the mean tumor sizes in all groups were nearly identical, and then given compound 6, 2 mg/kg (oral gavage, 100 μL) three times a week for 25 or 78 days. Animals were monitored daily, tumor sizes were measured with calipers, and body weights were taken every 3 or 7 days. Tumor volumes were calculated according to the formula $V=0.52 \times a2 \times b$, where a is the smallest superficial diameter and b is the largest superficial diameter. For each treatment group, the tumor volumes for each set of measurements were STATistically analyzed in comparison with the control (vehicle-treated) group using a paired t test.

Statistical Analysis.

Statistical analysis was performed on mean values using Prism GraphPad Software, Inc. (La Jolla, Calif.). The significance of differences between groups was determined by the paired t-test at $p<0.05^*$, $<0.01^{}$, and $<0.001^{*}$.

Example 11

Process for the Purification of Natural Compounds from *Vernonia cinerea*

The air-dried and finely ground combination of the leaves and stems of *V. cinerea* (10 kg) was extracted by maceration in MeOH (3×40 L) at room temperature. The solvent was concentrated in vacuo to yield 2 kg of a crude extract, which was then suspended in distilled water (4 L) and then extracted successively with $CHCl_3$ (3×4 L), EtOAc (3×4 L), and n-butanol (3×4 L). The $CHCl_3$-soluble extract (300 g), was separated by column chromatography over Si gel (CC; ϕ 20 cm; 230-400 mesh, 5 kg) using a gradient solvent system of n-hexane-EtOAc (100:1 to 0:100), to afford 16 fractions (C1-C16). Fraction C2 (78 g) was subjected to Si gel (CC; ϕ 10 cm; 230-400 mesh, 1 kg), with n-hexane- EtOAc (100:0 to 1:1) as the solvent system, yielding fifteen subfractions (C2.1 to C2.15). Subfraction C2.14 (2.0 g) was chromatographed over an open $C_{18}$ (400 g) column and eluted with $H_2O$-MeOH mixtures (90:10 to 100% MeOH), to afford three subfractions (C2.14.1 to C2.14.3). Subfraction C2.14.1 (0.1 g) was purified by HPLC on a semi-preparative RP-18 column, using MeOH—$H_2O$ mixtures (60:40 to 0:100) as the solvent system, to yield, in turn, 2 (1.5 mg, $t_R$ 115 min), 10 (4 mg, $t_R$ 120 min), and 9 (4 mg, $t_R$ 122 min). Subfraction C2.15 (4.0 g) was chromatographed on an open $C_{18}$ (400 g) column and eluted with $H_2O$-MeOH (90:10 to 100% MeOH), to afford four subfractions (C2.15.1 to C2.15.4). Subfraction C2.15.1 (0.1 g) was subjected to separation on a semipreparative RP-18 column by HPLC, using MeOH—$H_2O$ mixtures (60:40 to 0:100) as solvent system, to yield 1 (3 mg, $t_R$ 95 min), 5 (10 mg, $t_R$ 97 min), 12 (8 mg, $t_R$ 100 min), and 6 (30 mg, $t_R$ 105 min). Subfraction C2.15.2 (0.15 g) was subjected to semipreparative HPLC (MeOH—$H_2O$=50:50 to 0:100), to yield 4 (2.5 mg, $t_R$ 88 min), 8 (3 mg, $t_R$ 90 min), 11 (10 mg, $t_R$ 93 min), and 7 (30 mg, $t_R$ 100 min). Fraction C14 (10 g) was chromatographed on a Sephadex LH-20 gel (300 g) column and eluted with $H_2O$-MeOH (100:0 to 50:50) solvent system, to afford nine subfractions (C14.1 to C14.9). Compound 3 (2 mg, $t_R$ 90 min) was purified from subfraction C14.3 (0.1 g) by semipreparative RP-18 column and HPLC methods, using (MeOH—$H_2O$=50:50 to 80:20) as solvent system. Subfractions C2.14.1 and C2.14.2 (0.8 g) were purified by HPLC on a semipreparative RP-18 column, using MeOH—$H_2O$ mixtures (60:40 to 0:100) as the solvent system, to yield, in turn, 10 (102 mg, $t_R$ 78 min), 2 (1.5 mg, $t_R$ 115 min), 12 (6 mg, $t_R$ 122 min), 13 (3 mg, $t_R$ 123 min), and 9 (4 mg, $t_R$ 125 min). Subfraction C2.15 (4.0 g) was chromatographed on an open $C_{18}$ (400 g) column and eluted with $H_2O$-MeOH (90:10 to 100% MeOH), to afford four subfractions (C2.15.1 to C2.15.4). Subfraction C2.15.1 (0.4 g) was subjected to separation on a semipreparative RP-18 column by HPLC, using MeOH—$H_2O$ mixtures (60:40 to 100:0) as solvent system, to yield 5 (10 mg, $t_R$ 85 min), 1 (3 mg, $t_R$ 95 min), 14 (5 mg, $t_R$ 97 min), and 6 (30 mg, $t_R$ 105 min). Subfraction C2.15.2 (0.5 g) was subjected to semipreparative HPLC (MeOH—$H_2O$=50:50 to 100:0), to yield 4 (2.5 mg, $t_R$ 88 min), 15 (8 mg, $t_R$ 90 min), 8 (3 mg, $t_R$ 100 min), 11 (10 mg, $t_R$ 93 min), and 7 (30 mg, $t_R$ 105 min). Fraction C14 (10 g) was chromatographed on a Sephadex LH-20 gel (300 g) column and eluted with $H_2O$-MeOH (100:0 to 50:50) solvent system, to afford nine subfractions (C14.1 to C14.9). Compound 3 (2 mg, $t_R$ 90 min) was purified from subfraction C14.3 (0.1 g) by semipreparative RP-18 column and HPLC methods, using (MeOH—$H_2O$=50:50 to 80:20) as solvent system. Compound 16 (10 mg) was crystallized in MeOH—$CHCl_3$ (1:2) from the subfraction C15.

Figure 6:
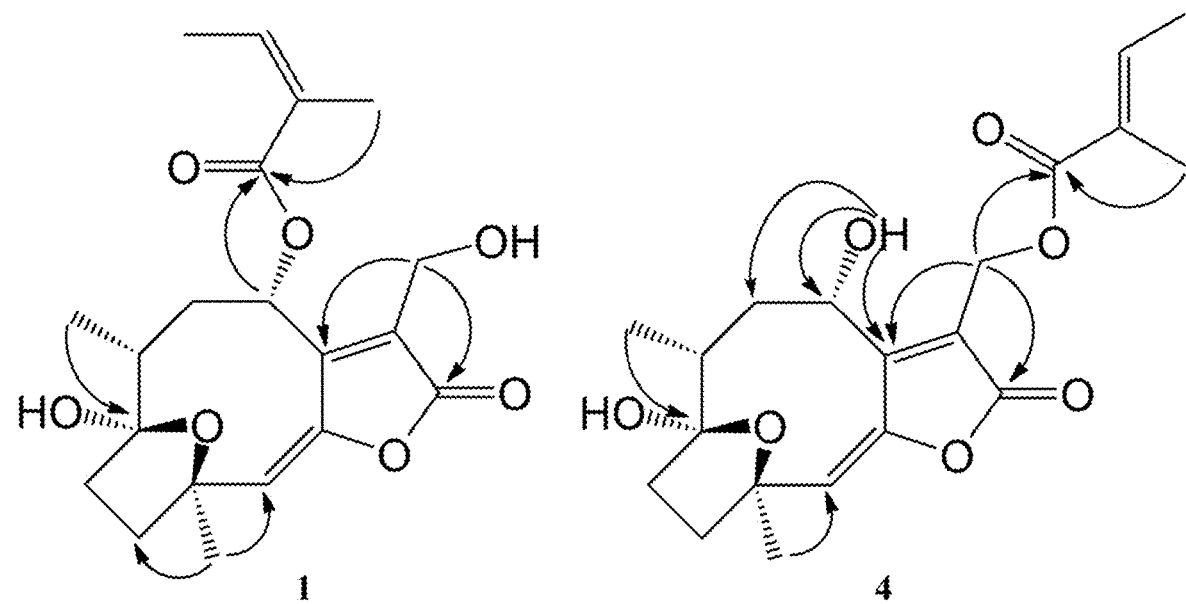
FIG. 6 shows HMBC correlations of compounds 1 and 4.
Figure 8:
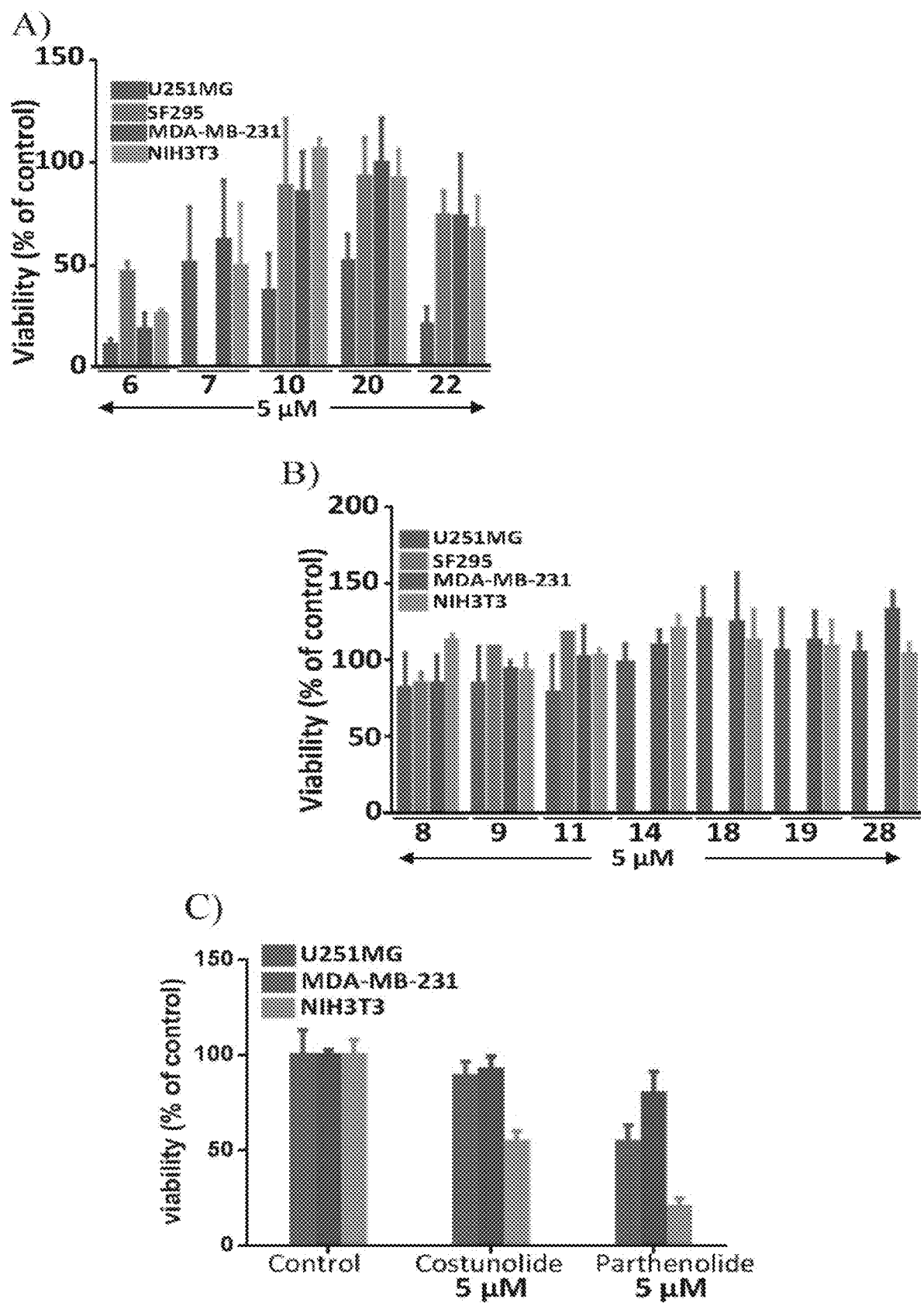
FIGS. 8A-8C show the viability of cells after exposure to Compounds 6-28.
Figure 10:
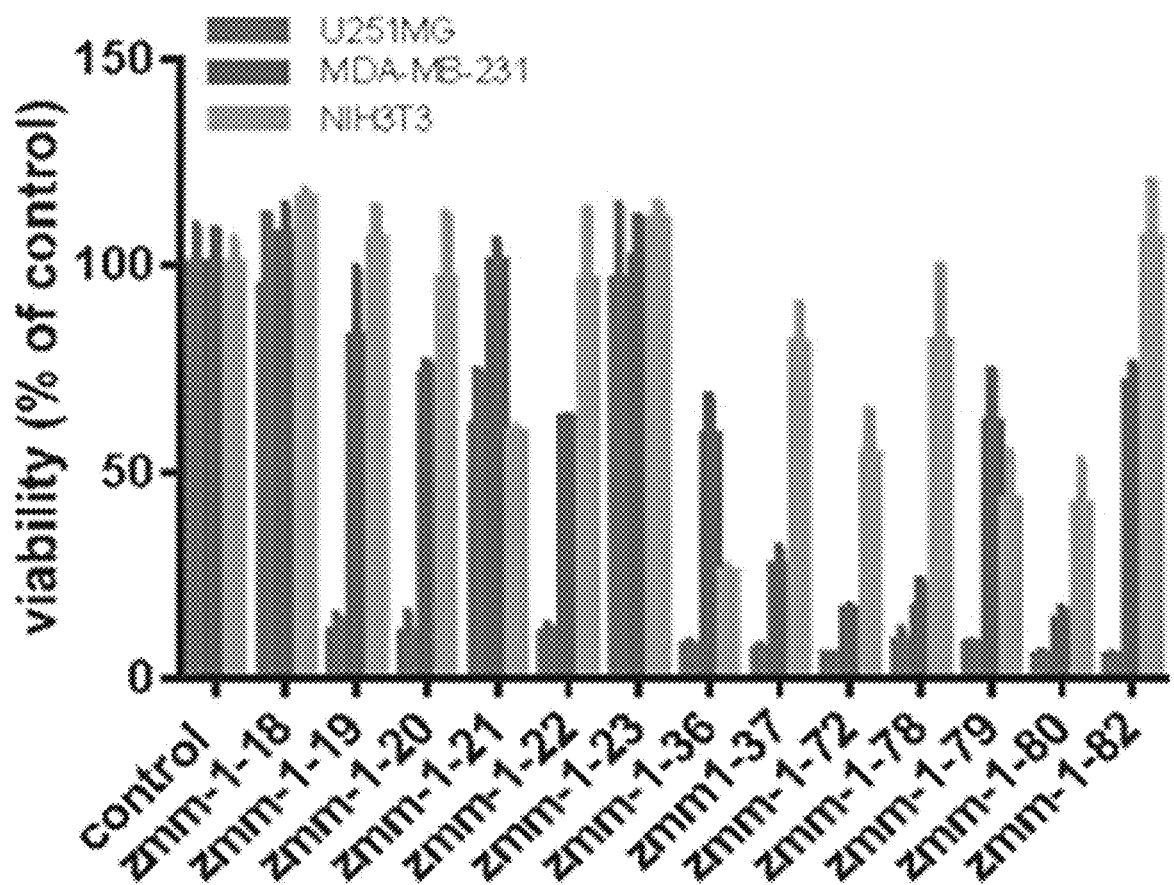
FIG. 10 shows the results of the CyQuant cell proliferation assay and the effects of 72-h treatment with the synthesized analogs of 22, zmm-1-18, 1-19, 1-20, 1-21, 1-22, 1-23, 1-36, 1-37, 1-72, 1-78, 1-79, 1-80, and 1-82. $IC_{50}$ values were derived from the graphical representations. Values are the mean and S.D. of 3-4 independent determinations.
Figures 11C, 11D:
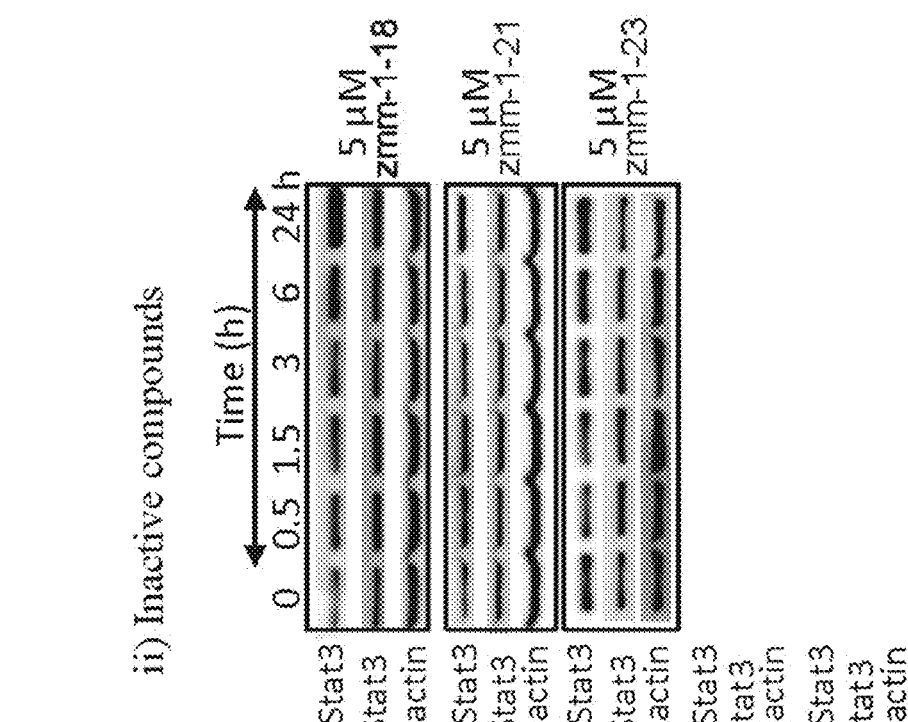
Figure 12:
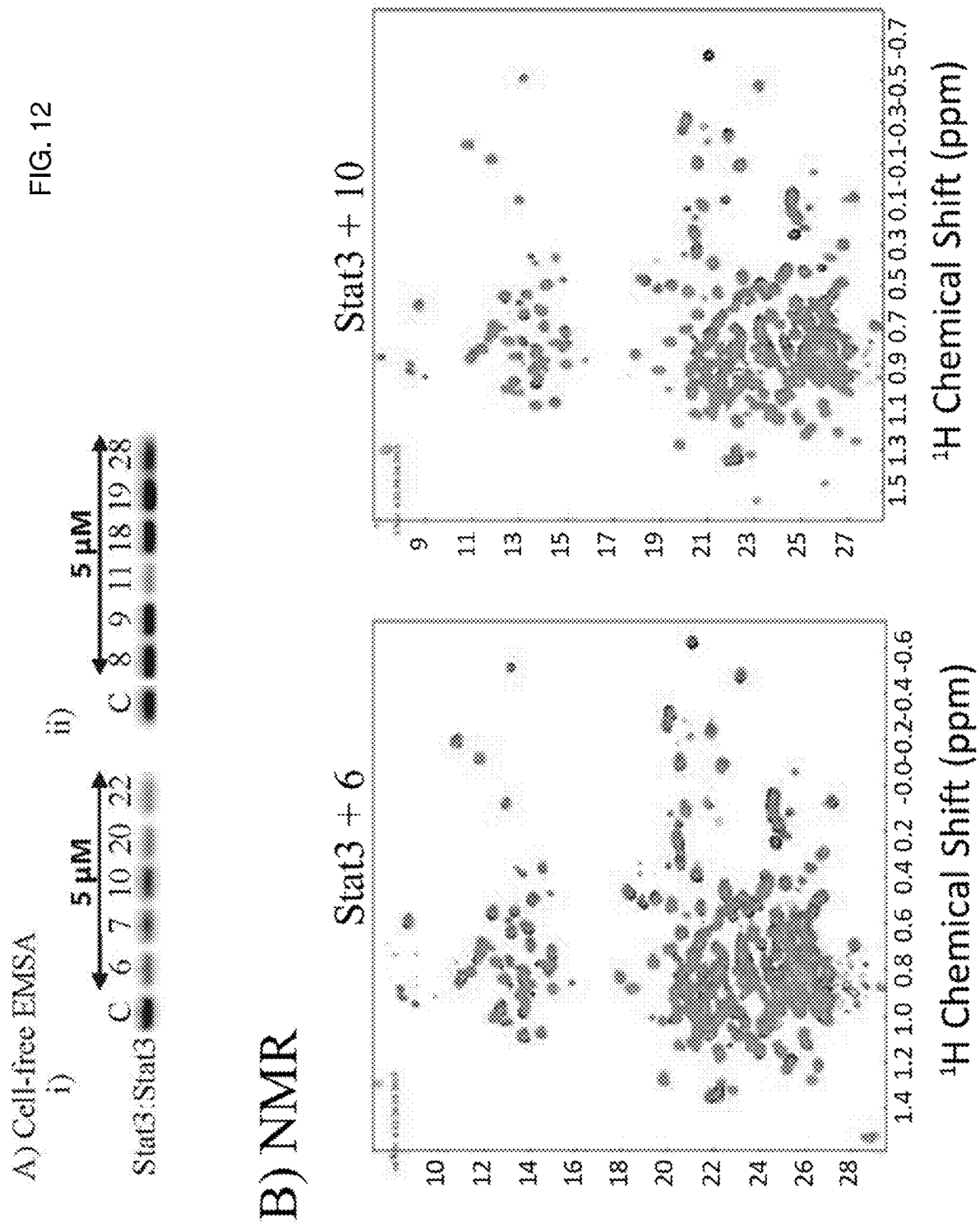
FIGS. 12A-12B show that purified hirsutinolide compounds interact with STAT3 and inhibit STAT3 DNA-binding activity in vitro (A) Nuclear extracts of equal total protein containing activated STAT3 were pre-incubated with or without of 5 micromolar of the designated inhibitors for 30 min at room temperature prior to the incubation with the radiolabeled hSIE probe that binds STAT3 and subjecting to EMSA analysis; and (B) nuclear magnetic resonance (NMR) analysis of the interactions of STAT3 in solution with compound 6 or 10 and the observed chemical shifts of isoleucine residues of the STAT3 protein. Data are representative of 2-3 independent determinations.
Figure 14:
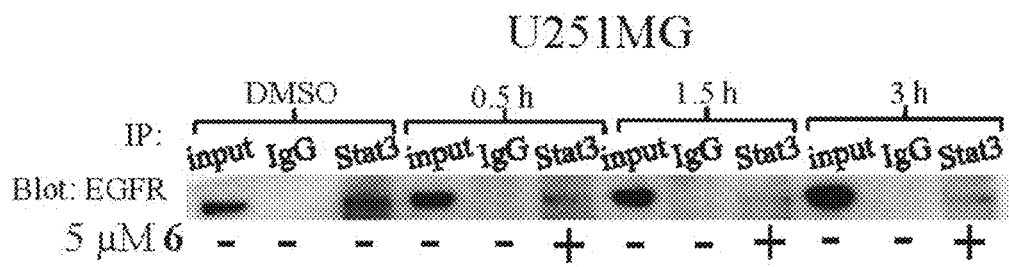
FIG. 14 shows Immunoblots of EGFR from STAT3 immune-complexes prepared from U251 MG cells treated with 5 micromolar of compound 6 for the indicated times. Positions of proteins in gel are labeled; control lane (0) represents whole-cell lysates prepared from 0.025% DMSO-treated cells. Data are representative of 3-4 independent determinations.
Figure 15:
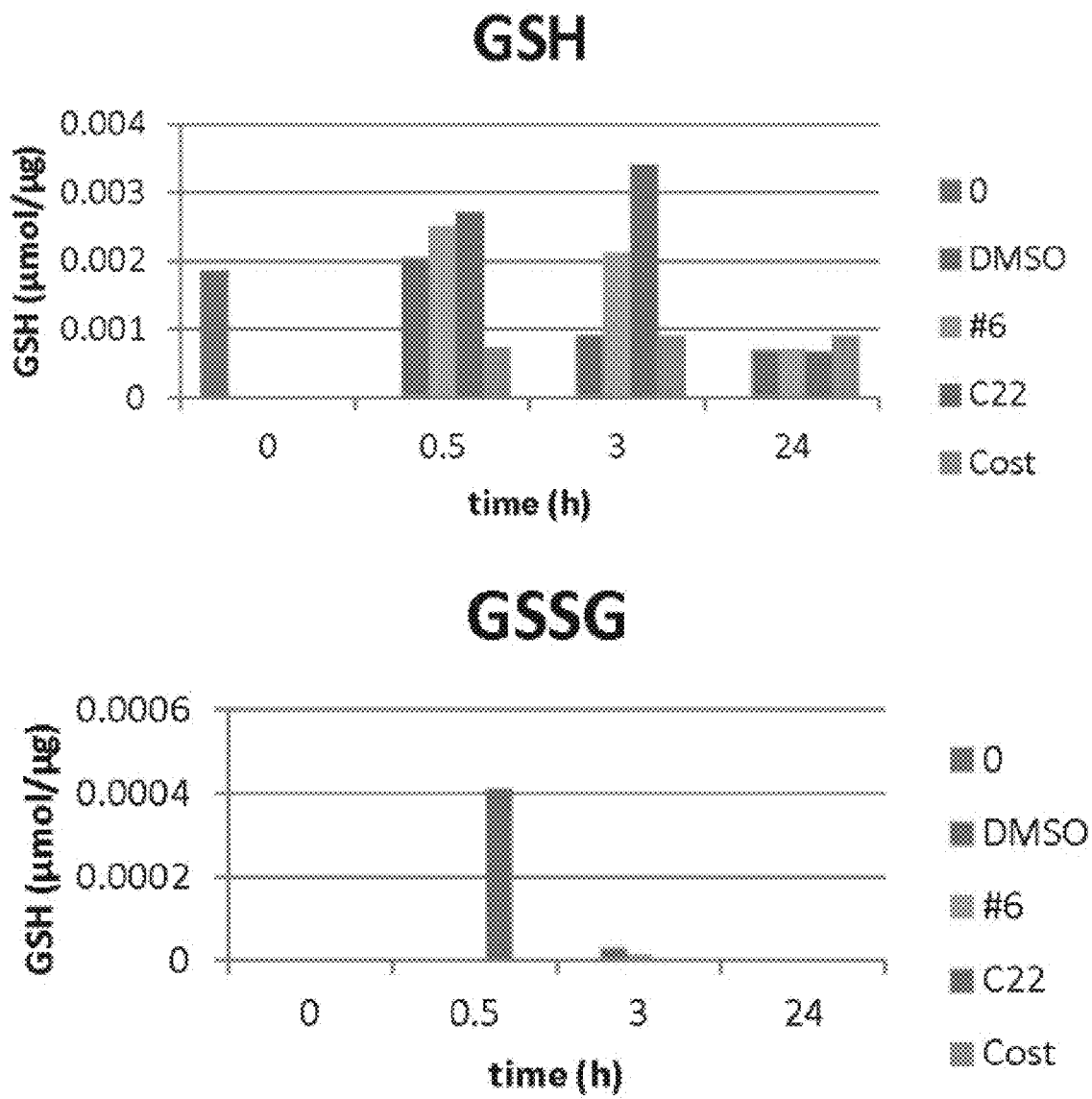
FIG. 15 shows a lack of suppression of GSH levels
Figure 16:
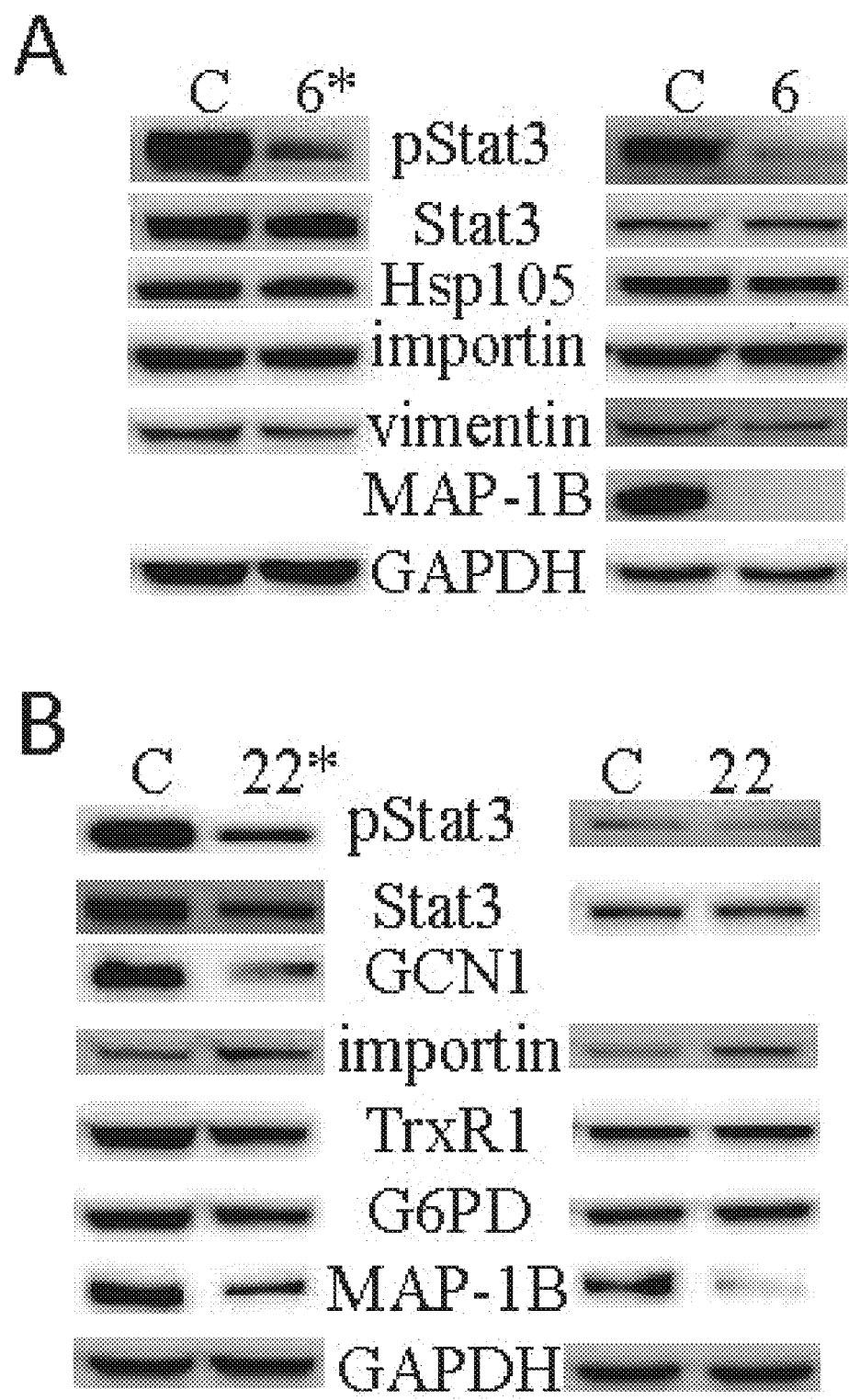
FIG. 16 shows immunoblotting analysis of pSTAT3, STAT, Hsp105, importin, vimentin, GCN1, and microtubule-associated protein (MAP)-1B: (A and B) SDS-PAGE and Western blotting analysis of whole-cell lysates preparation from U251MG cells treated with 6 or 22 for the indicated times and probing for pSTAT3, STAT, Hsp105, improtin, vimentin, GCN1, MAP-1B, or GAPDH. Positions of proteins in gel are labeled; control lane (c) represents whole-cell lysates prepared from 0.025% DMSO-treated cells. Data are representative of 3 independent determinations.
Figure 18:
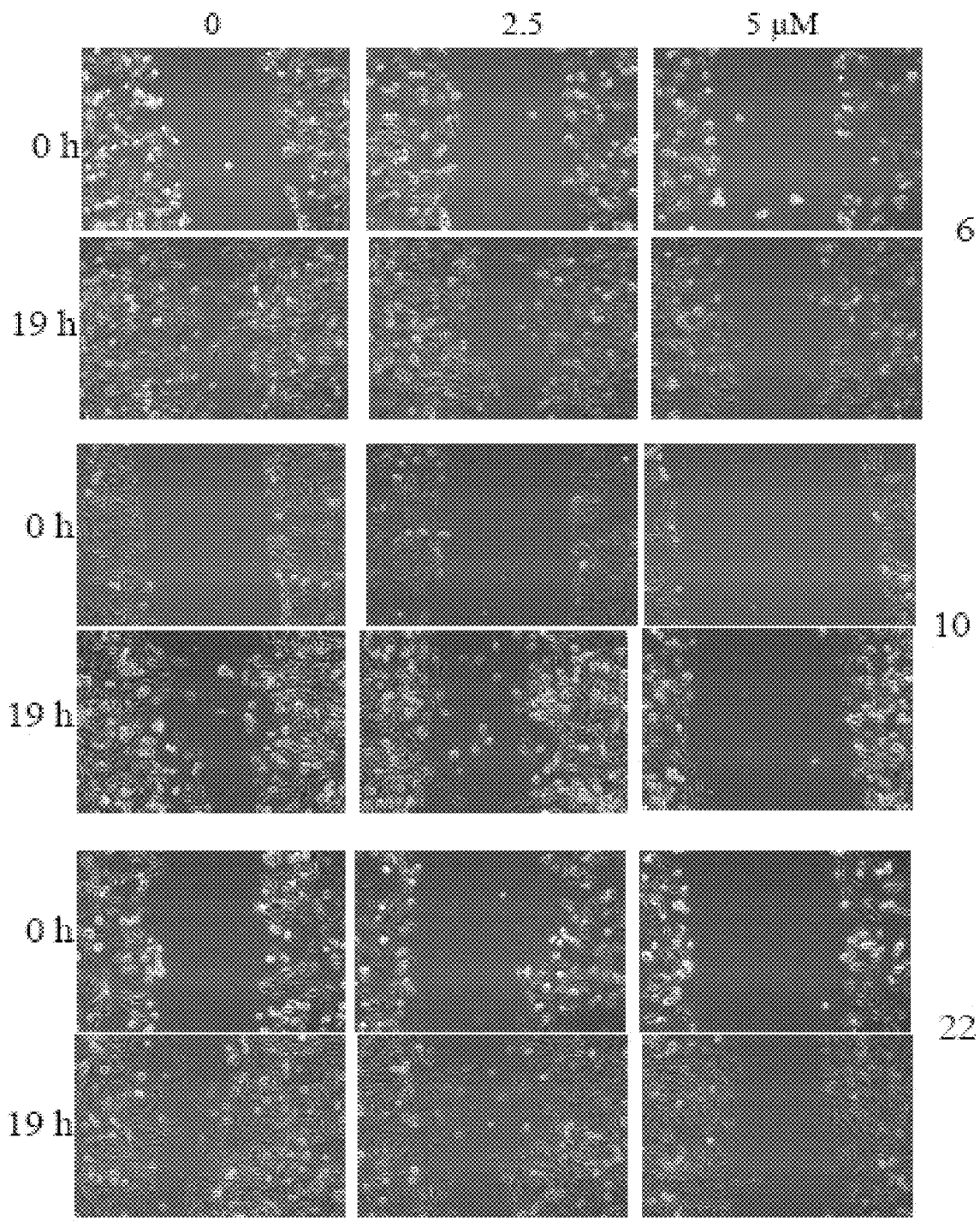
FIGS. 18A-18B show that purified hirsutinolide compounds inhibit colony survival, induce cell cycle arrest and apoptosis and inhibit cell migration in vitro: (C) human glioma U251MG cells in culture were wounded and treated once with 0-5 micromolar of the designated compounds for 19 h and allowed to migrate to the denuded area and imaged (left panel). Viable cell numbers at 19 h post-treatment were counted and are represented (right panel). Values are the mean and S.D. of 3-4 independent determinations. Data are representative of 3 independent determinations.
Figure 18B:
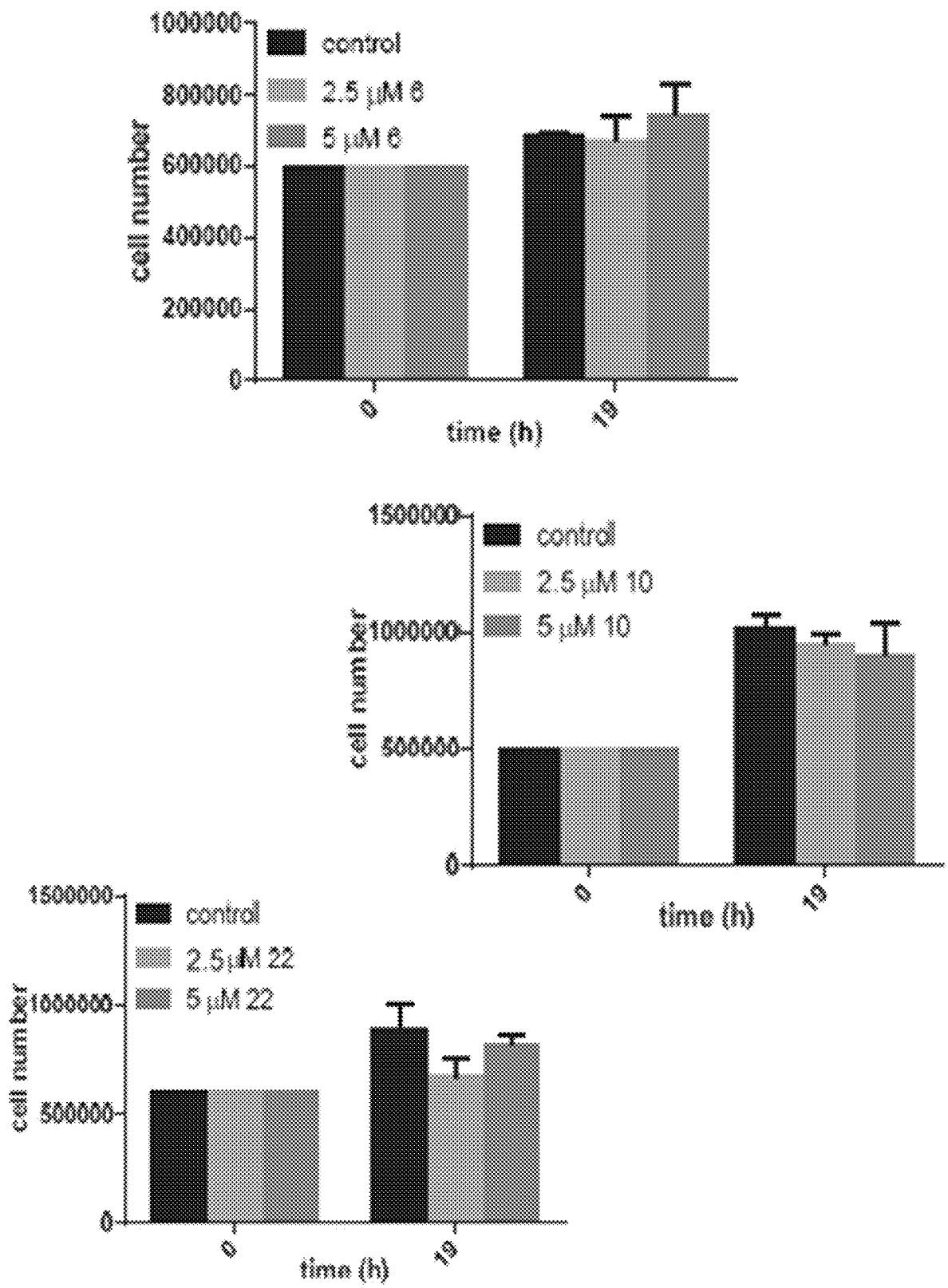
Figure 19:
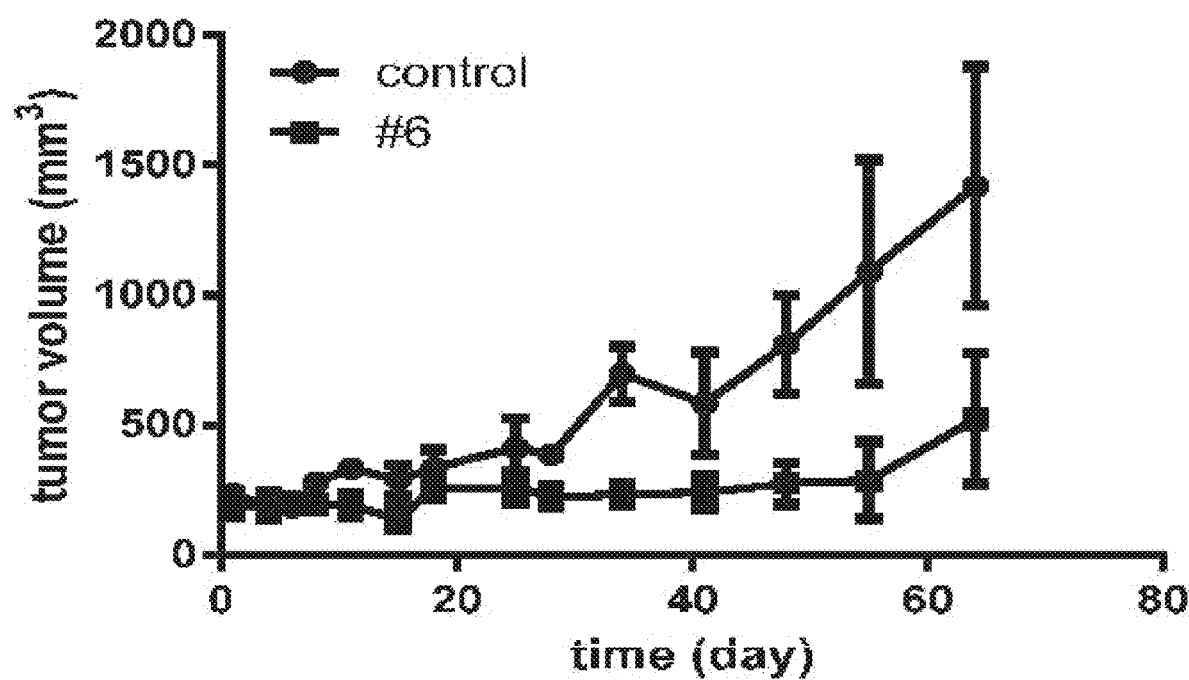
FIG. 19 shows antitumor effects against human glioma tumor xenografts and in vivo. Mice bearing U251MG subcutaneous tumor xenografts were administered compound 6 via oral gavage, 2 mg/kg or vehicle (1% DMSO) every day for the indicated time. Tumor sizes, measured every 3 or 7 days were converted to tumor volumes and plotted against days of treatment. Values, mean±S.D., n=6.
Figure 20:
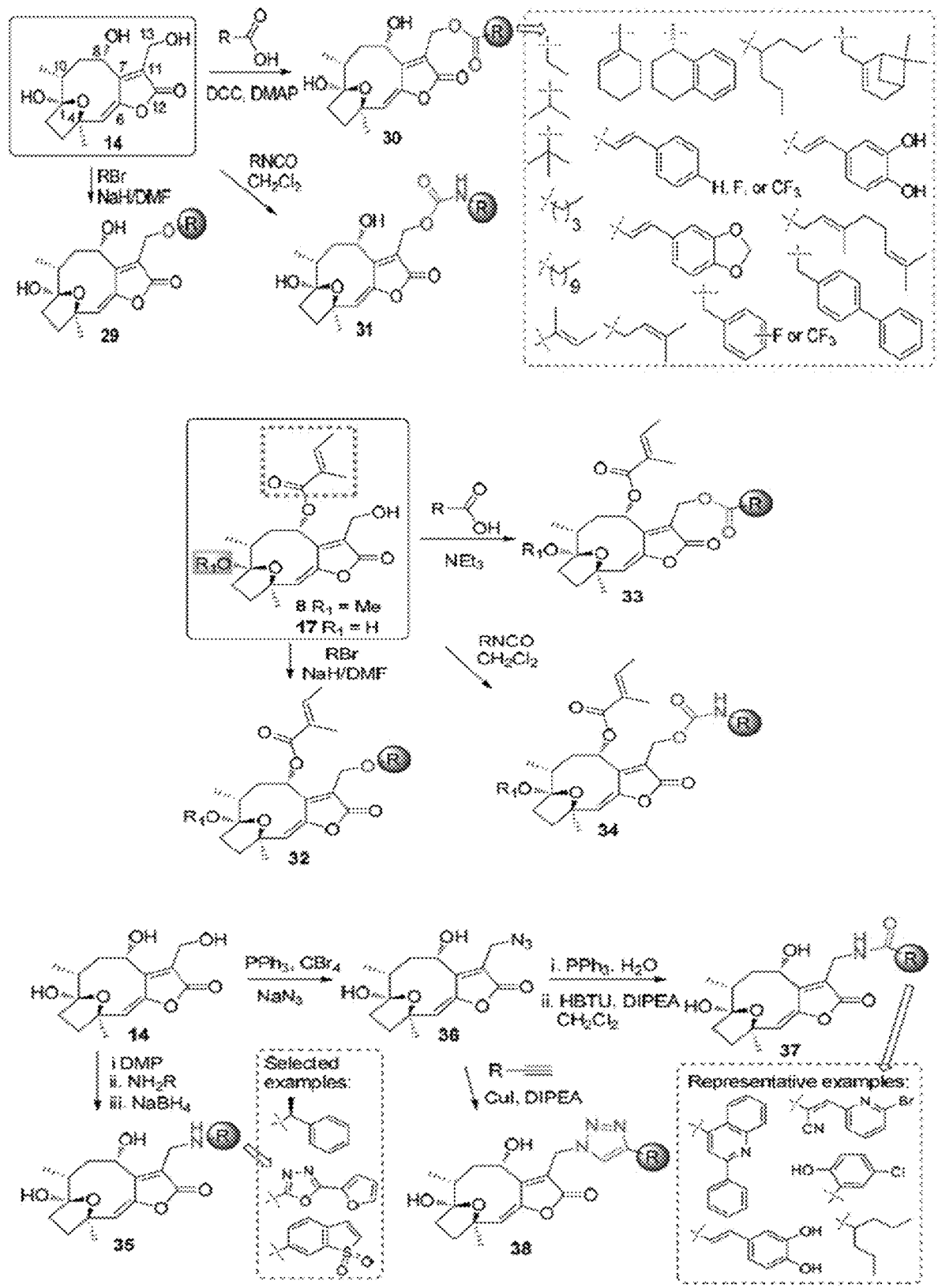
FIG. 20 shows the synthetic scheme for synthetic derivatives of the purified compounds from Vc.

8α-(2'Z-Tigloyloxy)hirsutmolide (1): white amorphous powder; $[\alpha]_D^{20}$=+28.5° (c 0.2, MeOH); UV (MeOH) $\lambda_{max}$ (log ε) 290 (4.0) nm; CD (c 0.1, MeOH) 289 (+35.3); IR $\nu_{max}$ (KBr) 3320, 1760 cm$^{-1}$; $^1$H (400 MHz) and $^{13}$C NMR (100 MHz) data, see Table 2; HRESIMS m/z 401.1724 [M+Na]$^+$ (calcd for $C_{20}H_{26}O_7Na$, 401.1726). Compound 1 was obtained as a white amorphous powder and gave a molecular ion at m/z 401.1724 [M+Na]$^+$ (calcd for $C_{20}H_{26}O_7Na$, 401.1726) in the positive-ion HRESIMS, corresponding to a molecular formula of $C_{20}H_{26}O_7$. The IR absorption band at 1760 cm$^{-1}$ and a strong absorption around 290 nm in the UV spectrum indicated the presence of a conjugated lactone group. The $^{13}$C NMR spectrum showed characteristic signals that further supported the γ lactone group [$\delta_C$, 169.4 (C-12), 147.5 (C-7), 146.4 (C-6), and 131.6 (C-11)]. (Kuo, Y.-H.; Kuo, Y.-J.; Yu, A.-S.; Wu, M.-D.; Ong, C.-W.; Kuo, L.-M. Y.; Huang, J.-T.; Chen, C.-F.; Li, S.-Y. *Chem. Pharm. Bull.* 2003, 51, 425-426). The NMR and HSQC spectra revealed two methyls at [$\delta_H$, 0.97 (d, J=6.8 Hz)/$\delta_C$, 16.8 ($CH_3$-14) and $\delta_H$, 1.48 (s)/$\delta_C$, 27.9 ($CH_3$-15)], three methylenes at [$\delta_H$, 2.16 m/$\delta_C$, 38.5 (C-2), $\delta_H$, 2.16 m/$\delta_C$, 38.6 (C-3), and $\delta_H$, 2.36 (dd, J=15.62, 11.6 Hz, H-9α), 1.87 (m, H-9β)/$\delta_C$, 37.9 (C-9)], a methine at $\delta_H$, 1.90 (m)/$\delta_C$, 41.3 (C-10), a downfield shifted oxymethine at $\delta_H$, 6.34 (d, J=8.0 Hz)/$\delta_C$, 68.2 (C-8), and an olefinic signal at $\delta_H$, 5.87 (s)/$\delta_C$, 125.6 (C-5), all of which suggested the presence of a hirsutinolide-type sesquiterpene. The $^1$H NMR spectrum revealed additional oxygenated methylene protons at $\delta_H$, 4.65 (d, J=13.2 Hz, H-13α) and 4.56 (d, J=13.2 Hz, H-13β), which showed two- and three-bond correlation peaks with C-7, C-12, and C-11 in the HMBC spectrum (FIG. 1), and suggested that this oxymethylene group was attached to the γ lactone group. In addition, the $^1$H and $^{13}$C NMR spectra showed an olefinic signal at $\delta_H$, 6.17 (q, J=7.6 Hz)/$\delta_C$, 139.9 (C-3'), two downfield-shifted methyl groups at [$\delta_H$, 2.02 (d, J=7.6 Hz)/$\delta_C$, 15.9 (C-4') and $\delta_H$, 1.93 (5)/$\delta_C$, 20.6 (C-5')], an olefinic quaternary carbon at $\delta_C$, 128.2 (C-2'), and an ester carbonyl carbon at $\delta_C$, 170.4 (C-1'), that were indicative of a tigloyl moiety by the HSQC and HMBC analyses. The $^1$H and $^{13}$C NMR spectra of 1 were almost identical, to those of 8α-tigloyloxy-hirsutinolide (Kuo, Y.-H.; Kuo, Y.-J.; Yu, A.-S.; Wu, M.-D.; Ong, C.-W.; Kuo, L.-M. Y.; Huang, J.-T.; Chen, C.-F.; Li, S.-Y. *Chem. Pharm. Bull.* 2003, 51, 425-426), with the following exceptions: the signal for an olefinic proton (H-3') at $\delta_H$, 7.03 in 8α-tigloyloxy-hirsutinolide was shifted upfield to $\delta_H$, 6.17 in 1. In contrast, two methyl group protons at $\delta_H$, 1.78 ($CH_3$-4') and $\delta_H$, 1.80 ($CH_3$-5') in 8α-tigloyloxy-hirsutinolide were shifted downfield to 2.02 ppm and 1.93 ppm, respectively, in the tigloyl group of 1, implying that the olefinic (C-2'-C-3') bond was in the Z configuration. This was also supported by the NOESY correlation between H-3' and $CH_3$-5' (FIG. 6). Additional NOESY correlations between H-8 and H-9β/H-13 along with the physicochemical data supported the same configurations in the sesquiterpene lactone molecule, and was comparable with literature data. (Kuo, Y.-H.; supra) In particular, X-ray crystallographic analysis (Youn, U. J.; Park, E.-J.; Kondratyuk, T. P.; Simmons, C. J.; Borris, R. P.; Tanamatayarat, P.; Wongwiwatthananukit, S.; Toyama, O.; Songsak, T.; Pezzuto, J. M.; Chang, L. C.; *Bioorg. Med. Chem. Lett.*, 2012, 22, 5559-5562) defined the relative configuration of 8α-tigloyloxy-hirsutinolide obtained in our previous work. Therefore, compound 1 is proposed as a new hirsutinolide geometric isomer, 8α-(2'Z-tigloyloxy)hirsutinolide.

8α-(2'Z-Tigloyloxy)hirsutinolide-13-O-acetate (2): white amorphous powder; $[\alpha]_D^{20}$=+20.3° (c 0.2, MeOH); UV (MeOH) $\lambda_{max}$ (log ε) 290 (4.2) nm; CD (c 0.1, MeOH) 289 (+36.6); IR $\nu_{max}$ (KBr) 3335, 1760 cm$^{-1}$; $^1$H (400 MHz) and $^{13}$C NMR (100 MHz) data, see Table 2; HRESIMS m/z 443.1817 [M+Na]$^+$ (calcd for $C_{22}H_{28}O_8Na$, 443.1829). Compound 2 was obtained as a white amorphous powder. It had a molecular ion at 443.1817 [M+Na]$^+$ (calcd for $C_{22}H_{28}O_8Na$, 443.1829) in the HRESIMS. The $^1$H and $^{13}$C NMR spectra of 2 were similar to those of 1, except for an additional methyl group at $\delta_H$, 2.10 (3H, 5)/$\delta_C$, 20.9 and a carbonyl carbon at $\delta_C$, 170.7, consistent with the acetyl moiety of an ester. The HMBC spectrum showed a correlation peak between H-13 and the ester carbonyl carbon ($\delta_C$, 170.7), suggesting that the acetyl group was attached to an oxygen atom at C-13. The chemical shifts and the NOESY correlation between H-3' and $CH_3$-5' in the tigloyl group supported the cis (Z) olefinic double bond between C-2' and C-3'. The stereochemistry of asymmetric carbons of the sesquiterpene skeleton was the same as in 1, by comparison of the physicochemical data and NOESY correlations of the two compounds. Thus, compound 2 was elucidated as a new geometric isomer, 8α-(2'Z-tigloyloxy)hirsutinolide-13-O-acetate.

8α-(4-Hydroxytigloyloxy)-hirsutinolide (3): white amorphous powder; $[\alpha]_D^{20}$=+25.5° (c 0.2, MeOH); UV (MeOH) $\lambda_{max}$ (log ε) 288 (4.1) nm; CD (c=0.1, MeOH) 290 (+35.6); IR $\nu_{max}$ (KBr) 3330, 1760 cm$^{-1}$; $^1$H (400 MHz) and $^{13}$C NMR (100 MHz) data, see Table 2; HRESIMS m/z 417.1660 [M+Na]$^+$ (calcd for $C_{20}H_{26}O_8Na$, 417.1672). Compound 3 was obtained as a white amorphous powder and its molecular formula was established as $C_{20}H_{26}O_8$ by HRESIMS (observed, 417.1660; calcd for [M+Na]$^+$ 417.1672). The UV, IR, and NMR spectra of 3 indicated a hirsutinolide skeleton comparable to those of 1 and 2. However, the $^1$H NMR spectrum revealed additional oxygenated methylene protons at $\delta_H$, 4.28 (2H, d, J=6.4 Hz, H-4'), which showed two- and three-bond HMBC correlations with the two olefinic carbons (C-2' and C-3'), indicating the attachment of an oxymethylene group instead of a methyl group at C-3' of the tigloyl moiety. The specific splitting pattern and the coupling constant of the olefinic proton (H-3') at $\delta_H$, 7.08 (t, J=6.4 Hz) appeared to result from coupling with the oxymethylene proton (H-4'), and further supported the presence of the 4-hydroxytigloyl moiety. In addition, the HMBC correlation observed between H-8 and the ester carbonyl carbon (C-1') demonstrated that the 4-hydroxytigloyl group was attached to C-8 of the sesquiterpene lactone molecule. The relative stereochemistry of 3 was determined in a manner similar to those of 1 and 2. Accordingly, compound 3 is proposed as a new compound, 8α-(4-hydroxytigloyloxy)-hirsutinolide.

8α-Hydroxy-13-O-tigloyl-hirsutmolide (4): white amorphous powder; $[\alpha]_D^{20}$=+27.7° (c 0.2, MeOH); UV (MeOH) $\lambda_{max}$ (log ε) 290 (4.0) nm; CD (c=0.1, MeOH) 294 (+40.3); IR $\nu_{max}$ (KBr) 3335, 1760 cm$^{-1}$; $^1$H (400 MHz) and $^{13}$C NMR (100 MHz) data, see Table 2; HRESIMS m/z 401.1722 [M+Na]$^+$ (calcd for $C_{20}H_{26}O_7Na$, 401.1723). Compound 4 was obtained as a white amorphous powder with an ion at m/z 401.1722 [M+Na$^+$](calcd for $C_{20}H_{26}O_7Na$, 401.1723) in the HRESIMS, corresponding to a elemental formula of $C_{20}H_{26}O_7$. The 1D and 2D NMR spectra of 4 showed a (2'E)-tigloyl moiety, three methylenes, two methyls, an olefinic, an oxymethine, and a γ lactone, indicating a hirsutinolide-type sesquiterpene lactone, initially assumed from the spectra data to be similar to 8α-tigloyloxyhirsutinolide (6) However, the $^1$H NMR spectrum of 4 showed an additional hydroxyl proton at $\delta_H$, 6.15 (1H, d, J=11.6 Hz), which correlated with C-7/C-8/C-9 in the HMBC spectrum (FIG. 6), indicating that the hydroxyl group was connected to C-8. In addition, magnetically equivalent oxygenated methylene protons at $\delta_H$, 4.97 (2H, s, H-13) were observed in the $^1$H NMR spectra, which also showed a three-bond correlation with a lactone carbonyl carbon (C-12) and an ester carbonyl carbon (C-1') of a tigloyl moiety in the HMBC spectrum. This data unambiguously indicated that the tigloyl group was attached at C-13 through an oxygen atom (FIG. 1). The NOESY correlation peaks between α-oriented OH-8 and H-9α and between H-13 and H-8 (FIG. 6), along with the physicochemical analyses of 4 supported the same relative stereochemistry compared to those of 1-3. Therefore, the structure of 4 was established as a new compound, 8α-hydroxy-13-O-tigloyl-hirsutinolide.

The other eight isolates were identified as the known compounds, 8α-(2-methylacryloyloxy)-hirsutinolide (5) (Youn, U. J.; Park, E.-J.; Kondratyuk, T. P.; Simmons, C. J.; Borris, R. P.; Tanamatayarat, P.; Wongwiwatthananukit, S.; Toyama, O.; Songsak, T.; Pezzuto, J. M.; Chang, L. C.; Bioorg. Med. Chem. Lett., 2012, 22, 5559-5562), 8α-tigloyloxyhirsutinolide (6) (Kuo, Y.-H.; supra), 8α-tigloyloxyhirsutinolide-13-O-acetate (7) (Kuo, Y.-H.; supra), 8α-(2-methylacryloyloxy)-hirsutinolide-13-O-acetate (8) (Kuo, Y.-H.; supra), 8α-(2-methylacryloyloxy)-1α-methoxyhirsutinolide-13-O-acetate (9) (Jakupovic, J.; Schmeda-Hirschmann, G.; Schuster, A.; Zdero, C.; Bohlmann, F.; King, R. M.; Robinson, H.; Pickardt, J. Phytochemistry 1986, 25, 145-158), vernolide-B (10) (Kuo, et al, supra), hirsutinolide-13-O-acetate (11) (Kuo, et al, supra), and vernolide-A (12) (Kuo, Y.-H.; supra), by comparison of their physical and spectral data with published values.

Example 12

Cell Viability Assay of the Formulations Incorporating Isolated Compounds 1-4

The cell viability assay was performed as previously reported (Zhang X, et al. (2010)). Briefly, a 10 millimolar concentration stock solution in dimethylsulfoxide (DMSO) of the tested molecule was first prepared. Next, the stock solution was diluted down to various working solutions in water. Thus, a formulation of the tested compound in a DMSO/water mixture was used to test for cell viability. (A novel small-molecule disrupts STAT3 SH2 domainphosphotyrosine interactions and STAT3-dependent tumor processes, Biochem Pharmacol 79:1398-1409; Zhao W, Jaganathan S, & Turkson J (2010), A cell-permeable STAT3 SH2 domain mimetic inhibits STAT3 activation and induces antitumor cell effects in vitro. J Biol Chem. 285:35855-35865). Cells (U251MG, MDA-MB-231 or NIH3T3) were obtained from ATCC (Manassas, Va.) and were cultured in 96-well plates at 2,000 cells per well for 24 h and were treated with compounds (5 micromolar concentration) for 72 h. Cell viabilty was determined using CyQuant assay, according to the manufacturer's (Invitrogen, CA, USA) instructions. Relative viability of the treated cells was normalized to the DMSO-treated control cells. The results are shown in Table 3.

TABLE 3

Cell viability results of formulations comprising isolated compounds 1-16.

| compounds | U251MG[a] % inhibition[d] | MDA-MB-231[b] % inhibition | NIH-3T3[c] % inhibition |
|---|---|---|---|
| Control | ne[e] | ne | ne |
| 1 | ne | ne | ne |
| 2 | 48.6 | ne | 8.0 |
| 3 | ne | ne | ne |
| 4 | 80.9 | 26.2 | 32.1 |
| 5 | ne | ne | ne |
| 6 | 18.0 | 15.0 | ne |
| 7 | 88.8 | 81.7 | 76.0 |
| 8 | 64.8 | 37.8 | 50.7 |
| 9 | 67.7 | 14.0 | ne |
| 10 | 6.0 | ne | ne |
| 11 | ne | ne | ne |
| 12 | ne | ne | ne |
| 13 | nd[f] | nd | nd |
| 14 | ne | ne | ne |
| 15 | ne | ne | ne |

TABLE 3-continued

Cell viability results of formulations comprising isolated compounds 1-16.

| compounds | U251MG[a] % inhibition[d] | MDA-MB-231[b] % inhibition | NIH-3T3[c] % inhibition |
|---|---|---|---|
| 16 | ne | ne | ne |
| costunolide | 17.5 | 10.5 | 41.6 |
| parthenolide | 52.0 | 18.7 | 79.4 |

Control measurement was performed with the solubilising agent (DMSO),
[a]glioblastoma cancer cell,
[b]breast cancer cell,
[c]mouse fibroblast cell,
[d]% inhibition at 5 μM,
[e]ne, no effect inhibition,
[f]nd, not determined.

Example 13

Western Blotting Analysis for pYSTAT3 and STAT3

Whole-cell lysates were prepared in boiling SDS sample loading buffer to extract total proteins, as reported previously. (Turkson J, et al. (1998) STAT3 activation by Src induces specific gene regulation and is required for cell transformation. *Mol. Cell. Biol.* 18:2545-2552; Turkson J, et al. (2004) Inhibition of constitutive signal transducer and activator of transcription 3 activation by novel platinum complexes with potent anti-tumor activity, *Mol. Cancer Ther.* 3:1533-1542; Turkson J, et al. (2004) Novel peptidomimetic inhibitors of signal transducer and activator of transcription 3 dimerization and biological activity, *Mol Cancer Ther.* 3:261-269). Lysates of equal total protein prepared from DMSO- or compound-treated cells were electrophoresed on an SDS-7.5% polyacrylamide gel and transferred to a nitrocellulose membrane. Nitrocellulose membranes were probed with primary antibodies, and the detection of horseradish peroxidase-conjugated secondary antibodies by enhanced chemiluminescence (Amersham) was performed. Antibodies used were monoclonal anti-pYSTAT3 and anti-STAT3 antibodies (Cell Signaling Technology, Danvers, Mass.).

Figure 5:
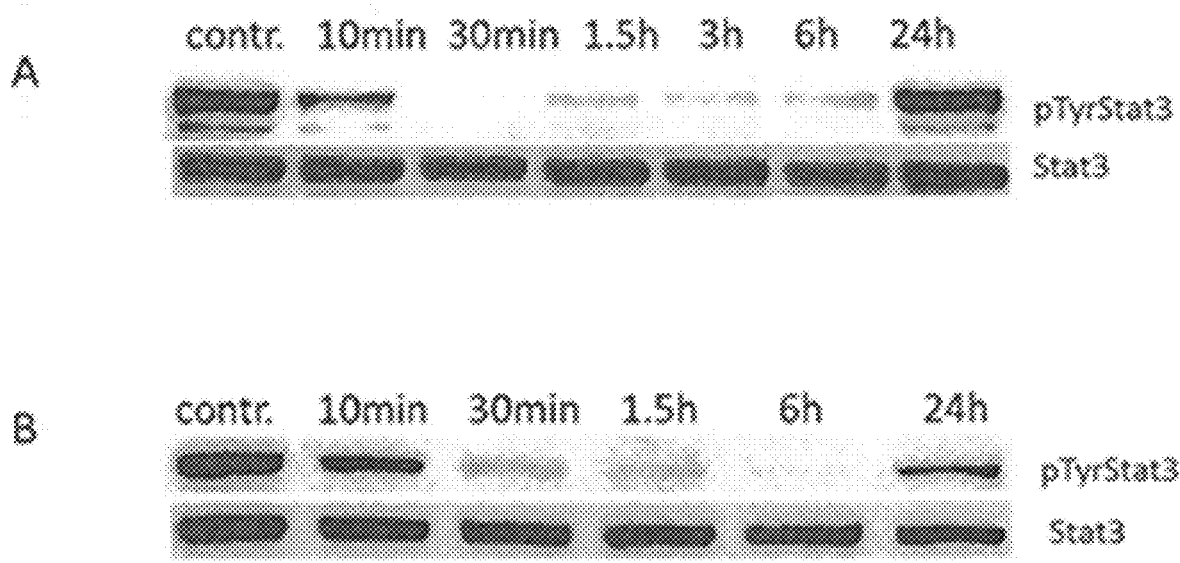
FIGS. 5A-5B show a Western Blot Analysis for pYSTAT3 and STAT3 after timed exposure to formulations comprising isolated compound 8α-(2'Z-Tigloyloxy)hirsutinolide-13-O-acetate, at 5 micromolar concentration as a DMSO/water solution. The formulation inhibited STAT3 phosphorylation in gliomablastoma multiforme cells (U251MG), (A), and breast cancer cells (MDA-MB-231), (B), as detected by Western Blot analysis. The formulation comprising compound 2 inhibits STAT3 activation.

The results are shown in FIG. 5.

Example 14

Synthesis of Natural Product Derivatives

Figure 3:
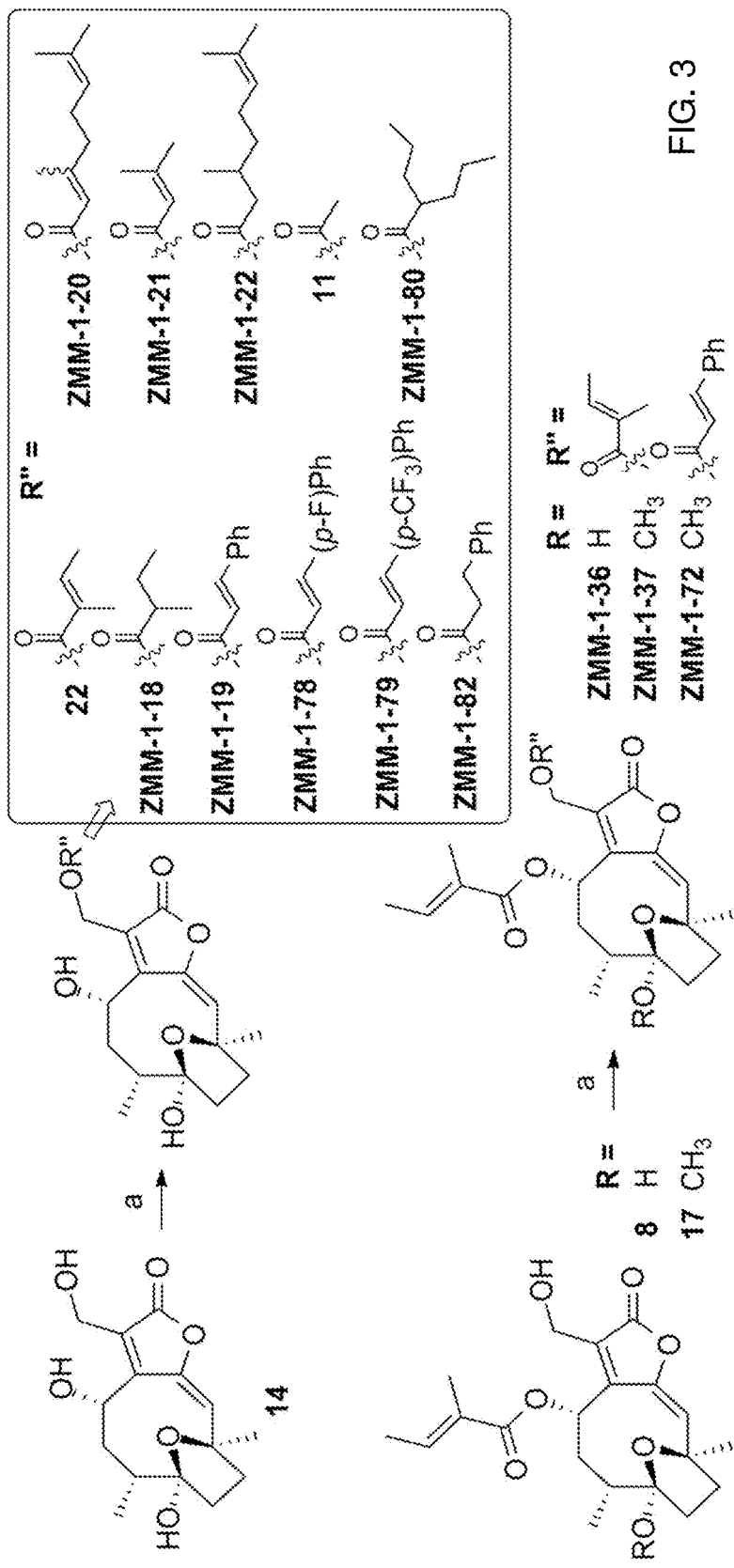
FIG. 3 shows the synthesis of hirsutinolide compounds using reaction conditions (a) Appropriate carboxylic acid (R"COOH), DCC, DMAP, $CH_2Cl_2$, room temperature (rt), 24 h, 40-85%.
Figure 4:
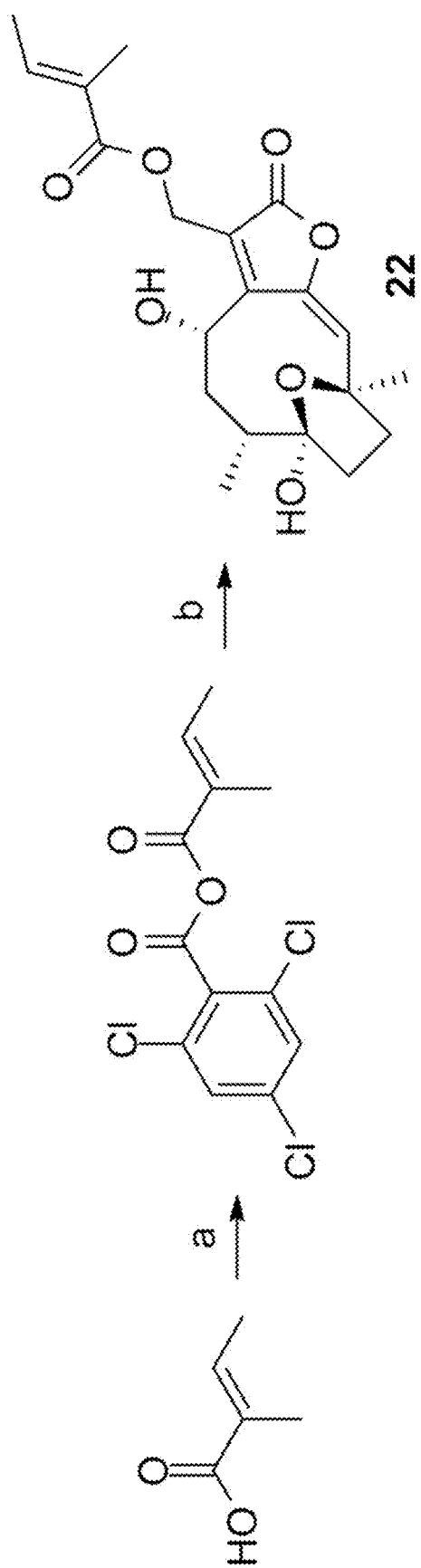
FIG. 4 shows synthesis of compound 22 using reaction conditions (a) 2,4,6-trichlorobenzoyl chloride, diisopropylethylamine (DIPEA), toluene, rt, 5 h, 32%; reaction conditions (b) 14, DMAP, toluene, 50° C., 24 h, 78%.

Synthesis of compound 22 or its derivatives was initiated using compound 14 as a starting material. Based upon encouraging biological data and to expand the existing SAR of isolated natural hirsutinolide analogues, a series of synthetic hirsutinolide derivatives including the synthesis of compounds 22 and 11 was subsequently synthesized (FIG. 3). This was accomplished by reacting compounds 14, 8 and 17 with a selected panel of carboxylic acids in the presence of dicyclohexylcarbodiimide (DCC) and catalytic amounts of 4-(dimethylamino)pyridine (DMAP) by conventional Steglich esterification [Inanaga, J., et al., A rapid esterification by means of mixed anhydride and its application to large-ring lactonization. Bull Chem Soc Jpn 1979, 52: p. 1989-1993], affording the desired synthetic derivatives in 40-85% yields. Due to the difficulty in removing the dicyclohexylurea byproduct and to further facilitate the purification process, Yamaguchi esterification protocol was employed to scale-up synthesis of compound 22 for subsequent in vivo efficacy studies [Inanaga, supra]. Briefly, the Yamaguchi mixed anhydride was generated in situ from 2,4,6-trichlorobenzoyl chloride and tiglic acid [Ball, M., et al., Total synthesis of thapsigargin, a potent SERCA pump inhibitor. Org Lett 2007, 9: p. 663-666], followed by the treatment with compound 14 in the presence of catalytic DMAP in toluene to afford compound 22 in 78% yield (FIG. 4). Title compounds were purified by normal phase column chromatography, preparative TLC, and/or semi-preparative reverse phase HPLC. The spectroscopic data of our synthetic compounds 22 and 11 are in full agreement with those of isolated natural products.

General Information

Solvents and reagents were purchased from Sigma-Aldrich and Fisher Scientific and used without further purification. All reactions were monitored by either TLC or HPLC (Shimadzu LC-20A series system). Compounds were purified by flash column chromatography on silica gel using a Biotage Isolera One system, preparative silica gel TLC plate (w/UV254, glass backed, 500 micromolar, 20×20 cm; Sorbent Technologies), and/or semi-preparative reverse phase HPLC. Proton nuclear magnetic resonance ($^1$H NMR) spectra were recorded employing a Bruker AM-400 spectrometer. Chemical shifts were expressed in parts per million (ppm), J values were in Hertz. Mass spectra were recorded on a Varian 500-MS IT mass spectrometer using ESI. The purity of compounds was determined by analytical HPLC (Shimadzu LC-20A series) using a Gemini, 3 μM, C18, 110 Å column (50 mm×4.6 mm, Phenomenex) and flow rate of 1 mL/min. Gradient conditions: solvent A (0.1% trifluoroacetic acid in water) and solvent B (acetonitrile): 0-2.0 min 100% A, 2.0-7.0 min 0-100% B (linear gradient), 7.0-8.0 min 100% B. UV detection at 254 nm and 284 nm. All the tested compounds were obtained with ≥96.0% purity by HPLC.

General Procedure for the Synthesis of Hirsutinolide Derivatives

To a stirred solution of compounds 14, 8, or 17 (0.0068 mmol) in anhydrous $CH_2Cl_2$ (2 mL) was added DMAP (0.42 mg, 0.0034 mmol) and the appropriate carboxylic acid (0.0136 mmol). DCC (2.81 mg, 0.0136 mmol) was added to the reaction at 0° C. and the reaction mixture was then stirred for 5 min at 0° C. and 24 h at room temperature. The residue was purified by preparative TLC (Hexane-Ethyl Acetate as developing solvent) and/or semi-preparative reverse phase HPLC to give desired target compounds in 40-85% yields.

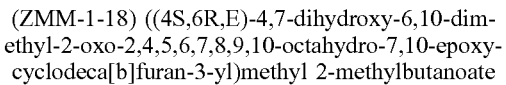
(ZMM-1-18) ((4S,6R,E)-4,7-dihydroxy-6,10-dimethyl-2-oxo-2,4,5,6,7,8,9,10-octahydro-7,10-epoxycyclodeca[b]furan-3-yl)methyl 2-methylbutanoate White amorphous powder (2.17 mg, 84%); $^1$H NMR (400 MHz, $CDCl_3$) δ 6.15 (d, J=11.5 Hz, 1H), 5.88 (s, 1H), 5.17 (dd, J=12.4, 6.1 Hz, 1H), 4.98-4.86 (m, 2H), 2.52 (s, 1H), 2.45-2.39 (m, 1H), 2.36 (d, J=7.7 Hz, 1H), 2.31-2.21 (m, 3H), 2.11-2.07 (m, 1H), 1.87 (dd, J=15.8, 7.0 Hz, 2H), 1.69 (s, 2H), 1.63 (s, 3H), 1.17 (dd, J=7.0, 1.2 Hz, 3H), 0.99 (d, J=6.9 Hz, 3H), 0.93 (t, J=8.0 Hz, 3H). LRMS (ES+) calculated for [$C_{20}H_{28}O_7$+Na] 403.2. found 403.4. HPLC purity: 99.2% (254 nm), $t_R$: 6.54 min, 99.2% (284 nm), $t_R$: 6.54 min.

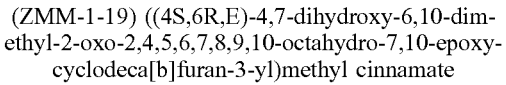
(ZMM-1-19) ((4S,6R,E)-4,7-dihydroxy-6,10-dimethyl-2-oxo-2,4,5,6,7,8,9,10-octahydro-7,10-epoxycyclodeca[b]furan-3-yl)methyl cinnamate White amorphous powder (2.46 mg, 85%); $^1$H NMR (400 MHz, $CDCl_3$) δ 7.74 (d, J=16.0 Hz, 1H), 7.53 (dd, J=6.8, 2.9

Hz, 2H), 7.46-7.36 (m, 3H), 6.44 (d, J=16.0 Hz, 1H), 6.19 (d, J=11.8 Hz, 1H), 5.89 (s, 1H), 5.30-5.19 (m, 1H), 5.06 (s, 2H), 2.65 (s, 1H), 2.32-2.16 (m, 4H), 2.11-2.03 (m, 1H), 1.95 (dd, J=12.1, 6.9 Hz, 1H), 1.92-1.84 (m, 1H), 1.63 (s, 3H), 0.97 (d, J=6.8 Hz, 3H). LRMS (ES+) calculated for $[C_{24}H_{26}O_7+Na]$ 449.2. found 449.1. HPLC purity: 97.1% (254 nm), $t_R$: 6.72 min, 97.7% (284 nm), $t_R$: 6.54 min.

(ZMM-1-20) ((4S,6R,E)-4,7-dihydroxy-6,10-dimethyl-2-oxo-2,4,5,6,7,8,9,10-octahydro-7,10-epoxycyclodeca[b]furan-3-yl)methyl 3,7-dimethylocta-2,6-dienoate White amorphous powder (1.37 mg, 45%); $^1$H NMR (400 MHz, CDCl$_3$) δ 6.16 (t, J=12.1 Hz, 1H), 5.87 (d, J=11.0 Hz, 1H), 5.24-5.04 (m, 2H), 4.98-4.87 (m, 2H), 2.31-2.05 (m, 10H), 2.00-1.92 (m, 2H), 1.92-1.82 (m, 2H), 1.70 (s, 3H), 1.63 (d, J=6.8 Hz, 6H), 0.98 (t, J=7.3 Hz, 3H). LRMS (ES+) calculated for $[C_{25}H_{34}O_7+Na]$ 469.2. found 469.5. HPLC purity: 99.8% (254 nm), $t_R$: 7.21 min, 99.9% (284 nm), $t_R$: 7.21 min.

(ZMM-1-21) ((4S,6R,E)-4,7-dihydroxy-6,10-dimethyl-2-oxo-2,4,5,6,7,8,9,10-octahydro-7,10-epoxycyclodeca[b]furan-3-yl)methyl 3-methyl but-2-enoate White amorphous powder (1.26 mg, 49%); $^1$H NMR (400 MHz, CDCl$_3$) δ 6.14 (d, J=11.8 Hz, 1H), 5.86 (s, 1H), 5.70-5.64 (m, 1H), 5.24-5.16 (m, 1H), 4.98-4.88 (m, 2H), 2.60 (s, 1H), 2.30-2.11 (m, 6H), 2.11-2.04 (m, 1H), 2.01-1.79 (m, 6H), 1.62 (s, 3H), 0.97 (d, J=6.8 Hz, 3H). LRMS (ES+) calculated for $[C_{20}H_{26}O_7+Na]$ 401.2. found 401.4. HPLC purity: 97.9% (254 nm), $t_R$: 6.43 min, 99.4% (284 nm), $t_R$: 6.43 min.

(ZMM-1-22) ((4S,6R,E)-4,7-dihydroxy-6,10-dimethyl-2-oxo-2,4,5,6,7,8,9,10-octahydro-7,10-epoxycyclodeca[b]furan-3-yl)methyl 3,7-dimethyloct-6-enoate White amorphous powder (2.34 mg, 77%); $^1$H NMR (400 MHz, CDCl$_3$) δ 6.17 (d, J=11.6 Hz, 1H), 5.88 (s, 1H), 5.24-5.12 (m, 1H), 5.09 (dd, J=7.7, 6.4 Hz, 1H), 4.97-4.85 (m, 2H), 2.65 (s, 1H), 2.41-1.80 (m, 13H), 1.70 (d, J=1.0 Hz, 4H), 1.62 (s, 3H), 1.61 (s, 4H), 0.99 (d, J=6.8 Hz, 3H), 0.96 (d, J=6.6 Hz, 3H). LRMS (ES+) calculated for $[C_{25}H_{36}O_7+Na]$ 471.2. found 471.4. HPLC purity: 98.9% (254 nm), $t_R$: 7.26 min, 98.8% (284 nm), $t_R$: 7.26 min.

(ZMM-1-23, resynthesized 11), ((4S,6R,E)-4,7-dihydroxy-6,10-dimethyl-2-oxo-2,4,5,6,7,8,9,10-octahydro-7,10-epoxycyclodeca[b]furan-3-yl)methyl acetate White amorphous powder (1.82 mg, 79%); $^1$H NMR (400 MHz, CDCl$_3$) δ 6.20 (d, J=11.8 Hz, 1H), 5.89 (s, 1H), 5.20-5.14 (m, 1H), 4.97-4.85 (m, 2H), 2.33-2.21 (m, 2H), 2.12-2.03 (m, 4H), 1.99-1.89 (m, 2H), 1.84 (ddd, J=15.7, 6.8, 2.3 Hz, 1H), 1.62 (s, 3H), 1.00 (d, J=6.8 Hz, 3H). LRMS (ES+) calculated for $[C_{17}H_{22}O_7+Na]$ 361.1. found 361.3. HPLC purity: 98.7% (254 nm), $t_R$: 5.84 min, 99.8% (284 nm), $t_R$: 5.84 min.

(ZMM-1-36) (4S,6R,E)-7-hydroxy-6,10-dimethyl-3-((((E)-2-methylbut-2-enoyl)oxy)methyl)-2-oxo-2,4,5,6,7,8,9,10-octahydro-7,10-epoxycyclodeca[b]furan-4-yl(E)-2-methylbut-2-enoate White amorphous powder (1.25 mg, 40%); $^1$H NMR (400 MHz, CD$_3$OD) δ 7.13 (dd, J=7.1, 1.5 Hz, 1H), 6.93 (dd, J=7.0, 1.4 Hz, 1H), 6.28 (d, J=7.6 Hz, 1H), 6.04 (s, 1H), 5.14 (d, J=13.0 Hz, 1H), 5.01 (d, J=12.9 Hz, 1H), 2.40 (dd, J=16.2, 12.2 Hz, 1H), 2.12 (dd, J=11.5, 5.6 Hz, 2H), 1.92-1.84 (m, 9H), 1.84-1.79 (m, 6H), 1.75 (s, 1H), 1.49 (s, 3H), 0.88 (d, J=6.9 Hz, 3H). LRMS (ES+) calculated for $[C_{25}H_{32}O_8+Na]$ 483.2. found 483.4. HPLC purity: 99.7% (254 nm), $t_R$: 7.14 min, 99.7% (284 nm), $t_R$: 7.14 min.

(ZMM-1-37) (4S,6R,E)-7-methoxy-6,10-dimethyl-3-((((E)-2-methylbut-2-enoyl)oxy)methyl)-2-oxo-2,4,5,6,7,8,9,10-octahydro-7,10-epoxycyclodeca[b]furan-4-yl(E)-2-methylbut-2-enoate White amorphous powder (1.35 mg, 42%); $^1$H NMR (400 MHz, CDCl$_3$) δ 7.05 (dd, J=7.1, 1.5 Hz, 1H), 6.95-6.84 (m, 1H), 6.27 (d, J=7.6 Hz, 1H), 5.87 (s, 1H), 5.20 (d, J=13.1 Hz, 1H), 5.07 (d, J=12.9 Hz, 1H), 3.29 (s, 3H), 2.38 (dd, J=15.6, 11.9 Hz, 1H), 2.23-2.07 (m, 2H), 2.02-1.86 (m, 3H), 1.84 (dt, J=2.6, 1.3 Hz, 6H), 1.80 (dd, J=7.1, 1.1 Hz, 6H), 1.76 (d, J=10.0 Hz, 1H), 1.51 (s, 3H), 0.86 (d, J=7.0 Hz, 3H). LRMS (ES+) calculated for $[C_{26}H_{34}O_8+Na]$ 497.2. found 497.5. HPLC purity: 99.8% (254 nm), $t_R$: 7.76 min, 99.8% (284 nm), $t_R$: 7.76 min.

(ZMM-1-72) (4S,6R,E)-3-((cinnamoyloxy)methyl)-7-methoxy-6,10-dimethyl-2-oxo-2,4,5,6,7,8,9,10-octahydro-7,10-epoxycyclodeca[b]furan-4-yl(E)-2-methylbut-2-enoate White amorphous powder (2.91 mg, 82%); $^1$H NMR (400 MHz, CDCl$_3$) δ 7.73 (d, J=16.0 Hz, 1H), 7.53 (dd, J=6.7, 2.9 Hz, 2H), 7.45-7.37 (m, 3H), 7.06 (dd, J=7.1, 1.5 Hz, 1H), 6.43 (d, J=16.0 Hz, 1H), 6.34 (d, J=7.8 Hz, 1H), 5.90 (s, 1H), 5.30 (d, J=13.0 Hz, 1H), 5.14 (d, J=12.9 Hz, 1H), 3.29 (s, 3H), 2.41 (dd, J=15.8, 11.3 Hz, 1H), 2.23-2.06 (m, 2H), 1.95 (ddd, J=16.9, 15.8, 9.5 Hz, 3H), 1.85 (dd, J=5.8, 4.5 Hz, 4H), 1.80 (dd, J=7.1, 1.1 Hz, 3H), 1.51 (s, 3H), 0.87 (d, J=6.9 Hz, 3H). LRMS (ES+) calculated for $[C_{30}H_{34}O_8+Na]$ 545.2. found 545.2. HPLC purity: 96.0% (254 nm), $t_R$: 7.88 min, 97.5% (284 nm), $t_R$: 7.88 min.

(ZMM-1-78) (4S,6R,E)-4,7-dihydroxy-6,10-dimethyl-2-oxo-2,4,5,6,7,8,9,10-octahydro-7,10-epoxycyclodeca[b]furan-3-yl)methyl(E)-3-(4-fluorophenyl)acrylate White amorphous powder (1.6 mg, 53%); $^1$H NMR (400 MHz, CDCl$_3$) δ 7.69 (d, J=16.0 Hz, 1H), 7.58-7.46 (m, 2H), 7.10 (t, J=8.6 Hz, 2H), 6.36 (d, J=16.0 Hz, 1H), 6.17 (d, J=11.8 Hz, 1H), 5.90 (s, 1H), 5.29-5.20 (m, 1H), 5.05 (s, 2H), 2.59 (s, 1H), 2.33-2.16 (m, 4H), 2.11-2.03 (m, 1H), 1.95 (dd, J=12.1, 6.8 Hz, 1H), 1.91-1.83 (m, 1H), 1.63 (s, 3H), 0.97 (d, J=6.8 Hz, 3H). LRMS (ES+) calculated for $[C_{24}H_{25}FO_7+Na]$ 467.1. found 467.1. HPLC purity: 96.4% (254 nm), $t_R$: 6.77 min, 97.2% (284 nm), $t_R$: 6.77 min.

(ZMM-1-79) (4S,6R,E)-4,7-dihydroxy-6,10-dimethyl-2-oxo-2,4,5,6,7,8,9,10-octahydro-7,10-epoxycyclodeca[b]furan-3-yl)methyl(E)-3-(4-(trifluoromethyl)phenyl)acrylate White amorphous powder (1.6 mg, 48%); $^1$H NMR (400 MHz, CDCl$_3$) δ 7.74 (d, J=16.0 Hz, 1H), 7.65 (q, J=8.5 Hz, 4H), 6.51 (d, J=16.0 Hz, 1H), 6.19 (d, J=11.8 Hz, 1H), 5.91 (s, 1H), 5.25 (dd, J=11.8, 5.4 Hz, 1H), 5.07 (s, 2H), 2.58 (s, 1H), 2.34-2.15 (m, 4H), 2.13-2.03 (m, 1H), 1.96 (dd, J=13.3, 5.9 Hz, 1H), 1.92-1.82 (m, 1H), 1.63 (s, 3H), 0.98 (d, J=6.8

Hz, 3H). LRMS (ES+) calculated for [$C_{25}H_{25}F_3O_7$+Na] 517.1. found 517.1. HPLC purity: 96.3% (254 nm), $t_R$: 7.04 min, 96.3% (284 nm), $t_R$: 7.04 min.

(ZMM-1-80) (4S,6R,E)-4,7-dihydroxy-6,10-dimethyl-2-oxo-2,4,5,6,7,8,9,10-octahydro-7,10-epoxycyclodeca[b]furan-3-yl)methyl 2-propylpentanoate White amorphous powder (1.4 mg, 49%); $^1$H NMR (400 MHz, CDCl$_3$) δ 6.16 (d, J=11.8 Hz, 1H), 5.89 (s, 1H), 5.21-5.12 (m, 1H), 4.91 (dd, J=30.8, 12.9 Hz, 2H), 2.58 (s, 1H), 2.45-2.34 (m, 1H), 2.24 (ddd, J=15.7, 13.0, 10.7 Hz, 3H), 2.11-2.03 (m, 1H), 1.92 (ddd, J=15.7, 9.4, 5.5 Hz, 2H), 1.63 (s, 3H), 1.44 (dddd, J=10.5, 7.7, 6.6, 4.0 Hz, 2H), 1.36-1.23 (m, 6H), 1.00 (d, J=6.8 Hz, 2H), 0.91 (td, J=7.3, 1.2 Hz, 6H). LRMS (ES+) calculated for [$C_{23}H_{34}O_7$+Na] 445.2. found 445.1. HPLC purity: 99.0% (254 nm), $t_R$: 7.09 min, 99.0% (284 nm), $t_R$: 7.09 min.

(ZMM-1-82) ((4S,6R,E)-4,7-dihydroxy-6,10-dimethyl-2-oxo-2,4,5,6,7,8,9,10-octahydro-7,10-epoxycyclodeca[b]furan-3-yl)methyl 3-phenylpropanoate White amorphous powder (2.0 mg, 69%); $^1$H NMR (400 MHz, CDCl$_3$) δ 7.34-7.17 (m, 5H), 6.15 (d, J=11.8 Hz, 1H), 5.88 (s, 1H), 5.17-5.08 (m, 1H), 4.91 (s, 2H), 2.97 (t, J=7.7 Hz, 2H), 2.66 (dd, J=8.4, 7.2 Hz, 2H), 2.57 (s, 1H), 2.28-2.15 (m, 4H), 2.10-2.02 (m, 1H), 1.90 (dd, J=10.9, 5.8 Hz, 1H), 1.78 (ddd, J=15.9, 6.9, 2.4 Hz, 1H), 1.62 (s, 3H), 0.96 (d, J=6.8 Hz, 3H). LRMS (ES+) calculated for [$C_{24}H_{28}O_7$+Na] 451.2. found 451.1. HPLC purity: 98.9% (254 nm), $t_R$: 6.68 min, 98.9% (284 nm), $t_R$: 6.68 min.

(E)-2,4,6-trichlorobenzoic (E)-2-methylbut-2-enoic anhydride

To a premixed solution of tiglic acid (300 mg, 3.0 mmol) and diisopropylethylamine (DIPEA, 0.62 mL, 3.6 mmol) in CH$_2$Cl$_2$ (15 mL) was added 2,4,6-trichlorobenzoyl chloride (0.61 mL, 3.6 mmol) dropwise at 0° C. The resulting solution was stirred at room temperature for 5 h. Dry ether (20 mL) was then added to precipitate DIPEA hydrochloride, followed by the filtration. The filtrate solution was concentrated and the residue was purified by flash column chromatography (1:3, CH$_2$Cl$_2$:hexanes) to afford the mixed anhydride as a white crystalline solid (293 mg, 32%). $^1$H NMR (400 MHz, CDCl$_3$) δ 7.43-7.36 (m, 2H), 7.17-7.10 (m, 1H), 1.91 (dd, J=2.2, 0.9 Hz, 3H), 1.91-1.88 (m, 3H). HPLC purity: 98.4% (254 nm), $t_R$: 7.55 min, 98.7% (284 nm), $t_R$: 7.55 min.

(22) (4S,6R,E)-4,7-dihydroxy-6,10-dimethyl-2-oxo-2,4,5,6,7,8,9,10-octahydro-7,10-epoxycyclodeca[b]furan-3-yl)methyl(E)-2-methylbut-2-enoate To a solution of 14 (18 mg, 0.061 mmol) in toluene (2 mL) was added DMAP (3.7 mg, 0.035 mmol) at room temperature. A solution of (E)-2,4,6-trichlorobenzoic (E)-2-methylbut-2-enoic anhydride (37.3 mg, 0.122 mmol) in toluene (1 mL) was next added, the reaction was heated at 80° C. for 24 h. After cooling to room temperature, the reaction mixture was concentrated under reduced pressure and purified by flash column chromatography on silica gel (1:5 to 1:2, ethyl acetate:hexanes), affording the title compound 22 as a white solid (19.6 mg, 85%). $^1$H NMR (400 MHz, CDCl$_3$) δ 6.89 (qd, J=7.0, 1.4 Hz, 1H), 6.15 (d, J=11.8 Hz, 1H), 5.87 (s, 1H), 5.19 (ddd, J=11.8, 6.8, 1.4 Hz, 1H), 4.97 (s, 2H), 2.25 (dd, J=9.1, 6.7 Hz, 1H), 2.20 (d, J=3.0 Hz, 1H), 2.18 (t, J=5.0 Hz, 1H), 2.10-2.05 (m, 1H), 1.97-1.89 (m, 1H), 1.89-1.85 (m, 1H), 1.86-1.83 (m, 3H), 1.81 (dd, J=7.1, 1.1 Hz, 3H), 1.62 (s, 3H), 0.96 (d, J=6.8 Hz, 3H). LRMS (ES+) calculated for [$C_{20}H_{26}O_7$+Na] 401.2. found 401.4. HPLC purity: 99.4% (254 nm), $t_R$: 6.42 min, 99.2% (284 nm), $t_R$: 6.42 min.

Patents, patent applications, publications, scientific articles, books, web sites, and other documents and materials referenced or mentioned herein are indicative of the levels of skill of those skilled in the art to which the inventions pertain. Each such referenced document and material is hereby incorporated by reference to the same extent as if it had been incorporated by reference in its entirety individually or set forth or reprinted herein in its entirety. Additionally, all claims in this application, and all priority applications, including but not limited to original claims, are hereby incorporated in their entirety into, and form a part of, the written description of the invention. Applicants reserve the right to physically incorporate into this specification any and all materials and information from any such patents, applications, publications, scientific articles, web sites, electronically available information, and other referenced materials or documents. Applicants reserve the right to physically incorporate into any part of this document, including any part of the written description, and the claims referred to above, including, but not limited to, any original claims.

The inventions have been described broadly and generically herein. Each of the narrower species and subgeneric groupings falling within the generic disclosure also form part of these inventions. This includes the generic description of each invention which hereby include, including any claims thereto, a proviso or negative limitation removing, or optionally allowing the removal of, any subject matter from the genus, regardless of whether or not the excised materials, or options, were specifically recited or identified in haec verba herein, and all such variations form a part of the original written description of the inventions. In addition, where features, or aspects, of an invention are described in terms of a Markush group, the invention shall be understood thereby to be described in terms of each and every, and any, individual member or subgroup of members of the Markush group.

Although the invention has been described in terms of synthesis of compounds which are derivative of Compound 14 and the salts thereof, it should be recognized that the routes, steps, and intermediates described in the disclosure are applicable to the synthesis of other compounds.

All of the references cited herein are incorporated by reference.

The inventions illustratively described and claimed herein can suitably be practiced in the absence of any element or elements, limitation or limitations, not specifically disclosed herein, or described herein, as essential. Thus, for example, the terms "comprising," "including," "containing," for example", etc., shall be read expansively and without limitation. The term "including" means "including but not limited to." The phrase for example" is not limited to, or by, the items that follow the phrase. All references to things "known in the art" include all those things and equivalents and substitutes, whether now known, or later discovered.

In claiming their inventions, the inventors reserve the right to substitute any transitional phrase with any other transitional phrase, and the inventions shall be understood to include such substituted transitions and form part of the original written description of the inventions. Thus, for example, the term "comprising" may be replaced with either of the transitional phrases "consisting essentially of" or "consisting of."

The methods and processes illustratively described herein may be suitably practiced in differing orders of steps. They are not necessarily restricted to the orders of steps indicated herein, or in the claims.

Under no circumstances may the patent be interpreted to be limited to the specific examples, or embodiments, or methods, specifically disclosed herein. Under no circumstances may the patent be interpreted to be limited by any Statement made by any Examiner, or any other official or employee of the Patent and Trademark Office, unless such Statement was specifically, and without qualification or reservation, expressly adopted by Applicants in a responsive writing specifically relating to the application that led to this patent prior to its issuance.

The terms and expressions employed herein have been used as terms of description and not of limitation, and there is no intention in the use of such terms and expressions, or any portions thereof, to exclude any equivalents now know or later developed, whether or not such equivalents are set forth or shown or described herein or whether or not such equivalents are viewed as predictable, but it is recognized that various modifications are within the scope of the invention claimed, whether or not those claims issued with or without alteration or amendment for any reason. Thus, it shall be understood that, although the present invention has been specifically disclosed by preferred embodiments and optional features, modifications and variations of the inventions embodied therein or herein disclosed can be resorted to by those skilled in the art, and such modifications and variations are considered to be within the scope of the inventions disclosed and claimed herein.

Specific methods and compositions described herein are representative of preferred embodiments and are exemplary of, and not intended as limitations on, the scope of the invention. Other objects, aspects, and embodiments will occur to those skilled in the art upon consideration of this specification, and are encompassed within the spirit of the invention as defined by the scope of the claims. Where examples are given, the description shall be construed to include, but not to be limited to, only those examples. It will be readily apparent to one skilled in the art that varying substitutions and modifications may be made to the invention disclosed herein, without departing from the scope and spirit of the invention, and from the description of the inventions, including those illustratively set forth herein, it is manifest that various modifications and equivalents can be used to implement the concepts of the present invention, without departing from its scope. A person of ordinary skill in the art will recognize that changes can be made in form and detail without departing from the spirit and the scope of the invention. The described embodiments are to be considered in all respects as illustrative and not restrictive. Thus, for example, additional embodiments are within the scope of the invention and within the following claims.

While this invention has been disclosed with reference to specific embodiments, it is apparent that other embodiments and variations of this invention can be devised by those skilled in the art, without departing from the true spirit and scope of the invention. The appended claims include all such embodiments and equivalent variations.

The invention claimed is:

1. A compound represented by Formula I:

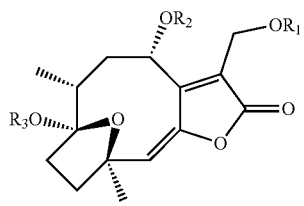

FORMULA I wherein $R_1$ is selected from the group consisting of methyl ($CH_3$), 4-hydroxytigloyl, tigloyl, 2-methylacryloyl, acryloyl, proponoyl, butanoyl, pentanoyl, hexanoyl, isodecenoyl, isopentenoyl, cinnamoyl, 3-(4-(trifluoromethyl)phenyl) acryl, 3-(4-fluorophenyl)acryl, 3,7-dimethylocta-2,6-dienoyl, 3-methylbut-2-enoyl, 3,7-dimethyloct-6-enoyl, ethylbut-2-enoyl, 2-methylbut-2-enoyl, and stilbenoyl;

$R_2$ is selected from the group consisting of H, 4-hydroxytigloyl, acryloyl, cinnamoyl, 3-(4-(trifluoromethyl)phenyl) acryl, 3-(4-fluorophenyl)acryl, 3,7-dimethylocta-2,6-dienoyl, 3-methylbut-2-enoyl, 3,7-dimethyloct-6-enoyl, 2-methylbut-2-enoyl, 2-methylbut-2-enoyl, acetyl, proponoyl, butanoyl, pentanoyl, hexanoyl, isodecenoyl, isopentenoyl, stilbenoyl, and oleoyl;

$R_3$ is selected from the group consisting of H, methyl ($CH_3$), and acetyl;

or pharmaceutically acceptable solvates, or pharmaceutically acceptable salts, thereof, with the proviso that when $R_2$ and $R_3$ are both H, $R_1$ is not tigloyl.

2. The compound of claim 1, where $R_1$ is selected from the group consisting of tigloyl, 4-hydroxytigloyl, 2-methylacryloyl, acryloyl, benzoyl, stilbenoyl, substituted stilbenoyl, oleoyl, cinnamoyl, 3-(4-(trifluoromethyl)phenyl) acryl, 3-(4-fluorophenyl)acryl, 3,7-dimethylocta-2,6-dienoyl, 3-methylbut-2-enoyl, 3,7-dimethyloct-6-enoyl, 2-methylbut-2-enoyl, 2-methylbut-2-enoyl, and $R_3$ is H.

3. The compound of any of claims 1 or 2, wherein the compound is the compound in Formula I, or a pharmaceutically acceptable salt, thereof.

4. A pharmaceutical composition for treating cancer comprising a therapeutically effective amount of a substantially pure isolated compound of the following formula:

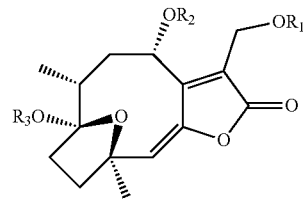

wherein $R_1$ is selected from the group consisting or methyl ($CH_3$), 4-hydroxytigloyl, tigloyl, 2-methylacryloyl, acryloyl, proponoyl, butanoyl, pentanoyl, hexanoyl, isodecenoyl, isopentenoyl, cinnamoyl, 3-(4-(trifluoromethyl)phenyl) acryl, 3-(4-fluorophenyl)acryl, 3,7-dimethylocta-2,6-dienoyl, 3-methylbut-2-enoyl, 3,7-dimethyloct-6-enoyl, 2-methylbut-2-enoyl, 2-methylbut-2-enoyl, stilbenoyl, and oleoyl;

$R_2$ is selected from the group consisting of H, 4-hydroxytigloyl, acryloyl, cinnamoyl, 3-(4-(trifluoromethyl)phenyl) acryl, 3-(4-fluorophenyl)acryl, 3,7-dimethylocta-2,6-dienoyl, 3-methylbut-2-enoyl, 3,7-dimethyloct-6-enoyl, 2-methylbut-2-enoyl, 2-methylbut-2-enoyl, acetyl, proponoyl, butanoyl, pentanoyl, hexanoyl, isodecenoyl, isopentenoyl, stilbenoyl, and oleoyl;

$R_3$ is selected from the group consisting of H or methyl ($CH_3$) or acetyl;

with the proviso that when $R_2$ and $R_3$ are both H, $R_1$ is not tigloyl, or pharmaceutically acceptable salts thereof;

and a pharmaceutically acceptable excipient.

5. A compound selected from:
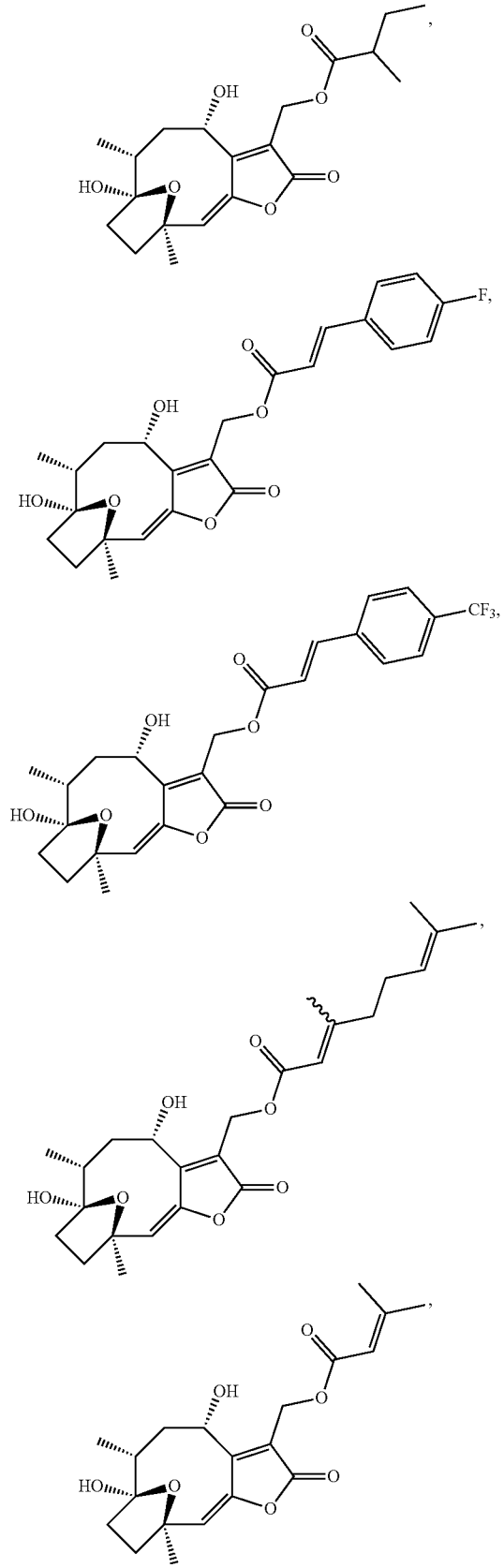
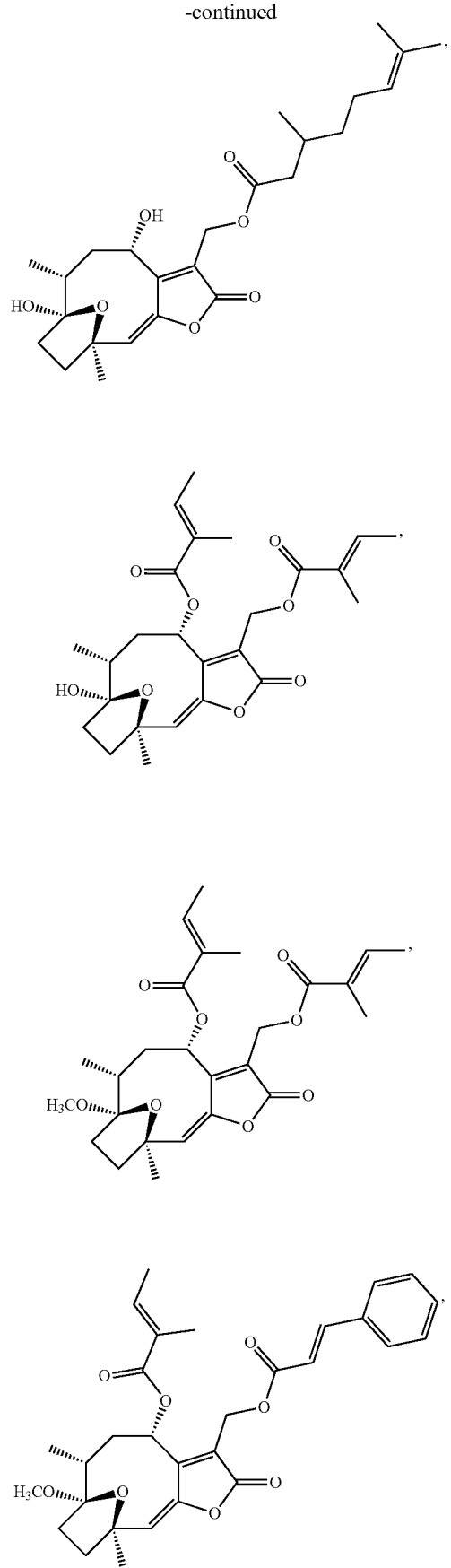

-continued
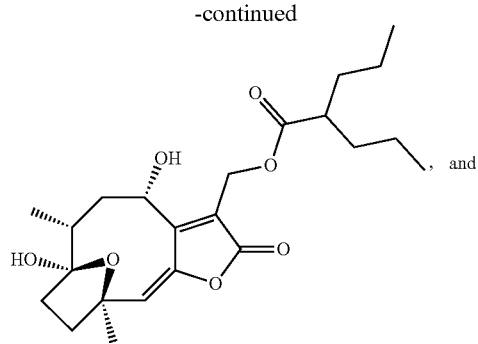, and
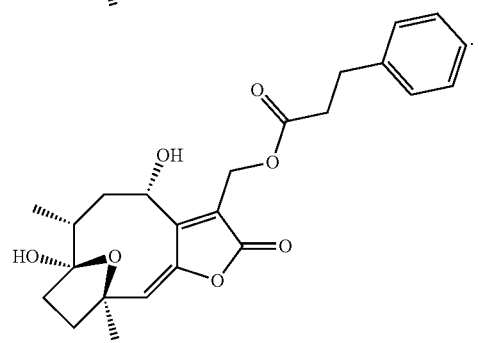.
* * * * *